(12) United States Patent
Hill

(10) Patent No.: US 11,384,388 B2
(45) Date of Patent: *Jul. 12, 2022

(54) DNA VACCINES

(71) Applicant: Touchlight IP Limited, London (GB)

(72) Inventor: Vanessa Hill, Surrey (GB)

(73) Assignee: Touchlight IP Limited

( * ) Notice: Subject to any disclaimer, the term of this patent is extended or adjusted under 35 U.S.C. 154(b) by 265 days.

This patent is subject to a terminal disclaimer.

(21) Appl. No.: 16/265,919

(22) Filed: Feb. 1, 2019

(65) Prior Publication Data

US 2019/0203282 A1 Jul. 4, 2019

Related U.S. Application Data

(60) Continuation of application No. 14/814,258, filed on Jul. 30, 2015, now abandoned, which is a division of application No. 13/146,350, filed as application No. PCT/GB2010/000165 on Feb. 1, 2010, now Pat. No. 9,109,250.

(30) Foreign Application Priority Data

Jan. 30, 2009 (GB) .................................... 0901593

(51) Int. Cl.
| | | |
|---|---|---|
| C12Q 1/68 | (2018.01) | |
| C12Q 1/6853 | (2018.01) | |
| C12N 15/11 | (2006.01) | |
| A61K 39/00 | (2006.01) | |
| A61K 48/00 | (2006.01) | |
| C12N 9/02 | (2006.01) | |
| C12Q 1/6844 | (2018.01) | |
| A61P 37/08 | (2006.01) | |
| A61P 39/02 | (2006.01) | |
| A61P 37/04 | (2006.01) | |
| A61P 35/00 | (2006.01) | |
| A61P 33/00 | (2006.01) | |
| A61P 37/00 | (2006.01) | |

(52) U.S. Cl.
CPC ............ *C12Q 1/6853* (2013.01); *A61K 39/00* (2013.01); *A61K 48/00* (2013.01); *A61P 33/00* (2018.01); *A61P 35/00* (2018.01); *A61P 37/00* (2018.01); *A61P 37/04* (2018.01); *A61P 37/08* (2018.01); *A61P 39/02* (2018.01); *C12N 9/0069* (2013.01); *C12N 15/11* (2013.01); *C12Q 1/6844* (2013.01); *C12Q 1/6846* (2013.01); *A61K 2039/53* (2013.01); *C12Y 113/12007* (2013.01)

(58) Field of Classification Search
None
See application file for complete search history.

(56) References Cited

U.S. PATENT DOCUMENTS

| | | |
|---|---|---|
| 5,589,466 A | 12/1996 | Felgner et al. |
| 5,714,320 A | 2/1998 | Kool |
| 5,720,923 A | 2/1998 | Haff et al. |
| 5,922,591 A | 7/1999 | Anderson et al. |
| 6,369,038 B1 | 4/2002 | Blumenfeld et al. |
| 6,451,563 B1 | 9/2002 | Wittig et al. |
| 6,620,597 B1 | 9/2003 | Chen et al. |
| 6,977,148 B2 | 12/2005 | Dean et al. |
| 7,074,772 B2 | 7/2006 | Wittig et al. |
| 7,452,699 B2 | 11/2008 | Makrigiorgos |
| 7,615,625 B2 | 11/2009 | Auerbach |
| 7,955,795 B2 | 6/2011 | Kumar |
| 8,093,030 B2 | 1/2012 | Schoenfeld et al. |
| 8,163,489 B2 | 4/2012 | Murray et al. |
| 2003/0054392 A1 | 3/2003 | Wittig et al. |
| 2003/0170693 A1 | 9/2003 | Chaconas et al. |
| 2003/0235844 A1 | 12/2003 | Slepnev |
| 2004/0023207 A1 | 2/2004 | Polansky |
| 2004/0241651 A1 | 12/2004 | Olek et al. |
| 2007/0190641 A1 | 8/2007 | Wilding et al. |
| 2008/0305142 A1 | 12/2008 | Chen et al. |
| 2008/0305535 A1 | 12/2008 | Auerbach |
| 2010/0055744 A1 | 3/2010 | Nelson et al. |
| 2012/0052560 A1 | 3/2012 | Knight et al. |
| 2014/0308709 A1 | 10/2014 | Kim et al. |

FOREIGN PATENT DOCUMENTS

| | | |
|---|---|---|
| EP | 1176204 A1 | 1/2002 |
| EP | 2692870 A1 | 2/2014 |
| GB | 2332516 A9 | 6/1999 |
| JP | 10234399 A | 9/1998 |
| WO | 199201813 A1 | 2/1992 |
| WO | 199219732 A1 | 11/1992 |

(Continued)

OTHER PUBLICATIONS

Prudhomme, G., 2005, J. Gene Med., vol. 7: pp. 3-17.*

(Continued)

*Primary Examiner* — Michael D Burkhart

(74) *Attorney, Agent, or Firm* — Norton Rose Fulbright US LLP

(57) ABSTRACT

An in vitro process for the production of closed linear deoxyribonucleic acid (DNA) comprises (a) contacting a DNA template comprising at least one protelomerase target sequence with at least one DNA polymerase in the presence of one or more primers under conditions promoting amplification of the template; and (b) contacting amplified DNA produced in (a) with at least one protelomerase under conditions promoting production of closed linear DNA. A kit provides components necessary in the process.

6 Claims, 6 Drawing Sheets

Specification includes a Sequence Listing.

(56) References Cited

FOREIGN PATENT DOCUMENTS

| WO | 199632473 A1 | 10/1996 |
|---|---|---|
| WO | 199719193 A2 | 5/1997 |
| WO | 199821322 A1 | 5/1998 |
| WO | 199918241 A1 | 4/1999 |
| WO | 99/33559 A1 | 7/1999 |
| WO | 00/015779 A2 | 3/2000 |
| WO | 200104280 A2 | 1/2001 |
| WO | 0177384 A2 | 10/2001 |
| WO | 03/035841 A2 | 5/2003 |
| WO | 2004007684 A2 | 1/2004 |
| WO | 2004028562 A2 | 4/2004 |
| WO | 2004074503 A2 | 9/2004 |
| WO | 2005054435 A2 | 6/2005 |
| WO | 2006063355 A2 | 6/2006 |
| WO | 2006108423 A2 | 10/2006 |
| WO | 2006/119066 A2 | 11/2006 |
| WO | 2007087478 A2 | 8/2007 |
| WO | 2008151023 A2 | 12/2008 |
| WO | 2010026099 A1 | 3/2010 |

OTHER PUBLICATIONS

Aihara et al., An interlocked dimer of the prolelomerase TeiK distorts DNA structure for the formation of hairpin telomeres, Mol Cell. Sep. 21, 2007;27(6):901-13.
Bankhead et al., Mixing active-site components: a recipe for the unique enzymatic activity of a telomere resolvase, Proc Nail Acad Sci US A. Sep. 21, 2004;101(38):13768-73. Epub Sep. 13, 2004.
Beyer S, Nickels P, Simmel FC Periodic DNA nanotemplates synthesized by rolling circle amplification Nano Lett Apr. 2005;5(4):719-22.
Blanco, et al.; Highly Efficient DNA Synthesis by the Phage Ø29 DNA Polymerase; The Journal of Biological Chemistry, vol. 264, No. 15, May / Jun. 1989; pp. 8935-8940.
Blasco MA, Blanco L, Pares E, Salas M, Bernad A. Structural and functional analysis of temperature-sensitive mutants of the phage phi 29 DNA polymerase. Nucleic Acids Res. Aug. 25, 1990;18(16)14763-70.
Dean FB, Nelson JR, Giesler TL, Lasken RS. Rapid amplification of plasmid and phage DNA using Phi 29 DNA polymerase and multiply-primed rolling circle amplification. Genome Res. Jun. 2001; 11(6):11095-9.
Deneke et al. Phage N15 telomere resolution. Target requirements for recognition and processing by the protelomerase. J Biol Chem. Mar. 22, 2002; 277(12)110410-9. Epub Jan. 11, 2002.
Deneke et al., "The Protelomerase of Temperate *Escherichia coli* Phage N15 has Cleaving-Joining Activity", PNAS, 2000, 97(14): pp. 7721 to 7726.
Deneke et al., Catalytic residues of the telomere resolvase ResT: a pattern similar to, but distinct from, tyrosine Yecombinases and type IB topoisomerases, J Bioi Chem. Dec. 17, 2004;279(51):53699-706. Epub Oct. 6, 2004.
Ebersole T, Okamoto Y, Noskov VN, Kouprina N, Kim JH, Leem SH, Barrett JC, Masumoto H, Larionov V. Rapid generation of long synthetic tandem repeats and its application for analysis in human artificial chromosome formation. Hucleic Acids Res. Sep. 1, 2005 ;33(15):e130.
Genbank Accession No. 037967—Telomerase (Gp29), (GI: 75078301, Oct. 31, 2006, retrieved on Mar. 21, 2014 from http://www.ncbi.nlm.nih.gov/protein/037967).
Genbank Accession No. 038545—Bacteriophage phi29 temperature sensitive mutant TS2 (98) DNA polymerase gene), (GI:75092995, Oct. 31, 2006, retrieved on Mar. 21, 2014 from http://www.ncbi.nlm.nih.gov/protein/038545).
Genbank Accession No. CAA37450—Bacillus phage phi29 protein, (GI: 15734, submitted by Bemad et al. Jun. 7, 1990, retrieved on Mar. 17, 2014 from http://www.ncbi.nlm.nih.gov/protein/GI:15734).

Genbank Accession No. X53370—Bacteriophage phi29 temperature sensitive mutant TS2(98) DNA polymerase, complete genome (GI: 15733, submitted by Bernad et al. Jun. 7, 1990, retrieved on Mar. 17, 2014 from http://www.ncbi.nlm.nih.gov/nuccore/15733).
Hadig JS, Kool ET. Small circular DNAs for synthesis of the human telomere repeat: varied sizes, structures and telomereencoding activities. Nucleic Acids Res. Nov. 1, 2004; 32(19):e152.
Hartikka J, Sawdey M, Cornefert-Jensen F, Margalith M, Bamhad K, Nolasco M, Vahlsing HL, Meek J, Marquet M, Hobad P, Norman J, Manthorpe M (1996) An improved plasmid DNA expression vector for direct injection into skeletal muscle. Hum Gene Ther 7:1205-1217.
Heinrich et al., "Linear closed mini DNA generated by the prokaryotic cleaving-joining enzyme TeIN is functional in mammalian cells", J. Mol. Med, 2002, 80: pp. 648 to 654.
Hedwig S, Klein I, Lurz R, Lanka E, Appel B. PY54, a linear plasmid prophage of Yersinia enterocolitica with covalently closed ends. Mol Microbiol. May 2003; 48(4):989-1003.
Hedwig, S. Linear plasmids and prophages in Gram-negative bacteria. Microbial Linear Plasmids Springer Berlin Heidelberg 2007:pp. 141-162.
Huang et al., "Protelomerase Uses a Topoisomerase IB/Y-Recombinase Type Mechanism to Generate DNA Hairpin Ends", Journal of Molecular Biology, 2004, 337(1): pp. 77 to 86.
Hutchison et al. Cell-free cloning using cp29 DNA polymerase. Proceedings of the National Academy of Sciences of the United States of America. 2005. 102(48): 17332-17336.
India Intellectual Property Examination Report; Application No. 1671/CHENP/2013; Feb. 19, 2018.
Inoue et al., Improvements of rolling circle amplification (RCA) efficiency and accuracy using Thermus Thermophilus SSB mutant protein, Nuc. Acids Res. 2006, vol. 34, No. 9.
Konopa G, Baranska S, Wegrzyn A, Wegrzyn G. Bacteriophage and host mutants causing the rolling-circle lambda DNA replication early after infection FEBS Lett Apr. 28, 2000; 472(2-3):217-20.
Kuhn et al., High-purity preparation of a large DNA dumbbell, Antisense Nucleic Acid Drug Dev. Jun. 2001;11(3):149-53.
Leutenegger, C.M., et al., Immunization of Cats against Feline Immunodeficiency Virus (FIV) Infection by Using 3 Minimalistic Immunogenic Defined Gene Expression Vector Vaccines Expressing FIV gp140 Alone or with Feline nterleukin-1 (1L 12), IL-16, or a CpG Motif, Journal of Virology, vol. 74, pp. 10477-10457, Nov. 2000.
Lin C, Xie M, Chen JJ, Liu Y, Yan H. Rolling-circle amplification of a DNA nanojunction. Angew Chem Int Ed Engl., Nov. 20, 2006; 45(45):7537-9.
Liu et al., Rolling Circle DNA Synthesis:? Small Circular Oligonucleotides as Efficient Templates for DNA Polymerases, J. Am Chem. Soc , 1996, 118 (7), pp. 1587-1594.
Mardanov & Navin, "Conversion of Linear DNA with Hairpin Telmeres into a Circular Molecule in the Course of Phage N15 Lytic Replication", J Mol Biol., (2009) 391, 261-268.
Mardanov et al., "Functional characterization of the repA replication gene of linear plasmid prophage N15", J. Resmic., (2006), 157(2): pp. 176-183.
Meinhardt et al., Microbial linear plasm ids, Appl Microbiol Biotechnol. Apr. 1997;47(4):329-36.
Mobberley JM, Authement RN, Segall AM, Paul JH. The temperate marine phage PhiHAP-1 of Halomonas aquamarina possesses a linear plasmid-like prophage genome J Virol Jul. 2008; 82(13):6618-30 Epub Apr. 30, 2008.
Moreno et al., "DNA immunization with minimalistic expression constructs," Vaccine, 2004, 22: 1709-1716.
Nosek J, Rycovska A, Makhov AM, Griffith JD, Tomaska L. Amplification of telomeric arrays via rolling-circle mechanism. J Biol Chem. Mar. 18, 2005; 280(11): 10840-5. Epub Jan. 18, 2005.
Nosek, et al., "Amplifiction of Telomeric Arrays via Rolling-circle Mechanism", Journal of Biological Chemistry, vol. 280, No. 11, pp. 10840-10845; published Jan. 18, 2005.
Office Action issued in Japanese Application No. 2016-202277, dated Sep. 5, 2017.
Ooi et al., Recombineering linear DNA that replicate stably in *E. coli*, Plasmid. Jan. 2008;59(1):63-71. Epub Nov. 7, 2007.

(56) References Cited

OTHER PUBLICATIONS

Promega manual on pGL4.13 [luc2/SV40] revised Oct. 2013; recovered from http://www.promega.com/protocols on Sep. 26, 2016.
Ravin et al., "Genomic sequence and analysis of the atypical temperate bacteriophage N15", Journal of Molecular Biology, May 26, 2000, 299(1): pp. 53 to 73.
Ravin et al., "The protelomerase of the phage-plasmid N15 is responsible for its maintenance in linear form", Journal of Molecular Biology, 2001, 312(5): pp. 899 to 905.
Ravin et al., Mechanisms of replication and telomere resolution of the linear plasmid prophage N15, Fems Microbiol Lett. Apr. 11, 2003;221(1):1-6.
Ravin NV. N15: the linear phage-plasmid. Plasmid. Mar. 2011; 65(2):102-9. Epub Dec. 23, 2010.
Robinson HL, Pertmer TM. Nucleic acid immunizations. CurrProtoc Immunol. 1998. Chapter 2: Unit 2.14. p. 2.14.1-2.14.19. Review.
Rogriguez, E.G., "Nonviral DNA vectors for immunization and therapy: deisgn and methods for their obtention", J. Mol. Med; vol. 82, No. 8, pp. 500-509, Aug. 1, 2004.
Rybchin et al.. The plasmid prophage N15: a linear DNA with covalently closed ends, Mol Microbiol. Sep. 1999;33(5):895-903.
Schirmbeck R, Konig-Merediz SA, Riedl P, Kwissa M, Sack F, Schroff M, Junghans C, Reimann J, Wittig B. Priming of mmune responses to hepatitis B surface antigen with minimal DNA expression constructs modified with a nuclear localization signal peptide. J Mol Med (Berl). Jun. 2001; 79(5-6):343-50.
Schmeer, et al.; "Production of Plasmid DNA as Pharmaceutical"; Chapter 17, Gene Therapy of Solids Cancers Methods and Protogols, Methods in Molecular Blolby, Vo. 1317, DOI 10.1007/978-1-4939-2727-2_17; (Proof—Nov. 2, 2017) Springer Science+Business Media—New York 2015.
Statement of Neil Porter; Executive Head of Research and Development—Touchlight Genetics Limited.; 2015-175262 (Proof—Nov. 2, 2017).
Svarchevsky, et al.; Bacteriophage N15 telomerase (teIN) and secondary immunity repressor (cA) genes, complete cds; National Center for Biotechnology Information; nucleotide database; https://www.ncbi.nlm.nih.gov/nuccore/U63086.1.
Tourand et al., Differential Telomere Processing by Borrelia Telomere Resolvases In Vitro but Not In Vivo, J Bacteriol. Nov. 2006; 188(21): 7378-7386.
Xiao Le-Yi, et al., "Principle and Application of Rolling Circlie DNA Amplification" China Biotechnology, vol. 24, No. 9, pp. 33-38.
Zabala, B., Hammerl, J.A., Espejo, R.T., Hertwig, S., 2009. The linear plasmid prophage Vp58.5 of Vibrio parahaemolyticus is closely related to the integrating phage VHML and constitutes a new incompatibility group of elomere phages. J. Virol. 83, 9313-9320.
Masamune & Richardson, Journal of Biological Chemistry 246(8) 2692-2701, 1971.
Alberts, B. et al., "The structure and Function of DNA", Molecular Biology of the Cell, 4th Edition, Garland Science, 2002, extract.
Murakami et al., Nucleic Acid Research, 2009, 37(3) e19.
Melson and McClelland, Nucleic Acids Research, vol. 29, Supplement, 2045-2071, 1991.
Roberts R. J. et al., "Recognition sequence of specific endonuclease BamHI from Bacillus amyloliquefaciens H", Nature , 1977, 265, 82-84.
Sambrook, J. and Russell, DW "Molecular Cloning: A Laboratory Manual", Chapter 1, "Plasmids and their usefulness n molecular cloning", and Chapter 13, "Mutagenesis", Cold Spring Harbor, 3rd Ed., 2001.
Voineagu etal, Replication stalling at unstable inverted repeats: Interplay between DNA hairpins and fork stabilizing proteins, Proc Natl Acad Sci USA. Jul. 22, 2008; 105(29): 9936-9941.
Zain and Roberts,"A new specific endonuclease from Xanthomonas badrii", J Mol Biol., Sep. 15, 1977;115(2):249-55.

* cited by examiner

A.

B.

C.

SEQUENCE LISTING

<160> NUMBER OF SEQ ID NOS: 42

<210> SEQ ID NO 1
<211> LENGTH: 1728
<212> TYPE: DNA
<213> ORGANISM: Artificial Sequence
<220> FEATURE:
<223> OTHER INFORMATION: Bacillus bacteriophage phi29 DNA polymerase
      nucleic acid sequence

<400> SEQUENCE: 1

```
atgaagcata tgccgagaaa gatgtatagt tgtgactttg agacaactac taaagtggaa      60
gactgtaggg tatgggcgta tggttatatg aatatagaag atcacagtga gtacaaaata     120
ggtaatagcc tggatgagtt tatggcgtgg gtgttgaagg tacaagctga tctatatttc     180
cataacctca aatttgacgg agcttttatc attaactggt tggaacgtaa tggttttaag     240
tggtcggctg acggattgcc aaacacatat aatacgatca tatctcgcat gggacaatgg     300
tacatgattg atatatgttt aggctacaaa gggaaacgta agatacatac agtgatatat     360
gacagcttaa agaaactacc gtttcctgtt aagaagatac taaagacttt aaaactaact     420
gttcttaaag gtgatattga ttaccacaaa gaaagaccag tcggctataa gataacaccc     480
gaagaatacg cctatattaa aaacgatatt cagattattg cggaacgtct gttaattcag     540
tttaagcaag gtttagaccg gatgacagca ggcagtgaca gtctaaaagg tttcaaggat     600
attataacca ctaagaaatt caaaaaggtg tttcctacat tgagtcttgg actcgataag     660
gaagtgagat acgcctatag aggtggtttt acatggttaa atgataggtt caaagaaaaa     720
gaaatcggag aaggcatggt cttcgatgtt aatagtctat atcctgcaca gatgtatagc     780
cgtctccttc catatggtga acctatagta ttcgaggyta atacgtttg ggacgaagat     840
tacccactac acatacagca tatcagatgt gagttcgaat tgaaagaggg ctatatacccc     900
actatacaga taaaaagaag taggtttat aaaggtaatg agtacctaaa aagtagcggc     960
ggggagatag ccgacctctg gttgtcaaat gtagacctag aattaatgaa agaacactac    1020
gatttatata acgttgaata tatcagcggc ttaaaattta aagcaactac aggtttgttt    1080
aaagattta tagataaatg gacgtacatc aagacgacat cagaaggagc gatcaagcaa    1140
ctagcaaaac tgatgttaaa cagtctatac ggtaaattcg ctagtaaccc tgatgttaca    1200
gggaaagtcc cttatttaaa agagaatggg cgctaggtt tcagacttgg agaagaggaa    1260
acaaaagacc ctgtttatac acctatgggc gttttcatca ctgcatgggc tagatacacg    1320
acaattacag cggcacaggc ttgttatgat cggataatat actgtgatac tgacagcata    1380
catttaacgg gtacagagat acctgatgta ataaaagata tagttgaccc taagaaattg    1440
ggatactggg cacatgaaag tacattcaaa agagttaaat atctgagaca agagaccttat    1500
atacaagaca tctatatgaa agaagtagat ggtaagttag tagaaggtag tccagatgat    1560
tacactgata taaaatttag tgttaaatgt gcgggaatga ctgacaagat taagaaagag    1620
gttacgtttg agaattcaa agtcggattc agtcggaaaa tgaagcctaa gcctgtgcaa    1680
gtgccgggcg gggtggttct ggttgatgac acattcacaa tcaaataa                1728
```

<210> SEQ ID NO 2
<211> LENGTH: 575
<212> TYPE: PRT
<213> ORGANISM: Artificial Sequence
<220> FEATURE:
<223> OTHER INFORMATION: Bacillus bacteriophage phi29 DNA polymerase
      amino acid sequence

<400> SEQUENCE: 2

```
Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
    130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ala Glu Arg
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Tyr
    210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
    290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
        355                 360                 365

Tyr Ile Lys Thr Thr Ser Glu Gly Ala Ile Lys Gln Leu Ala Lys Leu
    370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
```

```
                        405                 410                 415
Gly Glu Glu Thr Lys Asp Pro Val Tyr Thr Pro Met Gly Val Phe
                420                 425                 430

Ile Thr Ala Trp Ala Arg Tyr Thr Thr Ile Thr Ala Ala Gln Ala Cys
            435                 440                 445

Tyr Asp Arg Ile Ile Tyr Cys Asp Thr Asp Ser Ile His Leu Thr Gly
        450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Val Lys Tyr Leu Arg
                485                 490                 495

Gln Lys Thr Tyr Ile Gln Asp Ile Tyr Met Lys Glu Val Asp Gly Lys
                500                 505                 510

Leu Val Glu Gly Ser Pro Asp Asp Tyr Thr Asp Ile Lys Phe Ser Val
                515                 520                 525

Lys Cys Ala Gly Met Thr Asp Lys Ile Lys Glu Val Thr Phe Glu
            530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys
                565                 570                 575

<210> SEQ ID NO 3
<211> LENGTH: 775
<212> TYPE: PRT
<213> ORGANISM: Artificial Sequence
<220> FEATURE:
<223> OTHER INFORMATION: Pyrococcus sp Deep Vent DNA polymerase amino
      acid sequence

<400> SEQUENCE: 3

Met Ile Leu Asp Ala Asp Tyr Ile Thr Glu Asp Gly Lys Pro Ile Ile
1               5                   10                  15

Arg Ile Phe Lys Lys Glu Asn Gly Glu Phe Lys Val Glu Tyr Asp Arg
            20                  25                  30

Asn Phe Arg Pro Tyr Ile Tyr Ala Leu Leu Lys Asp Asp Ser Gln Ile
        35                  40                  45

Asp Glu Val Arg Lys Ile Thr Ala Glu Arg His Gly Lys Ile Val Arg
    50                  55                  60

Ile Ile Asp Ala Glu Lys Val Arg Lys Lys Phe Leu Gly Arg Pro Ile
65                  70                  75                  80

Glu Val Trp Arg Leu Tyr Phe Glu His Pro Gln Asp Val Pro Ala Ile
                85                  90                  95

Arg Asp Lys Ile Arg Glu His Ser Ala Val Ile Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
    130                 135                 140

Leu Tyr His Glu Gly Glu Glu Phe Ala Lys Gly Pro Ile Ile Met Ile
145                 150                 155                 160

Ser Tyr Ala Asp Glu Glu Glu Ala Lys Val Ile Thr Trp Lys Lys Ile
                165                 170                 175

Asp Leu Pro Tyr Val Glu Val Val Ser Ser Glu Arg Glu Met Ile Lys
            180                 185                 190
```

```
Arg Phe Leu Lys Val Ile Arg Glu Lys Asp Pro Asp Val Ile Ile Thr
            195                 200                 205
Tyr Asn Gly Asp Ser Phe Asp Leu Pro Tyr Leu Val Lys Arg Ala Glu
210                 215                 220
Lys Leu Gly Ile Lys Leu Pro Leu Gly Arg Asp Gly Ser Glu Pro Lys
225                 230                 235                 240
Met Gln Arg Leu Gly Asp Met Thr Ala Val Glu Ile Lys Gly Arg Ile
                245                 250                 255
His Phe Asp Leu Tyr His Val Ile Arg Arg Thr Ile Asn Leu Pro Thr
            260                 265                 270
Tyr Thr Leu Glu Ala Val Tyr Glu Ala Ile Phe Gly Lys Pro Lys Glu
        275                 280                 285
Lys Val Tyr Ala His Glu Ile Ala Glu Ala Trp Glu Thr Gly Lys Gly
    290                 295                 300
Leu Glu Arg Val Ala Lys Tyr Ser Met Glu Asp Ala Lys Val Thr Tyr
305                 310                 315                 320
Glu Leu Gly Arg Glu Phe Phe Pro Met Glu Ala Gln Leu Ser Arg Leu
                325                 330                 335
Val Gly Gln Pro Leu Trp Asp Val Ser Arg Ser Ser Thr Gly Asn Leu
            340                 345                 350
Val Glu Trp Tyr Leu Leu Arg Lys Ala Tyr Glu Arg Asn Glu Leu Ala
        355                 360                 365
Pro Asn Lys Pro Asp Glu Arg Glu Tyr Glu Arg Arg Leu Arg Glu Ser
    370                 375                 380
Tyr Ala Gly Gly Tyr Val Lys Glu Pro Glu Lys Gly Leu Trp Glu Gly
385                 390                 395                 400
Leu Val Ser Leu Asp Phe Arg Ser Leu Tyr Pro Ser Ile Ile Ile Thr
                405                 410                 415
His Asn Val Ser Pro Asp Thr Leu Asn Arg Glu Gly Cys Arg Glu Tyr
            420                 425                 430
Asp Val Ala Pro Glu Val Gly His Lys Phe Cys Lys Asp Phe Pro Gly
        435                 440                 445
Phe Ile Pro Ser Leu Leu Lys Arg Leu Leu Asp Glu Arg Gln Glu Ile
    450                 455                 460
Lys Arg Lys Met Lys Ala Ser Lys Asp Pro Ile Glu Lys Lys Met Leu
465                 470                 475                 480
Asp Tyr Arg Gln Arg Ala Ile Lys Ile Leu Ala Asn Ser Tyr Tyr Gly
                485                 490                 495
Tyr Tyr Gly Tyr Ala Lys Ala Arg Trp Tyr Cys Lys Glu Cys Ala Glu
            500                 505                 510
Ser Val Thr Ala Trp Gly Arg Glu Tyr Ile Glu Phe Val Arg Lys Glu
        515                 520                 525
Leu Glu Glu Lys Phe Gly Phe Lys Val Leu Tyr Ile Asp Thr Asp Gly
    530                 535                 540
Leu Tyr Ala Thr Ile Pro Gly Ala Lys Pro Glu Glu Ile Lys Lys Lys
545                 550                 555                 560
Ala Leu Glu Phe Val Asp Tyr Ile Asn Ala Lys Leu Pro Gly Leu Leu
                565                 570                 575
Glu Leu Glu Tyr Glu Gly Phe Tyr Val Arg Gly Phe Phe Val Thr Lys
            580                 585                 590
Lys Lys Tyr Ala Leu Ile Asp Glu Glu Gly Lys Ile Ile Thr Arg Gly
        595                 600                 605
Leu Glu Ile Val Arg Arg Asp Trp Ser Glu Ile Ala Lys Glu Thr Gln
```

```
                       610                 615                 620

Ala Lys Val Leu Glu Ala Ile Leu Lys His Gly Asn Val Glu Glu Ala
625                 630                 635                 640

Val Lys Ile Val Lys Glu Val Thr Glu Lys Leu Ser Lys Tyr Glu Ile
                645                 650                 655

Pro Pro Glu Lys Leu Val Ile Tyr Glu Gln Ile Thr Arg Pro Leu His
                660                 665                 670

Glu Tyr Lys Ala Ile Gly Pro His Val Ala Val Ala Lys Arg Leu Ala
            675                 680                 685

Ala Arg Gly Val Lys Val Arg Pro Gly Met Val Ile Gly Tyr Ile Val
        690                 695                 700

Leu Arg Gly Asp Gly Pro Ile Ser Lys Arg Ala Ile Leu Ala Glu Glu
705                 710                 715                 720

Phe Asp Leu Arg Lys His Lys Tyr Asp Ala Glu Tyr Tyr Ile Glu Asn
                725                 730                 735

Gln Val Leu Pro Ala Val Leu Arg Ile Leu Glu Ala Phe Gly Tyr Arg
                740                 745                 750

Lys Glu Asp Leu Arg Trp Gln Lys Thr Lys Gln Thr Gly Leu Thr Ala
            755                 760                 765

Trp Leu Asn Ile Lys Lys Lys
        770                 775

<210> SEQ ID NO 4
<211> LENGTH: 2631
<212> TYPE: DNA
<213> ORGANISM: Artificial Sequence
<220> FEATURE:
<223> OTHER INFORMATION: Bacillus stearothermophilus DNA polymerase I
      (polA) nucleic acid sequence

<400> SEQUENCE: 4
atgaagaaga agctagtact aattgatggc aacagtgtgg cataccgcgc cttttttgcc      60
ttgccacttt tgcataacga caaaggcatt catacgaatg cggtttacgg gtttacgatg     120
atgttgaaca aaattttggc ggaagaacaa ccgacccatt tacttgtagc gtttgacgcc     180
ggaaaaacga cgttccggca tgaaacgttt caagagtata aggcggacg gcaacaaact     240 cccccggaac tgtccgagca gtttccgctg ttgcgcgagc tattaaaagc gtaccgcatt     300
cccgcttatg aacttgatca ttacgaagcg acgatatta tcgggacgct cgctgcccgc     360
gctgagcaag aagggtttga agtgaaaatc atttccggcg accgcgattt aacccagctc     420
gcctcccgtc atgtgacggt cgatattacg aaaaaaggga ttaccgacat tgagccgtat     480
acgccagaga ccgttcgcga aaaatacggc ctgactccgg agcaaatagt ggatttaaaa     540
ggattgatgg gcgataaatc cgacaacatc ccgggcgtgc ccggcatcgg gaaaaaacg      600 gcggtcaagc tgctgaagca atttggtacg gtggaaaatg tgctcgcatc gattgatgag     660 gtgaagggg aaaaactgaa agaaaacttg cgccaacacc gggatttagc tctcttgagc     720
aaacagctgg cgtccatttg ccgcgacgcc ccggttgagc tgtcgttaga tgacattgtc     780
tacgaaggac aagaccgcga aaagtcatc gcgttattta agaactcgg gtttcagtcg     840 ttcttggaaa aatggccgc gccggcagcc gaagggagaa accgcttga ggagatggag     900 tttgccatcg ttgacgtcat taccgaagag atgcttgccg acaaggcagc gcttgtcgtt     960
gaggtgatga agaaaactga ccacgatgcc ccgattgtcg aatcgcact agtgaacgag    1020 catgggcgat tttttatgcg cccggagacc gcgctggctg attcgcaatt tttagcatgg    1080
```

```
cttgccgatg aaacgaagaa aaaaagcatg tttgacgcca agcgggcagt cgttgcctta    1140
aagtggaaag gaattgagct tcgcggcgtc gcctttgatt tattgctcgc tgcctatttg    1200
ctcaatccgg ctcaagatgc cggcgatatc gctgcggtgg cgaaaatgaa acaatatgaa    1260
gcggtgcggt cggatgaagc ggtctatggc aaaggcgtca agcggtcgct gccggacgaa    1320
cagacgcttg ctgagcatct cgttcgcaaa gcggcagcca tttgggcgct tgagcagccg    1380
tttatggacg atttgcggaa caacgaacaa gatcaattat taacgaagct tgagcagccg    1440
ctggcggcga ttttggctga aatggaattc actggggtga acgtggatac aaagcggctt    1500
gaacagatgg ttcggagct cgccgaacaa ctgcgtgcca tcgagcagcg catttacgag    1560
ctagccggcc aagagttcaa cattaactca ccaaaacagc tcggagtcat tttatttgaa    1620
aagctgcagc taccggtgct gaagaagacg aaaacaggct attcgacttc ggctgatgtg    1680
cttgagaagc ttgcgccgca tcatgaaatc gtcgaaaaca ttttgcatta ccgccagctt    1740
ggcaaactgc aatcaacgta tattgaagga ttgttgaaag ttgtgcgccc tgataccggc    1800
aaagtgcata cgatgttcaa ccaagcgctg acgcaaactg gcggctcag ctcggccgag    1860
ccgaacttgc aaaacattcc gattcggctc gaagaggggc ggaaaatccg ccaagcgttc    1920
gtcccgtcag agccggactg gctcattttc gccgccgatt actcacaaat tgaattgcgc    1980
gtcctcgccc atatcgccga tgacgacaat ctaattgaag cgttccaacg cgatttggat    2040
attcacacaa aaacggcgat ggacatttt catgtgagcg aagaggaagt cacggccaac    2100
atgcgccgcc aggcaaaggc cgttaacttc ggtatcgttt acggaattag cgattacgga    2160
ttggcgcaaa acttgaacat tacgcgcaaa gaagctgccg aatttatcga cgttacttc    2220
gccagctttc cgggcgtaaa gcagtatatg gaaaacattg tgcaagaagc gaaacagaaa    2280
ggatatgtga caacgctgtt gcatcggcgc cgctatttgc ctgatattac aagccgcaat    2340
ttcaacgtcc gcagttttgc agagcggacg gccatgaaca cgccaattca aggaagcgcc    2400
gctgacatta ttaaaaaagc gatgattgat ttagcggcac ggctgaaaga agagcagctt    2460
caggctcgtc ttttgctgca agtgcatgac gagctcattt tggaagcgcc aaaagaggaa    2520
attgagcgat tatgtgagct tgttccggaa gtgatggagc aggccgttac gctccgcgtg    2580
ccgctgaaag tcgactacca ttacggccca acatggtatg atgccaaata a            2631
```

<210> SEQ ID NO 5
<211> LENGTH: 876
<212> TYPE: PRT
<213> ORGANISM: Artificial Sequence
<220> FEATURE:
<223> OTHER INFORMATION: Bacillus stearothermophilus DNA polymerase I
      (polA) amino acid sequence

<400> SEQUENCE: 5

Met Lys Lys Lys Leu Val Leu Ile Asp Gly Asn Ser Val Ala Tyr Arg
1               5                   10                  15

Ala Phe Phe Ala Leu Pro Leu Leu His Asn Asp Lys Gly Ile His Thr
            20                  25                  30

Asn Ala Val Tyr Gly Phe Thr Met Met Leu Asn Lys Ile Leu Ala Glu
        35                  40                  45

Glu Gln Pro Thr His Leu Leu Val Ala Phe Asp Ala Gly Lys Thr Thr
    50                  55                  60

Phe Arg His Glu Thr Phe Gln Glu Tyr Lys Gly Gly Arg Gln Gln Thr
65                  70                  75                  80

Pro Pro Glu Leu Ser Glu Gln Phe Pro Leu Leu Arg Glu Leu Leu Lys

-continued

```
                    85                  90                  95
Ala Tyr Arg Ile Pro Ala Tyr Glu Leu Asp His Tyr Glu Ala Asp Asp
                100                 105                 110

Ile Ile Gly Thr Leu Ala Ala Arg Ala Glu Gln Glu Gly Phe Glu Val
            115                 120                 125

Lys Ile Ile Ser Gly Asp Arg Asp Leu Thr Gln Leu Ala Ser Arg His
        130                 135                 140

Val Thr Val Asp Ile Thr Lys Lys Gly Ile Thr Asp Ile Glu Pro Tyr
145                 150                 155                 160

Thr Pro Glu Thr Val Arg Glu Lys Tyr Gly Leu Thr Pro Glu Gln Ile
                165                 170                 175

Val Asp Leu Lys Gly Leu Met Gly Asp Lys Ser Asp Asn Ile Pro Gly
            180                 185                 190

Val Pro Gly Ile Gly Glu Lys Thr Ala Val Lys Leu Leu Lys Gln Phe
        195                 200                 205

Gly Thr Val Glu Asn Val Leu Ala Ser Ile Asp Glu Val Lys Gly Glu
    210                 215                 220

Lys Leu Lys Glu Asn Leu Arg Gln His Arg Asp Leu Ala Leu Leu Ser
225                 230                 235                 240

Lys Gln Leu Ala Ser Ile Cys Arg Asp Ala Pro Val Glu Leu Ser Leu
                245                 250                 255

Asp Asp Ile Val Tyr Glu Gly Gln Asp Arg Glu Lys Val Ile Ala Leu
            260                 265                 270

Phe Lys Glu Leu Gly Phe Gln Ser Phe Leu Glu Lys Met Ala Ala Pro
        275                 280                 285

Ala Ala Glu Gly Glu Lys Pro Leu Glu Glu Met Glu Phe Ala Ile Val
    290                 295                 300

Asp Val Ile Thr Glu Glu Met Leu Ala Asp Lys Ala Ala Leu Val Val
305                 310                 315                 320

Glu Val Met Glu Glu Asn Tyr His Asp Ala Pro Ile Val Gly Ile Ala
                325                 330                 335

Leu Val Asn Glu His Gly Arg Phe Phe Met Arg Pro Glu Thr Ala Leu
            340                 345                 350

Ala Asp Ser Gln Phe Leu Ala Trp Leu Ala Asp Glu Thr Lys Lys Lys
        355                 360                 365

Ser Met Phe Asp Ala Lys Arg Ala Val Val Ala Leu Lys Trp Lys Gly
    370                 375                 380

Ile Glu Leu Arg Gly Val Ala Phe Asp Leu Leu Leu Ala Ala Tyr Leu
385                 390                 395                 400

Leu Asn Pro Ala Gln Asp Ala Gly Asp Ile Ala Ala Val Ala Lys Met
                405                 410                 415

Lys Gln Tyr Glu Ala Val Arg Ser Asp Glu Ala Val Tyr Gly Lys Gly
            420                 425                 430

Val Lys Arg Ser Leu Pro Asp Glu Gln Thr Leu Ala Glu His Leu Val
        435                 440                 445

Arg Lys Ala Ala Ala Ile Trp Ala Leu Glu Gln Pro Phe Met Asp Asp
    450                 455                 460

Leu Arg Asn Asn Glu Gln Asp Gln Leu Leu Thr Lys Leu Glu Gln Pro
465                 470                 475                 480

Leu Ala Ala Ile Leu Ala Glu Met Glu Phe Thr Gly Val Asn Val Asp
                485                 490                 495

Thr Lys Arg Leu Glu Gln Met Gly Ser Glu Leu Ala Glu Gln Leu Arg
            500                 505                 510
```

Ala Ile Glu Gln Arg Ile Tyr Glu Leu Ala Gly Gln Glu Phe Asn Ile
    515                 520                 525

Asn Ser Pro Lys Gln Leu Gly Val Ile Leu Phe Glu Lys Leu Gln Leu
530                 535                 540

Pro Val Leu Lys Lys Thr Lys Thr Gly Tyr Ser Thr Ala Asp Val
545                 550                 555                 560

Leu Glu Lys Leu Ala Pro His His Glu Ile Val Glu Asn Ile Leu His
                565                 570                 575

Tyr Arg Gln Leu Gly Lys Leu Gln Ser Thr Tyr Ile Glu Gly Leu Leu
                580                 585                 590

Lys Val Val Arg Pro Asp Thr Gly Lys Val His Thr Met Phe Asn Gln
                595                 600                 605

Ala Leu Thr Gln Thr Gly Arg Leu Ser Ser Ala Glu Pro Asn Leu Gln
                610                 615                 620

Asn Ile Pro Ile Arg Leu Glu Glu Gly Arg Lys Ile Arg Gln Ala Phe
625                 630                 635                 640

Val Pro Ser Glu Pro Asp Trp Leu Ile Phe Ala Ala Asp Tyr Ser Gln
                645                 650                 655

Ile Glu Leu Arg Val Leu Ala His Ile Ala Asp Asp Asp Asn Leu Ile
                660                 665                 670

Glu Ala Phe Gln Arg Asp Leu Asp Ile His Thr Lys Thr Ala Met Asp
                675                 680                 685

Ile Phe His Val Ser Glu Glu Glu Val Thr Ala Asn Met Arg Arg Gln
                690                 695                 700

Ala Lys Ala Val Asn Phe Gly Ile Val Tyr Gly Ile Ser Asp Tyr Gly
705                 710                 715                 720

Leu Ala Gln Asn Leu Asn Ile Thr Arg Lys Glu Ala Ala Glu Phe Ile
                725                 730                 735

Glu Arg Tyr Phe Ala Ser Phe Pro Gly Val Lys Gln Tyr Met Glu Asn
                740                 745                 750

Ile Val Gln Glu Ala Lys Gln Lys Gly Tyr Val Thr Thr Leu Leu His
                755                 760                 765

Arg Arg Arg Tyr Leu Pro Asp Ile Thr Ser Arg Asn Phe Asn Val Arg
770                 775                 780

Ser Phe Ala Glu Arg Thr Ala Met Asn Thr Pro Ile Gln Gly Ser Ala
785                 790                 795                 800

Ala Asp Ile Ile Lys Lys Ala Met Ile Asp Leu Ala Ala Arg Leu Lys
                805                 810                 815

Glu Glu Gln Leu Gln Ala Arg Leu Leu Leu Gln Val His Asp Glu Leu
                820                 825                 830

Ile Leu Glu Ala Pro Lys Glu Glu Ile Glu Arg Leu Cys Glu Leu Val
                835                 840                 845

Pro Glu Val Met Glu Gln Ala Val Thr Leu Arg Val Pro Leu Lys Val
850                 855                 860

Asp Tyr His Tyr Gly Pro Thr Trp Tyr Asp Ala Lys
865                 870                 875

<210> SEQ ID NO 6
<211> LENGTH: 1563
<212> TYPE: DNA
<213> ORGANISM: Artificial Sequence
<220> FEATURE:
<223> OTHER INFORMATION: Halomonas phage phiHAP-1 protelomerase nucleic
    acid sequence

<400> SEQUENCE: 6

```
atgagcggtg agtcacgtag aaaggtcgat ttagcggaat tgatagagtg gttgctcagc      60
gagatcaaag agatcgacgc cgatgatgag atgccacgta aagagaaaac caagcgcatg     120
gcgcggctgg cacgtagctt caaaacgcgc ctgcatgatg acaagcgccg caaggattct     180
gagcggatcg cggtcacgac ctttcgccgc tacatgacag aagcgcgcaa ggcggtgact     240
gcgcagaact ggcgccatca cagcttcgac cagcagatcg agcggctggc cagccgctac     300
ccggcttatg ccagcaagct ggaagcgctc ggcaagctga ccgatatcag cgccattcgt     360
atggcccacc gcgagctgct cgaccagatc cgcaacgatg acgacgctta tgaggacatc     420
cgggcgatga agctggacca tgaaatcatg cgccacctga cgttgagctc tgcacagaaa     480
agcacgctgg ctgaagaggc cagcgagacg ctggaagagc gcgcggtgaa cacggtcgag     540
atcaactacc actggttgat ggagacggtt tacgagctgc tgagtaaccg ggagagaatg     600
gtcgatgggg agtatcgcgg ctttttcagt tacctagcgc ttgggctggc gctggccacc     660
gggcgtcgct cgatcgaggt gctgaagacc ggacggatca cgaaggtggg cgagtatgag     720
ctggagttca gcggccaggc gaaaaagcgc ggcggcgtcg actatagcga ggcttaccac     780
atttatatccc tggtgaaagc tgacctggtg atcgaagcgt gggatgagct tcgctcgctg     840
ccggaagctg ctgagctgca gggcatggac aacagcgatg tgaaccgccg cacggcgaag     900
acgctcaaca cgctcactaa gcggatcttt aacaacgatg agcgcgtttt caaggacagc     960
cgggcgatct gggcgcggct ggtgtttgag ctgcacttct cgcgcgacaa gcgctggaag    1020
aaagtcaccg aggacgtgtt ctggcgtgag atgctgggc atgaggacat ggatacacag    1080
cgcagctacc gcgcctttaa aatcgactac gacgagccgg atcaagccga ccaggaagat    1140
tacgaacacg ctagccgcct cgccgcgctg caggcgctgg acggccatga gcagcttgag    1200
agcagcgacg cccaggcgcg tgtgcatgcc tgggtgaaag cgcagatcga gcaggagcct    1260
gacgcgaaaa ttacgcagtc tctgatcagc cgggagctgg gcgtttatcg ccctgccata    1320
aaagcgtacc tggagctggc gcgagaggcg ctcgacgcgc gaacgtcga tctggacaag    1380
gtcgcggcgg cagtgccgaa ggaagtagcc gaggcgaagc cccggctgaa cgcccaccca    1440
caagggggatg caggtgggt cggggtggct tcaatcaacg gggtggaagt tgcacgggtg    1500
ggcaaccagg caggccggat cgaagcgatg aaagcggcct ataaagcggc gggtgggcgc    1560
tga                                                                   1563
```

<210> SEQ ID NO 7
<211> LENGTH: 520
<212> TYPE: PRT
<213> ORGANISM: Artificial Sequence
<220> FEATURE:
<223> OTHER INFORMATION: Halomonas phage phiHAP-1 protelomerase amino
      acid sequence

<400> SEQUENCE: 7

```
Met Ser Gly Glu Ser Arg Arg Lys Val Asp Leu Ala Glu Leu Ile Glu
1               5                   10                  15

Trp Leu Ser Glu Ile Lys Glu Ile Asp Ala Asp Asp Glu Met Pro
            20                  25                  30

Arg Lys Glu Lys Thr Lys Arg Met Ala Arg Leu Ala Arg Ser Phe Lys
        35                  40                  45

Thr Arg Leu His Asp Asp Lys Arg Arg Lys Asp Ser Glu Arg Ile Ala
    50                  55                  60
```

Val Thr Thr Phe Arg Arg Tyr Met Thr Glu Ala Arg Lys Ala Val Thr
 65                  70                  75                  80

Ala Gln Asn Trp Arg His His Ser Phe Asp Gln Gln Ile Glu Arg Leu
                 85                  90                  95

Ala Ser Arg Tyr Pro Ala Tyr Ala Ser Lys Leu Glu Ala Leu Gly Lys
            100                 105                 110

Leu Thr Asp Ile Ser Ala Ile Arg Met Ala His Arg Glu Leu Leu Asp
        115                 120                 125

Gln Ile Arg Asn Asp Asp Ala Tyr Glu Asp Ile Arg Ala Met Lys
130                 135                 140

Leu Asp His Glu Ile Met Arg His Leu Thr Leu Ser Ser Ala Gln Lys
145                 150                 155                 160

Ser Thr Leu Ala Glu Glu Ala Ser Glu Thr Leu Glu Glu Arg Ala Val
                165                 170                 175

Asn Thr Val Glu Ile Asn Tyr His Trp Leu Met Glu Thr Val Tyr Glu
            180                 185                 190

Leu Leu Ser Asn Arg Glu Arg Met Val Asp Gly Glu Tyr Arg Gly Phe
        195                 200                 205

Phe Ser Tyr Leu Ala Leu Gly Leu Ala Leu Ala Thr Gly Arg Arg Ser
210                 215                 220

Ile Glu Val Leu Lys Thr Gly Arg Ile Thr Lys Val Gly Glu Tyr Glu
225                 230                 235                 240

Leu Glu Phe Ser Gly Gln Ala Lys Lys Arg Gly Val Asp Tyr Ser
                245                 250                 255

Glu Ala Tyr His Ile Tyr Thr Leu Val Lys Ala Asp Leu Val Ile Glu
            260                 265                 270

Ala Trp Asp Glu Leu Arg Ser Leu Pro Glu Ala Ala Glu Leu Gln Gly
        275                 280                 285

Met Asp Asn Ser Asp Val Asn Arg Arg Thr Ala Lys Thr Leu Asn Thr
290                 295                 300

Leu Thr Lys Arg Ile Phe Asn Asn Asp Glu Arg Val Phe Lys Asp Ser
305                 310                 315                 320

Arg Ala Ile Trp Ala Arg Leu Val Phe Glu Leu His Phe Ser Arg Asp
                325                 330                 335

Lys Arg Trp Lys Lys Val Thr Glu Asp Val Phe Trp Arg Glu Met Leu
            340                 345                 350

Gly His Glu Asp Met Asp Thr Gln Arg Ser Tyr Arg Ala Phe Lys Ile
        355                 360                 365

Asp Tyr Asp Glu Pro Asp Gln Ala Asp Gln Asp Tyr Glu His Ala
370                 375                 380

Ser Arg Leu Ala Ala Leu Gln Ala Leu Asp Gly His Glu Gln Leu Glu
385                 390                 395                 400

Ser Ser Asp Ala Gln Ala Arg Val His Ala Trp Val Lys Ala Gln Ile
                405                 410                 415

Glu Gln Glu Pro Asp Ala Lys Ile Thr Gln Ser Leu Ile Ser Arg Glu
            420                 425                 430

Leu Gly Val Tyr Arg Pro Ala Ile Lys Ala Tyr Leu Glu Leu Ala Arg
        435                 440                 445

Glu Ala Leu Asp Ala Pro Asn Val Asp Leu Asp Lys Val Ala Ala Ala
450                 455                 460

Val Pro Lys Glu Val Ala Glu Ala Lys Pro Arg Leu Asn Ala His Pro
465                 470                 475                 480

Gln Gly Asp Gly Arg Trp Val Gly Val Ala Ser Ile Asn Gly Val Glu

```
            485                 490                 495
Val Ala Arg Val Gly Asn Gln Ala Gly Arg Ile Glu Ala Met Lys Ala
        500                 505                 510

Ala Tyr Lys Ala Ala Gly Gly Arg
        515                 520

<210> SEQ ID NO 8
<211> LENGTH: 1854
<212> TYPE: DNA
<213> ORGANISM: Artificial Sequence
<220> FEATURE:
<223> OTHER INFORMATION: Yersinia phage PY54 protelomerase nucleic acid
      sequence

<400> SEQUENCE: 8
atgaaaatcc attttcgcga tttagttagt ggtttagtta agagatcga tgaaatagaa      60 aaatcagacc gggcgcaggg tgacaaaact cggcgttatc agggcgcggc cagaaagttc     120
aaaaatgccg tgtttatgga taacggaaa tatcgcggta acgtatgaa gaatagaata     180 tcgttaacaa catttaataa atatttaagt cgagcacgtt ctcggtttga agaaaggctt     240
caccatagtt ttcctcaatc tatagcaact atctcaaata aatatcctgc attcagcgaa     300
ataataaaag atctggataa tagacccgct catgaagtta gaataaaact aaagaatta     360 ataactcatc ttgaatccgg tgttaattta ttagaaaaaa taggtagctt agggaaaata     420
aaaccatcta cagctaaaaa aatagttagc ttaaaaaaa tgtacccatc atgggctaat     480
gatctagata cttttaattag tactgaagat gctacagaat acaacaaaa gttagagcaa     540 gggaccgacc tacttaacgc attacattct ctaaaagtaa accatgaagt tatgtatgca     600
ttaacgatgc agccttctga cagagctgca ttaaaagcta gcatgacgc tgcccttcac     660 tttaaaagc gtaacatcgt acctatcgat tatcccggct atatgcaacg aatgacggac     720
atactacatc ttccagatat agcttttgaa gattcgatgg catcacttgc cccttagca     780 tttgctctag cagctgctag cggtcgcaga caaattgaaa tactaattac tggtgagttt     840
gacgccaaaa ataaaagcat cattaaattt tctggacaag caaaaaaag aatggccgtt     900 tcaggtggac attatgaaat atacagtcta attgactcag agctattcat caacggtta     960 gagttttac gttctcatag ctcaatactt cgattacaaa atttggaaat agcacatgat    1020
gaacatcgta ctgaactatc tgttattaac ggttttgtag ccaaacctt aaatgatgca    1080 gcaaaacagt tctttgtcga tgacagaaga gtatttaaag atacccgtgc aatttacgct    1140
cgcatagcat atgaaaaatg gtttagaaca gatcctcgct gggcgaagtg cgacgaagat    1200
gttttcttct ctgaattatt aggccatgac gacccagata tcagctggc atataaacaa    1260 ttcaagctgg taaatttcaa tccaaaatgg acacctaata tatcgatga aaaccctcgg    1320 ttagctgcac ttcaagagct tgacaatgat atgcccggcc tagcacgtgg cgatgcggca    1380
gttcgcatac atgagtgggt taagagcaa ctggcgcaga accctgcggc aaaaataact    1440
gcataccaaa tcaagaaaaa tttaaattgt cgaaatgact tggccagccg atacatggca    1500
tggtgtgctg acgcgctagg ggttgttatt ggtgatgatg acaggcaag gccagaagaa    1560 ctcccaccat cgctcgtgct tgatattaac gctgatgaca ctgacgctga agaagatgaa    1620
atagaggaag actttactga tgaggaaata gacgacaccg aattcgacgt atcagataac    1680
gccagtgatg aagataagcc cgaagataaa cctcgctttg cagcaccaat tcgtagaagt    1740
gaggactctt ggctgattaa atttgaattt gctggcaagc aatatagctg ggagggtaat    1800
```
gccgaaagtg ttatcgatgc gatgaaacaa gcatggactg aaaatatgga gtaa          1854

<210> SEQ ID NO 9
<211> LENGTH: 617
<212> TYPE: PRT
<213> ORGANISM: Artificial Sequence
<220> FEATURE:
<223> OTHER INFORMATION: Yersinia phage PY54 protelomerase amino acid
      sequence

<400> SEQUENCE: 9

```
Met Lys Ile His Phe Arg Asp Leu Val Ser Gly Leu Val Lys Glu Ile
1               5                   10                  15

Asp Glu Ile Glu Lys Ser Asp Arg Ala Gln Gly Asp Lys Thr Arg Arg
            20                  25                  30

Tyr Gln Gly Ala Ala Arg Lys Phe Lys Asn Ala Val Phe Met Asp Lys
        35                  40                  45

Arg Lys Tyr Arg Gly Asn Gly Met Lys Asn Arg Ile Ser Leu Thr Thr
    50                  55                  60

Phe Asn Lys Tyr Leu Ser Arg Ala Arg Ser Arg Phe Glu Glu Arg Leu
65                  70                  75                  80

His His Ser Phe Pro Gln Ser Ile Ala Thr Ile Ser Asn Lys Tyr Pro
                85                  90                  95

Ala Phe Ser Glu Ile Ile Lys Asp Leu Asp Asn Arg Pro Ala His Glu
            100                 105                 110

Val Arg Ile Lys Leu Lys Glu Leu Ile Thr His Leu Glu Ser Gly Val
        115                 120                 125

Asn Leu Leu Glu Lys Ile Gly Ser Leu Gly Lys Ile Lys Pro Ser Thr
    130                 135                 140

Ala Lys Lys Ile Val Ser Leu Lys Lys Met Tyr Pro Ser Trp Ala Asn
145                 150                 155                 160

Asp Leu Asp Thr Leu Ile Ser Thr Glu Asp Ala Thr Glu Leu Gln Gln
                165                 170                 175

Lys Leu Glu Gln Gly Thr Asp Leu Leu Asn Ala Leu His Ser Leu Lys
            180                 185                 190

Val Asn His Glu Val Met Tyr Ala Leu Thr Met Gln Pro Ser Asp Arg
        195                 200                 205

Ala Ala Leu Lys Ala Arg His Asp Ala Ala Leu His Phe Lys Lys Arg
    210                 215                 220

Asn Ile Val Pro Ile Asp Tyr Pro Gly Tyr Met Gln Arg Met Thr Asp
225                 230                 235                 240

Ile Leu His Leu Pro Asp Ile Ala Phe Glu Asp Ser Met Ala Ser Leu
                245                 250                 255

Ala Pro Leu Ala Phe Ala Leu Ala Ala Ser Gly Arg Arg Gln Ile
            260                 265                 270

Glu Ile Leu Ile Thr Gly Glu Phe Asp Ala Lys Asn Lys Ser Ile Ile
        275                 280                 285

Lys Phe Ser Gly Gln Ala Lys Arg Met Ala Val Ser Gly Gly His
    290                 295                 300

Tyr Glu Ile Tyr Ser Leu Ile Asp Ser Glu Leu Phe Ile Gln Arg Leu
305                 310                 315                 320

Glu Phe Leu Arg Ser His Ser Ser Ile Leu Arg Leu Gln Asn Leu Glu
                325                 330                 335

Ile Ala His Asp Glu His Arg Thr Glu Leu Ser Val Ile Asn Gly Phe
            340                 345                 350
```

Val Ala Lys Pro Leu Asn Asp Ala Ala Lys Gln Phe Phe Val Asp Asp
        355                 360                 365

Arg Arg Val Phe Lys Asp Thr Arg Ala Ile Tyr Ala Arg Ile Ala Tyr
370                 375                 380

Glu Lys Trp Phe Arg Thr Asp Pro Arg Trp Ala Lys Cys Asp Glu Asp
385                 390                 395                 400

Val Phe Phe Ser Glu Leu Leu Gly His Asp Asp Pro Asp Thr Gln Leu
                405                 410                 415

Ala Tyr Lys Gln Phe Lys Leu Val Asn Phe Asn Pro Lys Trp Thr Pro
            420                 425                 430

Asn Ile Ser Asp Glu Asn Pro Arg Leu Ala Ala Leu Gln Glu Leu Asp
        435                 440                 445

Asn Asp Met Pro Gly Leu Ala Arg Gly Asp Ala Ala Val Arg Ile His
    450                 455                 460

Glu Trp Val Lys Glu Gln Leu Ala Gln Asn Pro Ala Ala Lys Ile Thr
465                 470                 475                 480

Ala Tyr Gln Ile Lys Lys Asn Leu Asn Cys Arg Asn Asp Leu Ala Ser
                485                 490                 495

Arg Tyr Met Ala Trp Cys Ala Asp Ala Leu Gly Val Val Ile Gly Asp
            500                 505                 510

Asp Gly Gln Ala Arg Pro Glu Glu Leu Pro Pro Ser Leu Val Leu Asp
        515                 520                 525

Ile Asn Ala Asp Asp Thr Asp Ala Glu Glu Asp Glu Ile Glu Glu Asp
    530                 535                 540

Phe Thr Asp Glu Glu Ile Asp Asp Thr Glu Phe Asp Val Ser Asp Asn
545                 550                 555                 560

Ala Ser Asp Glu Asp Lys Pro Glu Asp Lys Pro Arg Phe Ala Ala Pro
                565                 570                 575

Ile Arg Arg Ser Glu Asp Ser Trp Leu Ile Lys Phe Glu Phe Ala Gly
            580                 585                 590

Lys Gln Tyr Ser Trp Glu Gly Asn Ala Glu Ser Val Ile Asp Ala Met
        595                 600                 605

Lys Gln Ala Trp Thr Glu Asn Met Glu
    610                 615

<210> SEQ ID NO 10
<211> LENGTH: 1923
<212> TYPE: DNA
<213> ORGANISM: Artificial Sequence
<220> FEATURE:
<223> OTHER INFORMATION: Klebsiella phage phiKO2 protelomerase nucleic
      acid sequence

<400> SEQUENCE: 10
atgcgtaagg tgaaaattgg tgagctaatc aattcgcttg tgagcgaggt cgaggcaatc      60
gatgcctctg atcgtccgca aggcgataaa acgaagaaaa ttaaagccgc agcattaaaa     120
tataagaatg cattatttaa tgacaaagaa agtttcgcg gtaaaggttt agaaaaaaga     180
atttctgcca acacgttcaa ctcgtatatg agtcgggcaa ggaaaagatt tgatgataga     240
ttgcatcata actttgaaaa gaatgtaatt aaactatcag aaaaatatcc tttatatagt     300
gaagaattat cttcgtggct ttctatgcct gcggcatcaa ttagacagca tatgtcaaga     360
ttgcaagcca agctaaaaga gataatgcca ttggcagaag acttatccaa tataagattt     420
ggtacaaaaa atagcgaagc aaaaataaat aaactcgcta taaatatcc tgaatggcaa     480 ttcgctatta gtgatttaaa tagcgaagat tggaaggata aagagatta tctttataaa     540

```
ctattccaac aaggttcttc gctcctggaa gacttgaata acctgaaagt aaaccatgag    600
gttctctatc atctgcagct tagttctgcc gagcgaacct ctatccagca gcgctgggcc    660
aacgtcctca gcgagaaaaa gcgcaacgtt gtcgtgattg actatccgcg ctatatgcag    720
gccatctacg atataatcaa caagcctata gtttcgttcg atttgactac tcgtcgtggt    780
atggccccgc tggcgttcgc ccttgccgcg ctatctggtc gccgaatgat tgaaatcatg    840
ctccagggtg aatttccgt cgcaggtaaa tatacagtaa cattcctggg gcaagctaaa    900
aaacgctcgg aagataaagg tatatcaagg aaaatatata ccttatgcga cgctacttta    960
tttgttagtt tggtaaatga acttcgctca tgccccgctg ctgcggattt tgatgaagta   1020
ataaaggat atggcgaaaa tgacactcgc tcagaaaatg ggcgtattaa tgcaattctc   1080
gctacagctt ttaatccgtg ggtaaaaact ttcttaggcg atgaccgccg cgtttataaa   1140
gatagccgcg ctatttacgc ccgtattgcc tatgaaatgt tcttccgcgt tgaccctcgg   1200
tggaagaatg ttgatgagga tgtattcttc atggagattc tcggccatga cgatgaaaac   1260
acccaactgc actataagca gtttaaattg gctaacttct ccagaacatg gcgaccaaat   1320
gtcggcgagg agaatgcccg cctagcggcg ctgcaaaagc tggatagcat gatgccagat   1380
tttgccaggg gcgacgccgg ggttcgtatt catgagaccg tgaagcagct ggtggagcag   1440
gacccatcga taaaaatcac aaacagcacc ctgcgaccgt ttaacttcag taccaggctg   1500
attcctcgct acctggagtt tgccgccgat gcattgggcc agttcgtcgg tgaaaatggg   1560
caatggcaac tgaaggatga ggcgcctgca atagtcctgc ctgatgagga aattcttgag   1620
cctatggacg acgtcgatct cgatgacgaa aaccatgatg atgaaacgct ggatgacgat   1680
gagatcgaag tggacgaaag cgaaggagag gaactggagg aagcgggcga cgctgaagag   1740
gccgaggtgg ctgaacagga agagaagcac cctggcaagc caaactttaa agcgccgagg   1800
gataatggcg atggtaccta catggtggaa tttgaattcg gtggccgtca ttacgcctgg   1860
tccggtgccg ccggtaatcg ggtagaggca atgcaatctg cctggagtgc ctacttcaag   1920
tga                                                                  1923
```

<210> SEQ ID NO 11
<211> LENGTH: 640
<212> TYPE: PRT
<213> ORGANISM: Artificial Sequence
<220> FEATURE:
<223> OTHER INFORMATION: Klebsiella phage phiKO2 protelomerase amino acid sequence

<400> SEQUENCE: 11

Met Arg Lys Val Lys Ile Gly Glu Leu Ile Asn Ser Leu Val Ser Glu
1               5                   10                  15

Val Glu Ala Ile Asp Ala Ser Asp Arg Pro Gln Gly Asp Lys Thr Lys
            20                  25                  30

Lys Ile Lys Ala Ala Ala Leu Lys Tyr Lys Asn Ala Leu Phe Asn Asp
        35                  40                  45

Lys Arg Lys Phe Arg Gly Lys Gly Leu Glu Lys Arg Ile Ser Ala Asn
    50                  55                  60

Thr Phe Asn Ser Tyr Met Ser Arg Ala Arg Lys Arg Phe Asp Asp Arg
65                  70                  75                  80

Leu His His Asn Phe Glu Lys Asn Val Ile Lys Leu Ser Glu Lys Tyr
                85                  90                  95

Pro Leu Tyr Ser Glu Glu Leu Ser Ser Trp Leu Ser Met Pro Ala Ala

```
               100                 105                 110
    Ser Ile Arg Gln His Met Ser Arg Leu Gln Ala Lys Leu Lys Glu Ile
                115                 120                 125
    Met Pro Leu Ala Glu Asp Leu Ser Asn Ile Lys Ile Gly Thr Lys Asn
                130                 135                 140
    Ser Glu Ala Lys Ile Asn Lys Leu Ala Asn Lys Tyr Pro Glu Trp Gln
    145                 150                 155                 160
    Phe Ala Ile Ser Asp Leu Asn Ser Glu Asp Trp Lys Asp Lys Arg Asp
                        165                 170                 175
    Tyr Leu Tyr Lys Leu Phe Gln Gln Gly Ser Ser Leu Leu Glu Asp Leu
                180                 185                 190
    Asn Asn Leu Lys Val Asn His Glu Val Leu Tyr His Leu Gln Leu Ser
                195                 200                 205
    Ser Ala Glu Arg Thr Ser Ile Gln Gln Arg Trp Ala Asn Val Leu Ser
                210                 215                 220
    Glu Lys Lys Arg Asn Val Val Val Ile Asp Tyr Pro Arg Tyr Met Gln
    225                 230                 235                 240
    Ala Ile Tyr Asp Ile Ile Asn Lys Pro Ile Val Ser Phe Asp Leu Thr
                        245                 250                 255
    Thr Arg Arg Gly Met Ala Pro Leu Ala Phe Ala Leu Ala Ala Leu Ser
                260                 265                 270
    Gly Arg Arg Met Ile Glu Ile Met Leu Gln Gly Glu Phe Ser Val Ala
                275                 280                 285
    Gly Lys Tyr Thr Val Thr Phe Leu Gly Gln Ala Lys Lys Arg Ser Glu
                290                 295                 300
    Asp Lys Gly Ile Ser Arg Lys Ile Tyr Thr Leu Cys Asp Ala Thr Leu
    305                 310                 315                 320
    Phe Val Ser Leu Val Asn Glu Leu Arg Ser Cys Pro Ala Ala Ala Asp
                        325                 330                 335
    Phe Asp Glu Val Ile Lys Gly Tyr Gly Glu Asn Asp Thr Arg Ser Glu
                340                 345                 350
    Asn Gly Arg Ile Asn Ala Ile Leu Ala Thr Ala Phe Asn Pro Trp Val
                355                 360                 365
    Lys Thr Phe Leu Gly Asp Asp Arg Arg Val Tyr Lys Asp Ser Arg Ala
                370                 375                 380
    Ile Tyr Ala Arg Ile Ala Tyr Glu Met Phe Phe Arg Val Asp Pro Arg
    385                 390                 395                 400
    Trp Lys Asn Val Asp Glu Asp Val Phe Phe Met Glu Ile Leu Gly His
                        405                 410                 415
    Asp Asp Glu Asn Thr Gln Leu His Tyr Lys Gln Phe Lys Leu Ala Asn
                420                 425                 430
    Phe Ser Arg Thr Trp Arg Pro Asn Val Gly Glu Glu Asn Ala Arg Leu
                435                 440                 445
    Ala Ala Leu Gln Lys Leu Asp Ser Met Met Pro Asp Phe Ala Arg Gly
                450                 455                 460
    Asp Ala Gly Val Arg Ile His Glu Thr Val Lys Gln Leu Val Glu Gln
    465                 470                 475                 480
    Asp Pro Ser Ile Lys Ile Thr Asn Ser Thr Leu Arg Pro Phe Asn Phe
                        485                 490                 495
    Ser Thr Arg Leu Ile Pro Arg Tyr Leu Glu Phe Ala Ala Asp Ala Leu
                500                 505                 510
    Gly Gln Phe Val Gly Glu Asn Gly Gln Trp Gln Leu Lys Asp Glu Ala
                515                 520                 525
```

```
Pro Ala Ile Val Leu Pro Asp Glu Glu Ile Leu Glu Pro Met Asp Asp
    530                 535                 540
Val Asp Leu Asp Asp Glu Asn His Asp Asp Glu Thr Leu Asp Asp Asp
545                 550                 555                 560
Glu Ile Glu Val Asp Glu Ser Glu Gly Glu Leu Glu Glu Ala Gly
                565                 570                 575
Asp Ala Glu Glu Ala Glu Val Ala Glu Gln Glu Glu Lys His Pro Gly
            580                 585                 590
Lys Pro Asn Phe Lys Ala Pro Arg Asp Asn Gly Asp Gly Thr Tyr Met
        595                 600                 605
Val Glu Phe Glu Phe Gly Gly Arg His Tyr Ala Trp Ser Gly Ala Ala
    610                 615                 620
Gly Asn Arg Val Glu Ala Met Gln Ser Ala Trp Ser Ala Tyr Phe Lys
625                 630                 635                 640
```

<210> SEQ ID NO 12
<211> LENGTH: 1617
<212> TYPE: DNA
<213> ORGANISM: Artificial Sequence
<220> FEATURE:
<223> OTHER INFORMATION: Vibrio phage VP882 protelomerase nucleic acid
      sequence

<400> SEQUENCE: 12

```
atgagcggcg aaagtagaca aaaggtaaac ctcgaggagt taataaatga gctcgtcgag    60
gaggtgaaaa ccatcgatga caatgaggcg attactcggt ctgaaaaaac caagttgatc   120
accagggcgg cgactaaatt caagaccaag ctgcacgacg ataagcgccg gaaggatgcg   180
accagaatcg ctctgagcac ctatcgtaag tacatgacaa tggccagggc agcagttact   240
gagcagaact ggaaacacca cagtctcgag cagcagatag agcggctggc caaaaagcac   300
ccgcaatacg ctgagcagct ggtggccatc ggggccatgg ataacatcac cgagttgcgc   360
ctggcgcatc gcgacctcct gaagagcatc aaggacaacg atgaagcctt cgaggatatc   420
cgcagcatga gttagacca cgaggtaatg cgccatctga cgctacccag tgcgcaaaag   480
gcgagactgg cagaggaagc cgccgaggcg ttgaccgaga gaaaaccgc cacggtcgac   540
atcaactatc acgagctgat ggccggcgtg gtggagctgt tgaccaagaa gaccaagacg   600
gtcggcagcg acagcaccta cagcttcagc cggctggcgc ttggtattgg cctggctacc   660
ggtcgtcgtt ctatcgagat actgaagcag ggcgagttca aaaaggtgga tgagcagcgg   720
ctcgagttct ctggccaagc gaaaaagcgc ggcggtgccg actattcaga gacctatacc   780
atttacaccc tggtcgactc cgacctggta ctgatggcgc tgaagaacct gcgagagttg   840
ccagaagttc gcgcactgga tgagtacgac caactgggcg agattaagcg aacgacgcc   900
atcaataaac gctgtgcaaa aacgctcaac caaaccgcca gcagttctt tggcagcgac   960
gagcgcgtgt tcaaagatag tcgtgccatc tgggcgcgtc tggcttatga gttgttttt   1020
caacgtgatc cgcgctggaa aaagaaagac gaggacgttt tctggcagga gatgctgggc  1080
cacgaggaca tcgagactca gaaagcctat aagcaattca aggtcgacta cagcgaacct  1140
gagcagccgg tgcacaagcc tggcaaattt aagagcagag ctgaagccct cgcggcgctc  1200
gactcaaatg aggacattac caccgctca tccatggcca agatccacga ctgggtgaaa  1260
gagcgtattg cggaagaccc cgaggcgaac atcacacagt cactcatcac ccgggaactg  1320
ggctcaggcc gtaaggtgat caaggactac ctcgacctgg ctgacgatgc ccttgctgtg  1380
```

-continued

```
gtgaatactc tgtcgatga cgcagtcgtc gaggttccag ctgatgtgcc ggcagcagaa    1440
aaacagccga agaaagcgca gaagcccaga ctcgtggctc accaggttga tgatgagcac    1500
tgggaagcct gggcgctggt ggaaggcgag gaggtggcca gggtgaaaat caagggcacc    1560
cgcgttgagg caatgacagc cgcatgggag gccagccaaa aggcactcga tgactaa      1617
```

<210> SEQ ID NO 13
<211> LENGTH: 538
<212> TYPE: PRT
<213> ORGANISM: Artificial Sequence
<220> FEATURE:
<223> OTHER INFORMATION: Vibrio phage VP882 protelomerase amino acid
      sequence

<400> SEQUENCE: 13

```
Met Ser Gly Glu Ser Arg Gln Lys Val Asn Leu Glu Glu Leu Ile Asn
1               5                   10                  15

Glu Leu Val Glu Val Lys Thr Ile Asp Asp Asn Glu Ala Ile Thr
            20                  25                  30

Arg Ser Glu Lys Thr Lys Leu Ile Thr Arg Ala Ala Thr Lys Phe Lys
        35                  40                  45

Thr Lys Leu His Asp Asp Lys Arg Arg Lys Asp Ala Thr Arg Ile Ala
    50                  55                  60

Leu Ser Thr Tyr Arg Lys Tyr Met Thr Met Ala Arg Ala Ala Val Thr
65                  70                  75                  80

Glu Gln Asn Trp Lys His His Ser Leu Glu Gln Gln Ile Glu Arg Leu
                85                  90                  95

Ala Lys Lys His Pro Gln Tyr Ala Glu Gln Leu Val Ala Ile Gly Ala
            100                 105                 110

Met Asp Asn Ile Thr Glu Leu Arg Leu Ala His Arg Asp Leu Leu Lys
        115                 120                 125

Ser Ile Lys Asp Asn Asp Glu Ala Phe Glu Asp Ile Arg Ser Met Lys
    130                 135                 140

Leu Asp His Glu Val Met Arg His Leu Thr Leu Pro Ser Ala Gln Lys
145                 150                 155                 160

Ala Arg Leu Ala Glu Glu Ala Ala Glu Ala Leu Thr Glu Lys Lys Thr
                165                 170                 175

Ala Thr Val Asp Ile Asn Tyr His Glu Leu Met Ala Gly Val Val Glu
            180                 185                 190

Leu Leu Thr Lys Lys Thr Lys Thr Val Gly Ser Asp Ser Thr Tyr Ser
        195                 200                 205

Phe Ser Arg Leu Ala Leu Gly Ile Gly Leu Ala Thr Gly Arg Arg Ser
    210                 215                 220

Ile Glu Ile Leu Lys Gln Gly Glu Phe Lys Lys Val Asp Glu Gln Arg
225                 230                 235                 240

Leu Glu Phe Ser Gly Gln Ala Lys Lys Arg Gly Gly Ala Asp Tyr Ser
                245                 250                 255

Glu Thr Tyr Thr Ile Tyr Thr Leu Val Asp Ser Asp Leu Val Leu Met
            260                 265                 270

Ala Leu Lys Asn Leu Arg Glu Leu Pro Glu Val Arg Ala Leu Asp Glu
        275                 280                 285

Tyr Asp Gln Leu Gly Glu Ile Lys Arg Asn Asp Ala Ile Asn Lys Arg
    290                 295                 300

Cys Ala Lys Thr Leu Asn Gln Thr Ala Lys Gln Phe Phe Gly Ser Asp
305                 310                 315                 320
```

-continued

```
Glu Arg Val Phe Lys Asp Ser Arg Ala Ile Trp Ala Arg Leu Ala Tyr
                325                 330                 335

Glu Leu Phe Phe Gln Arg Asp Pro Arg Trp Lys Lys Asp Glu Asp
            340                 345                 350

Val Phe Trp Gln Glu Met Leu Gly His Glu Asp Ile Glu Thr Gln Lys
        355                 360                 365

Ala Tyr Lys Gln Phe Lys Val Asp Tyr Ser Glu Pro Glu Gln Pro Val
    370                 375                 380

His Lys Pro Gly Lys Phe Lys Ser Arg Ala Glu Ala Leu Ala Ala Leu
385                 390                 395                 400

Asp Ser Asn Glu Asp Ile Thr Thr Arg Ser Ser Met Ala Lys Ile His
                405                 410                 415

Asp Trp Val Lys Glu Arg Ile Ala Glu Asp Pro Glu Ala Asn Ile Thr
            420                 425                 430

Gln Ser Leu Ile Thr Arg Glu Leu Gly Ser Gly Arg Lys Val Ile Lys
        435                 440                 445

Asp Tyr Leu Asp Leu Ala Asp Asp Ala Leu Ala Val Val Asn Thr Pro
    450                 455                 460

Val Asp Asp Ala Val Glu Val Pro Ala Asp Val Pro Ala Ala Glu
465                 470                 475                 480

Lys Gln Pro Lys Lys Ala Gln Lys Pro Arg Leu Val Ala His Gln Val
                485                 490                 495

Asp Asp Glu His Trp Glu Ala Trp Ala Leu Val Glu Gly Glu Val
            500                 505                 510

Ala Arg Val Lys Ile Lys Gly Thr Arg Val Gly Ala Met Thr Ala Ala
        515                 520                 525

Trp Glu Ala Ser Gln Lys Ala Leu Asp Asp
    530                 535
```

<210> SEQ ID NO 14
<211> LENGTH: 4055
<212> TYPE: DNA
<213> ORGANISM: Artificial Sequence
<220> FEATURE:
<223> OTHER INFORMATION: Escherichia coli bacteriophage N15 telomerase
      (telN) and secondary immunity repressor (cA) nucleic acid sequence

<400> SEQUENCE: 14

```
catatgcact atatcatatc tcaattacgg aacatatcag cacacaattg cccattatac      60
gcgcgtataa tggactattg tgtgctgata aggagaacat aagcgcagaa caatatgtat     120
ctattccggt gttgtgttcc tttgttattc tgctattatg ttctcttata gtgtgacgaa     180
agcagcataa ttaatcgtca cttgttcttt gattgtgtta cgatatccag agacttagaa     240 acggggaac cggatgagc aaggtaaaaa tcggtgagtt gatcaacacg cttgtgaatg       300
aggtagaggc aattgatgcc tcagaccgcc cacaaggcga caaaacgaag agaattaaag     360
ccgcagccgc acgtataag aacgcgttat ttaatgataa agaaagttc cgtgggaaag      420 gattgcagaa aagaataacc gcgaatactt ttaacgccta tatgagcagg gcaagaaagc    480
ggtttgatga taaattacat catagctttg ataaaaatat taataaatta tcggaaaagt    540
atcctcttta cagcgaagaa ttatcttcat ggctttctat gcctacggct aatattcgcc    600
agcacatgtc atcgttacaa tctaaattga agaaataat gccgcttgcc gaagagttat    660
caaatgtaag aataggctct aaaggcagtg atgcaaaaat agcaagacta ataaaaaat    720 atccagattg gagttttgct cttagtgatt taaacagtga tgattggaag gagcgccgtg     780
```

```
actatctttta taagttattc caacaaggct ctgcgttgtt agaagaacta caccagctca    840
aggtcaacca tgaggttctg taccatctgc agctaagccc tgcggagcgt acatctatac    900
agcaacgatg ggccgatgtt ctgcgcgaga agaagcgtaa tgttgtggtt attgactacc    960
caacatacat gcagtctatc tatgatattt tgaataatcc tgcgacttta tttagtttaa   1020
acactcgttc tggaatggca cctttggcct ttgctctggc tgcggtatca gggcgaagaa   1080
tgattgagat aatgtttcag ggtgaatttg ccgtttcagg aaagtatacg gttaatttct   1140
cagggcaagc taaaaaacgc tctgaagata aaagcgtaac cagaacgatt tatactttat   1200
gcgaagcaaa attattcgtt gaattattaa cagaattgcg ttcttgctct gctgcatctg   1260
atttcgatga ggttgttaaa ggatatggaa aggatgatac aaggtctgag aacggcagga   1320
taaatgctat tttagcaaaa gcatttaacc cttgggttaa atcattttc ggcgatgacc    1380
gtcgtgttta taagatagc cgcgctattt acgctcgcat cgcttatgag atgttcttcc     1440
gcgtcgatcc acggtggaaa aacgtcgacg aggatgtgtt cttcatggag attctcggac   1500
acgacgatga gaacacccag ctgcactata agcagttcaa gctggccaac ttctccagaa   1560
cctggcgacc tgaagttggg gatgaaaaca ccaggctggt ggctctgcag aaactggacg   1620
atgaaatgcc aggctttgcc agaggtgacg ctggcgtccg tctccatgaa accgttaagc   1680
agctggtgga gcaggaccca tcagcaaaaa taaccaacag cactctccgg gcctttaaat   1740
ttagcccgac gatgattagc cggtacctgg agtttgccgc tgatgcattg gggcagttcg   1800
ttggcgagaa cgggcagtgg cagctgaaga tagagacacc tgcaatcgtc ctgcctgatg   1860
aagaatccgt tgagaccatc gacgaaccgg atgatgagtc ccaagacgac gagctggatg   1920
aagatgaaat tgagctcgac gagggtggcg gcgatgaacc aaccgaagag aagggccag    1980
aagaacatca gccaactgct ctaaaacccg tcttcaagcc tgcaaaaaat aacgggacg    2040
gaacgtacaa gatagagttt gaatacgatg gaaagcatta tgcctggtcc ggccccgccg   2100
atagccctat ggccgcaatg cgatccgcat gggaaacgta ctacagctaa aagaaaagcc   2160
accggtgtta atcggtggct tttttattga ggcctgtccc tacccatccc ctgcaaggga   2220
cggaaggatt aggcggaaac tgcagctgca actacggaca tcgccgtccc gactgcaggg   2280
acttccccgc gtaaagcggg gcttaaattc gggctggcca accctatttt tctgcaatcg   2340
ctggcgatgt tagtttcgtg gatagcgttt ccagcttttc aatggccagc tcaaaatgtg   2400
ctggcagcac cttctccagt tccgtatcaa tatcggtgat cggcagctct ccacaagaca   2460
tactccggcg accgccacga actacatcgc gcagcagctc ccgttcgtag acacgcatgt   2520
tgcccagagc cgtttctgca gccgttaata tccggcgcac gtcggcgatg attgccggga   2580
gatcatccac ggttattggg ttcggtgatg ggttcctgca ggcgcggcgg agagccatcc   2640
agacgccgct aacccatgcg ttacggtact gaaaactttg tgctatgtcg tttatcaggc   2700
ccgaagttct tctttctgcc gccagtccag tggttcaccg gcgttcttag gctcaggctc   2760
gacaaaagca tactcgccgt ttttccggat agctggcaga acctcgttcg tcacccactt   2820
gcggaaccgc caggctgtcg tcccctgttt caccgcgtcg cggcagcgga ggattatggt   2880
gtagagacca gattccgata ccacatttac ttccctggcc atccgatcaa gtttttgtgc   2940
ctcggttaaa ccgagggtca attttcatc atgatccagc ttacgcaatg catcagaagg   3000
gttggctata ttcaatgcag cacagatatc cagcgccaca aaccacgggt caccaccgac   3060
aagaaccacc cgtatagggt ggctttcctg aaatgaaaag acgagagag ccttcattgc     3120
gcctccccgg atttcagctg ctcagaaagg gacagggagc agccgcgagc ttcctgcgtg   3180
```

-continued

```
agttcgcgcg cgacctgcag aagttccgca gcttcctgca aatacagcgt ggcctcataa    3240
ctggagatag tgcggtgagc agagcccaca agcgcttcaa cctgcagcag gcgttcctca    3300
atcgtctcca gcaggccctg ggcgtttaac tgaatctggt tcatgcgatc acctcgctga    3360
ccgggatacg ggctgacaga acgaggacaa aacggctggc gaactggcga cgagcttctc    3420
gctcggatga tgcaatggtg gaaaggcggt ggatatggga tttttttgtcc gtgcggacga    3480 cagctgcaaa tttgaatttg aacatggtat gcattcctat cttgtatagg gtgctaccac    3540
cagagttgag aatctctata ggggtggtag cccagacagg gttctcaaca ccggtacaag    3600
aagaaaccgg cccaaccgaa gttggcccca tctgagccac cataattcag gtatgcgcag    3660
atttaacaca caaaaaaaca cgctggcgcg tgttgtgcgc ttcttgtcat cggggttga     3720 gaggcccggc tgcagatttt gctgcagcgg ggtaactcta ccgccaaagc agaacgcacg    3780
tcaataattt aggtggatat tttaccccgt gaccagtcac gtgcacaggt gttttatag    3840 tttgctttac tgactgatca gaacctgatc agttattgga gtccggtaat cttattgatg    3900
accgcagcca ccttagatgt tgtctcaaac cccatacggc cacgaatgag ccactggaac    3960
ggaatagtca gcaggtacag cggaacgaac cacaaacggt tcagacgctg ccagaacgtc    4020
gcatcacgac gttccatcca ttcggtattg tcgac                              4055
```

<210> SEQ ID NO 15
<211> LENGTH: 631
<212> TYPE: PRT
<213> ORGANISM: Artificial Sequence
<220> FEATURE:
<223> OTHER INFORMATION: Escherichia coli bacteriophage N15 telomerase
    amino acid sequence

<400> SEQUENCE: 15

```
Met Ser Lys Val Lys Ile Gly Glu Leu Ile Asn Thr Leu Val Asn Glu
1               5                   10                  15

Val Glu Ala Ile Asp Ala Ser Asp Arg Pro Gln Gly Asp Lys Thr Lys
            20                  25                  30

Arg Ile Lys Ala Ala Ala Ala Arg Tyr Lys Asn Ala Leu Phe Asn Asp
        35                  40                  45

Lys Arg Lys Phe Arg Gly Lys Gly Leu Gln Lys Arg Ile Thr Ala Asn
    50                  55                  60

Thr Phe Asn Ala Tyr Met Ser Arg Ala Arg Lys Arg Phe Asp Asp Lys
65                  70                  75                  80

Leu His His Ser Phe Asp Lys Asn Ile Asn Lys Leu Ser Glu Lys Tyr
                85                  90                  95

Pro Leu Tyr Ser Glu Glu Leu Ser Ser Trp Leu Ser Met Pro Thr Ala
            100                 105                 110

Asn Ile Arg Gln His Met Ser Ser Leu Gln Ser Lys Leu Lys Glu Ile
        115                 120                 125

Met Pro Leu Ala Glu Glu Leu Ser Asn Val Arg Ile Gly Ser Lys Gly
    130                 135                 140

Ser Asp Ala Lys Ile Ala Arg Leu Ile Lys Lys Tyr Pro Asp Trp Ser
145                 150                 155                 160

Phe Ala Leu Ser Asp Leu Asn Ser Asp Asp Trp Lys Glu Arg Arg Asp
                165                 170                 175

Tyr Leu Tyr Lys Leu Phe Gln Gln Gly Ser Ala Leu Leu Glu Glu Leu
            180                 185                 190

His Gln Leu Lys Val Asn His Glu Val Leu Tyr His Leu Gln Leu Ser
```

```
            195                 200                 205
Pro Ala Glu Arg Thr Ser Ile Gln Gln Arg Trp Ala Asp Val Leu Arg
210                 215                 220

Glu Lys Lys Arg Asn Val Val Ile Asp Tyr Pro Thr Tyr Met Gln
225                 230                 235                 240

Ser Ile Tyr Asp Ile Leu Asn Asn Pro Ala Thr Leu Phe Ser Leu Asn
                    245                 250                 255

Thr Arg Ser Gly Met Ala Pro Leu Ala Phe Ala Leu Ala Ala Val Ser
                260                 265                 270

Gly Arg Arg Met Ile Glu Ile Met Phe Gln Gly Glu Phe Ala Val Ser
                275                 280                 285

Gly Lys Tyr Thr Val Asn Phe Ser Gly Gln Ala Lys Lys Arg Ser Glu
290                 295                 300

Asp Lys Ser Val Thr Arg Thr Ile Tyr Thr Leu Cys Glu Ala Lys Leu
305                 310                 315                 320

Phe Val Glu Leu Leu Thr Glu Leu Arg Ser Cys Ser Ala Ala Ser Asp
                325                 330                 335

Phe Asp Glu Val Val Lys Gly Tyr Gly Lys Asp Asp Thr Arg Ser Glu
                340                 345                 350

Asn Gly Arg Ile Asn Ala Ile Leu Ala Lys Ala Phe Asn Pro Trp Val
                355                 360                 365

Lys Ser Phe Phe Gly Asp Asp Arg Arg Val Tyr Lys Asp Ser Arg Ala
370                 375                 380

Ile Tyr Ala Arg Ile Ala Tyr Glu Met Phe Arg Val Asp Pro Arg
385                 390                 395                 400

Trp Lys Asn Val Asp Glu Asp Val Phe Phe Met Glu Ile Leu Gly His
                    405                 410                 415

Asp Asp Glu Asn Thr Gln Leu His Tyr Lys Gln Phe Lys Leu Ala Asn
                420                 425                 430

Phe Ser Arg Thr Trp Arg Pro Glu Val Gly Asp Glu Asn Thr Arg Leu
                435                 440                 445

Val Ala Leu Gln Lys Leu Asp Asp Glu Met Pro Gly Phe Ala Arg Gly
450                 455                 460

Asp Ala Gly Val Arg Leu His Glu Thr Val Lys Gln Leu Val Glu Gln
465                 470                 475                 480

Asp Pro Ser Ala Lys Ile Thr Asn Ser Thr Leu Arg Ala Phe Lys Phe
                485                 490                 495

Ser Pro Thr Met Ile Ser Arg Tyr Leu Glu Phe Ala Ala Asp Ala Leu
                500                 505                 510

Gly Gln Phe Val Gly Glu Asn Gly Gln Trp Gln Leu Lys Ile Glu Thr
                515                 520                 525

Pro Ala Ile Val Leu Pro Asp Glu Glu Ser Val Glu Thr Ile Asp Glu
                530                 535                 540

Pro Asp Asp Glu Ser Gln Asp Glu Leu Asp Glu Asp Glu Ile Glu
545                 550                 555                 560

Leu Asp Glu Gly Gly Gly Asp Glu Pro Thr Glu Glu Gly Pro Glu
                565                 570                 575

Glu His Gln Pro Thr Ala Leu Lys Pro Val Phe Lys Pro Ala Lys Asn
                580                 585                 590

Asn Gly Asp Gly Thr Tyr Lys Ile Glu Phe Glu Tyr Asp Gly Lys His
                595                 600                 605

Tyr Ala Trp Ser Gly Pro Ala Asp Ser Pro Met Ala Ala Met Arg Ser
610                 615                 620
```

Ala Trp Glu Thr Tyr Tyr Ser
625                 630

<210> SEQ ID NO 16
<211> LENGTH: 22
<212> TYPE: DNA
<213> ORGANISM: Artificial Sequence
<220> FEATURE:
<223> OTHER INFORMATION: 22 base consensus sequence for a mesophilic
      bacteriophage perfect inverted repeat
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (5)..(6)
<223> OTHER INFORMATION: n is a, c, g, or t
<220> FEATURE:
<221> NAME/KEY: misc_feature
<222> LOCATION: (9)..(10)
<223> OTHER INFORMATION: n is a, c, g, or t
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t

<400> SEQUENCE: 16
ncatnntann cgnntannat gn                                              22

<210> SEQ ID NO 17
<211> LENGTH: 22
<212> TYPE: DNA
<213> ORGANISM: Artificial Sequence
<220> FEATURE:
<223> OTHER INFORMATION: particularly preferred perfect inverted repeat
      sequence for use with E.coli phage N15 and Klebsiella phage Phi
      KO2 protelomerases

<400> SEQUENCE: 17
ccattatacg cgcgtataat gg                                              22

<210> SEQ ID NO 18
<211> LENGTH: 22
<212> TYPE: DNA
<213> ORGANISM: Artificial Sequence
<220> FEATURE:
<223> OTHER INFORMATION: particularly preferred perfect inverted repeat
      sequence for use with Yersinia phage PY54 protelomerase

<400> SEQUENCE: 18
gcatactacg cgcgtagtat gc                                              22

<210> SEQ ID NO 19
<211> LENGTH: 22
<212> TYPE: DNA
<213> ORGANISM: Artificial Sequence
<220> FEATURE:
<223> OTHER INFORMATION: particularly preferred perfect inverted repeat
      sequence for use with Halomonas phage phiHAP-1 protelomerase

<400> SEQUENCE: 19
ccatactata cgtatagtat gg                                            22

<210> SEQ ID NO 20
<211> LENGTH: 22
<212> TYPE: DNA
<213> ORGANISM: Artificial Sequence
<220> FEATURE:
<223> OTHER INFORMATION: particularly preferred perfect inverted repeat
      sequence for use with Vibrio phage VP882 protelomerase

<400> SEQUENCE: 20
gcatactata cgtatagtat gc                                            22

<210> SEQ ID NO 21
<211> LENGTH: 14
<212> TYPE: DNA
<213> ORGANISM: Artificial Sequence
<220> FEATURE:
<223> OTHER INFORMATION: particularly preferred perfect inverted repeat
      sequence for use with a Borrelia burgdorferi protelomerase

<400> SEQUENCE: 21
attatatata taat                                                     14

<210> SEQ ID NO 22
<211> LENGTH: 24
<212> TYPE: DNA
<213> ORGANISM: Artificial Sequence
<220> FEATURE:
<223> OTHER INFORMATION: particularly preferred perfect inverted repeat
      sequence for use with Vibrio phage VP882 protelomerase

<400> SEQUENCE: 22
ggcatactat acgtatagta tgcc                                          24

<210> SEQ ID NO 23
<211> LENGTH: 42
<212> TYPE: DNA
<213> ORGANISM: Artificial Sequence
<220> FEATURE:
<223> OTHER INFORMATION: particularly preferred perfect inverted repeat
      sequence for use with Yersinia phage PY54 protelomerase

<400> SEQUENCE: 23
acctatttca gcatactacg cgcgtagtat gctgaaatag gt                      42

<210> SEQ ID NO 24
<211> LENGTH: 90
<212> TYPE: DNA
<213> ORGANISM: Artificial Sequence
<220> FEATURE:
<223> OTHER INFORMATION: particularly preferred perfect inverted repeat
      sequence for use with Halomonas phage phiHAP-1 protelomerase

<400> SEQUENCE: 24
cctatattgg gccacctatg tatgcacagt tcgcccatac tatacgtata gtatgggcga   60
actgtgcata cataggtggc ccaatatagg                                    90

<210> SEQ ID NO 25
<211> LENGTH: 56
<212> TYPE: DNA
<213> ORGANISM: Artificial Sequence
<220> FEATURE:
<223> OTHER INFORMATION: Particularly preferred protelomerase target
      sequence

<400> SEQUENCE: 25
tatcagcaca caattgccca ttatacgcgc gtataatgga ctattgtgtg ctgata    56

<210> SEQ ID NO 26
<211> LENGTH: 42
<212> TYPE: DNA
<213> ORGANISM: Artificial Sequence
<220> FEATURE:
<223> OTHER INFORMATION: Particularly preferred protelomerase target
      sequence

<400> SEQUENCE: 26
atgcgcgcat ccattatacg cgcgtataat ggcgataata ca    42

<210> SEQ ID NO 27
<211> LENGTH: 52
<212> TYPE: DNA
<213> ORGANISM: Artificial Sequence
<220> FEATURE:
<223> OTHER INFORMATION: Particularly preferred protelomerase target
      sequence

<400> SEQUENCE: 27
tagtcaccta tttcagcata ctacgcgcgt agtatgctga aataggttac tg    52

<210> SEQ ID NO 28
<211> LENGTH: 90
<212> TYPE: DNA
<213> ORGANISM: Artificial Sequence
<220> FEATURE:
<223> OTHER INFORMATION: Particularly preferred protelomerase target
      sequence

<400> SEQUENCE: 28
gggatcccgt tccatacata catgtatcca tgtggcatac tatacgtata gtatgccgat    60
gttacatatg gtatcattcg ggatcccgtt    90

<210> SEQ ID NO 29
<211> LENGTH: 38
<212> TYPE: DNA
<213> ORGANISM: Artificial Sequence
<220> FEATURE:
<223> OTHER INFORMATION: Particularly preferred protelomerase target
      sequence

<400> SEQUENCE: 29
tactaaataa atattatata taaattttt tattagta    38

<210> SEQ ID NO 30
<211> LENGTH: 22
<212> TYPE: DNA
<213> ORGANISM: Artificial Sequence
<220> FEATURE:
<223> OTHER INFORMATION: PT1F primer

<400> SEQUENCE: 30
atgagcaagg taaaaatcgg tg    22

<210> SEQ ID NO 31
<211> LENGTH: 22
<212> TYPE: DNA
<213> ORGANISM: Artificial Sequence
<220> FEATURE:
<223> OTHER INFORMATION: PT1R primer

<400> SEQUENCE: 31

```
ttagctgtag tacgtttccc at                                              22
```

<210> SEQ ID NO 32
<211> LENGTH: 62
<212> TYPE: DNA
<213> ORGANISM: Artificial Sequence
<220> FEATURE:
<223> OTHER INFORMATION: RL1

<400> SEQUENCE: 32

```
agctttatca gcacacaatt gcccattata cgcgcgtata atggactatt gtgtgctgat    60
ag                                                                    62
```

<210> SEQ ID NO 33
<211> LENGTH: 62
<212> TYPE: DNA
<213> ORGANISM: Artificial Sequence
<220> FEATURE:
<223> OTHER INFORMATION: RL2

<400> SEQUENCE: 33

```
gatcctatca gcacacaata gtccattata cgcgcgtata atgggcaatt gtgtgctgat    60
aa                                                                    62
```

<210> SEQ ID NO 34
<211> LENGTH: 22
<212> TYPE: DNA
<213> ORGANISM: Artificial Sequence
<220> FEATURE:
<223> OTHER INFORMATION: Sac pGL

<400> SEQUENCE: 34

```
gtgcaagtgc aggtgccaga ac                                              22
```

<210> SEQ ID NO 35
<211> LENGTH: 27
<212> TYPE: DNA
<213> ORGANISM: Artificial Sequence
<220> FEATURE:
<223> OTHER INFORMATION: Bam pGL

<400> SEQUENCE: 35

```
gataaagaag acagtcataa gtgcggc                                         27
```

<210> SEQ ID NO 36
<211> LENGTH: 56
<212> TYPE: DNA
<213> ORGANISM: Artificial Sequence
<220> FEATURE:
<223> OTHER INFORMATION: Complememt to SEQ ID NO: 25

<400> SEQUENCE: 36

```
tatcagcaca caatagtcca ttatacgcgc gtataatggg caattgtgtg ctgata        56
```

<210> SEQ ID NO 37
<211> LENGTH: 56
<212> TYPE: DNA
<213> ORGANISM: Artificial Sequence
<220> FEATURE:
<223> OTHER INFORMATION: telR

<400> SEQUENCE: 37

```
tatcagcaca caattgccca ttatacgcgc gtataatggg caattgtgtg ctgata        56
```

```
<210> SEQ ID NO 38
<211> LENGTH: 56
<212> TYPE: DNA
<213> ORGANISM: Artificial Sequence
<220> FEATURE:
<223> OTHER INFORMATION: telL

<400> SEQUENCE: 38
tatcagcaca caatagtcca ttatacgcgc gtataatgga ctattgtgtg ctgata        56

<210> SEQ ID NO 39
<211> LENGTH: 42
<212> TYPE: DNA
<213> ORGANISM: Artificial Sequence
<220> FEATURE:
<223> OTHER INFORMATION: Complement of SEQ ID NO: 26

<400> SEQUENCE: 39
tgtattatcg ccattatacg cgcgtataat ggatgcgcgc at                      42

<210> SEQ ID NO 40
<211> LENGTH: 52
<212> TYPE: DNA
<213> ORGANISM: Artificial Sequence
<220> FEATURE:
<223> OTHER INFORMATION: Complement of SEQ ID NO: 27

<400> SEQUENCE: 40
cagtaaccta tttcagcata ctacgcgcgt agtatgctga aataggtgac ta           52

<210> SEQ ID NO 41
<211> LENGTH: 90
<212> TYPE: DNA
<213> ORGANISM: Artificial Sequence
<220> FEATURE:
<223> OTHER INFORMATION: Complement of SEQ ID NO: 28

<400> SEQUENCE: 41
aacgggatcc cgaatgatac cacatgtaac atcggcatac tatacgtata gtatgccaca   60
tggatacatg tatgtatgga acgggatccc                                    90

<210> SEQ ID NO 42
<211> LENGTH: 38
<212> TYPE: DNA
<213> ORGANISM: Artificial Sequence
<220> FEATURE:
<223> OTHER INFORMATION: Complement of SEQ ID NO: 29

<400> SEQUENCE: 42
tactaataaa aaattatata tataatattt atttagta                           38
```

DNA VACCINES

CROSS-REFERENCE TO RELATED APPLICATIONS

This Application is a continuation of U.S. patent application Ser. No. 14/814,258 filed on Jul. 30, 2015, which is a divisional of U.S. patent application Ser. No. 13/146,350 filed on Jul. 23, 2012, which is a national phase application under 35 U.S.C. § 371 that claims priority to International Application No. PCT/GB2010/000165 filed Feb. 1, 2010, which claims priority to GB Patent Application 0901593.4 filed on Jan. 30, 2009. The above applications in their entirety are hereby incorporated by reference for all purposes and made a part of the present disclosure.

FIELD OF THE INVENTION

The present invention relates to an in vitro, cell-free process for the production of closed linear deoxyribonucleic acid (DNA).

BACKGROUND OF THE INVENTION

Traditional cell-based processes for amplification of DNA in large quantities are costly. For example, use of bacteria requires their growth in large volumes in expensive fermenters that are required to be maintained in a sterile state in order to prevent contamination of the culture. The bacteria also need to be lysed to release the amplified DNA and the DNA needs to be cleaned and purified from other bacterial components. In particular, where DNA vaccines or other therapeutic DNA agents are produced, high purity is required to eliminate the presence of endotoxins which are toxic to mammals.

In addition to the issues of cost, use of bacteria can in many cases present difficulties for fidelity of the amplification process. In the complex biochemical environment of the bacterial cell, it is difficult to control the quality and yields of the desired DNA product. The bacteria may occasionally alter the required gene cloned within the amplified DNA and render it useless for the required purpose. Recombination events may also lead to problems in faithful production of a DNA of interest. Cell-free enzymatic processes for amplification of DNA avoid the requirement for use of a host cell, and so are advantageous.

For example, the manufacture of medicinal DNA cassettes relies on almost exclusively on their insertion into bacterial plasmids and their amplification in bacterial fermentation processes.

This current state of the art process limits opportunities for improving the manufacture of such DNA medicines in a number of ways. In addition, the plasmid product is essentially a crude DNA molecule in that it contains nucleotide sequences not required for its medicinal function. Accordingly, in the field of production of DNA products, such as DNA medicines, there is a need to provide improved methods for amplification of DNA in large quantities. In particular, there is a need to provide improved methods for amplification of specific forms of DNA, such as closed linear DNAs. Closed linear DNA molecules have particular utility for therapeutic applications, as they have improved stability and safety over other forms of DNA.

SUMMARY OF THE INVENTION

The present invention relates to a process for in vitro, cell-free production of linear covalently closed DNA (closed linear DNA). The process allows for enhanced production of linear covalently closed DNA compared to current methodologies involving cellular processes and amplification within plasmids. This significantly increases process productivity while reducing the cost of product purification.

According to the present invention, production of linear covalently closed DNA from a DNA template is carried out enzymatically in the absence of a host cell. The template DNA comprises at least one protelomerase target sequence. The template DNA is contacted with at least one DNA polymerase in the presence of one or more primers under conditions promoting amplification of the template. DNA amplified from the template is contacted with at least one protelomerase under conditions promoting production of closed linear DNA.

Accordingly, the present invention provides an in vitro cell-free process for production of a closed linear deoxyribonucleic acid (DNA) comprising:

(a) contacting a DNA template comprising at least one protelomerase target sequence with at least one DNA polymerase in the presence of one or more primers under conditions promoting amplification of said template; and (b) contacting amplified DNA produced in (a) with at least one protelomerase under conditions promoting production of closed linear DNA.

The invention further relates to a kit providing components necessary in the process of the invention. Thus, the invention provides a kit comprising at least one DNA polymerase and at least one protelomerase and instructions for use in a process of the invention.

Figure 4:
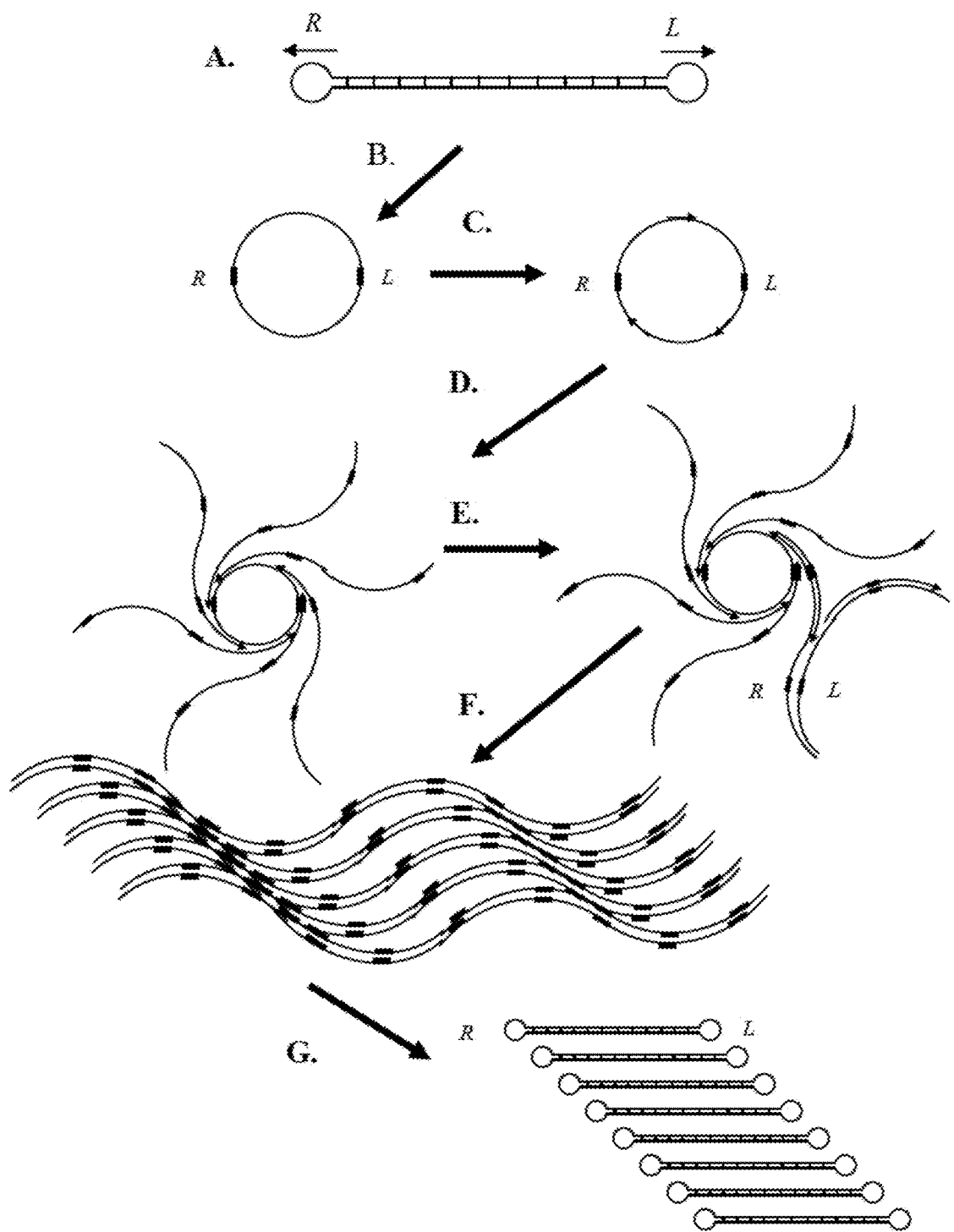

FIG. 4: Specific process for in vitro amplification of a linear double stranded covalently closed DNA using an RCA strand displacement DNA polymerase in combination with TelN protelomerase. A. Closed linear DNA template. R and L represent the DNA sequences of the right and left arms of the TelN protelomerase binding sequence. B. Denaturation of starting template to form circular single stranded DNA. C. Primer binding. D-E. Rolling circle amplification from single stranded DNA template by an RCA strand displacement DNA polymerase. F. Formation of long concatemeric double stranded DNA comprising single units of amplified template separated by protelomerase binding sequences (RL). G. Contacting with TelN protelomerase specific to RL sequence. Protelomerase cleaves concatameric DNA at RL site and ligates complementary strands to produce amplified copies of the original linear covalently closed DNA template.

Figure 5:
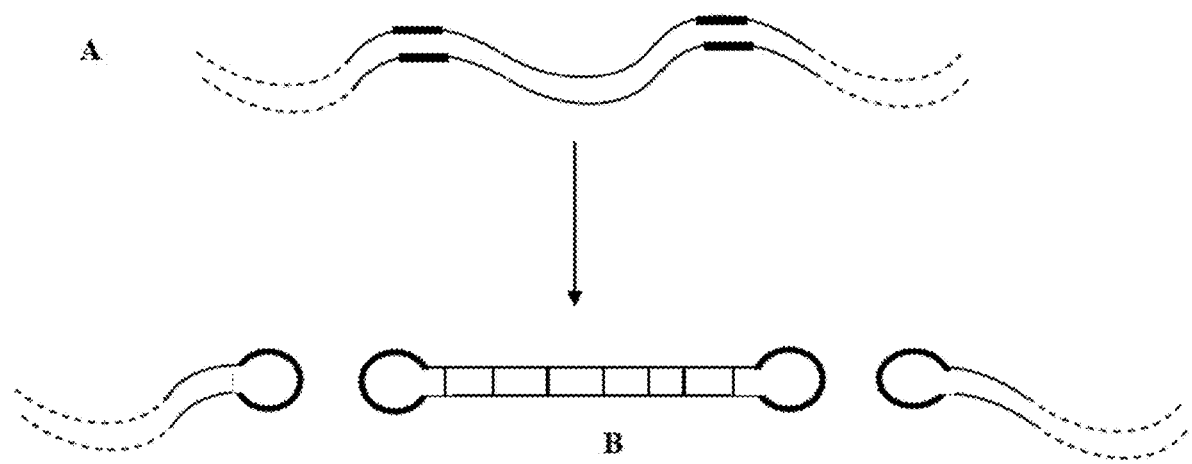

FIG. 5: Excision of DNA cassette expressing gene of interest from a long double stranded DNA molecule to create a closed linear DNA cassette. A. Linear double stranded DNA molecule containing a DNA cassette containing gene of interest flanked by protelomerase target sequences. B. Excision of the DNA cassette as a linear covalently closed DNA molecule.

Figure 6:
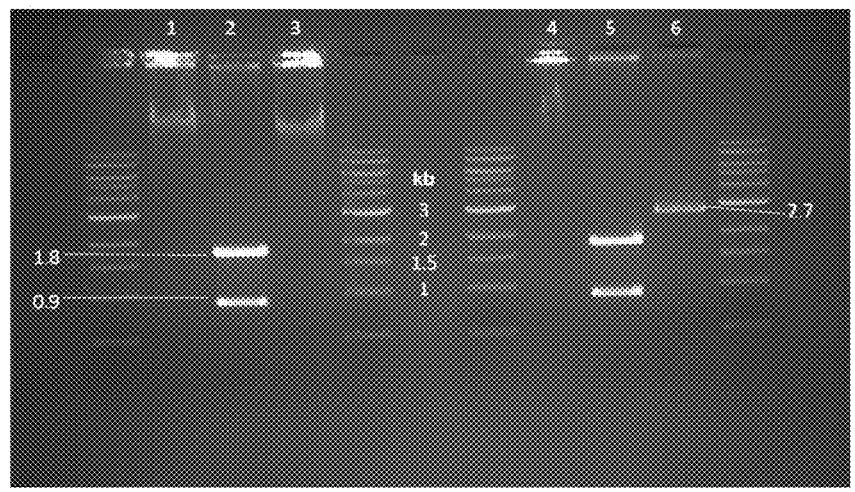
Figure 6:
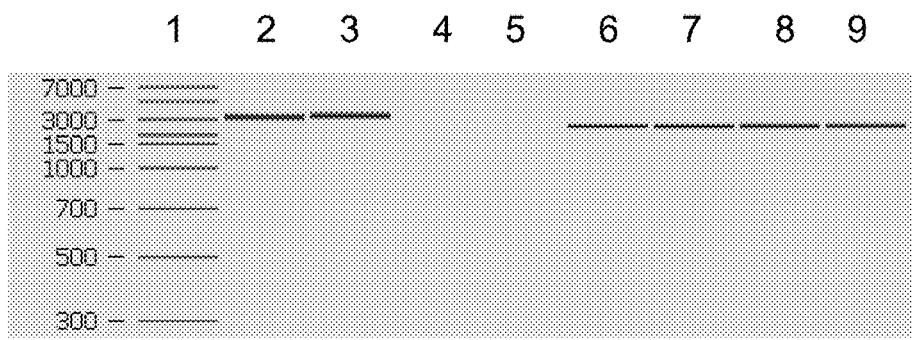
Figure 6:
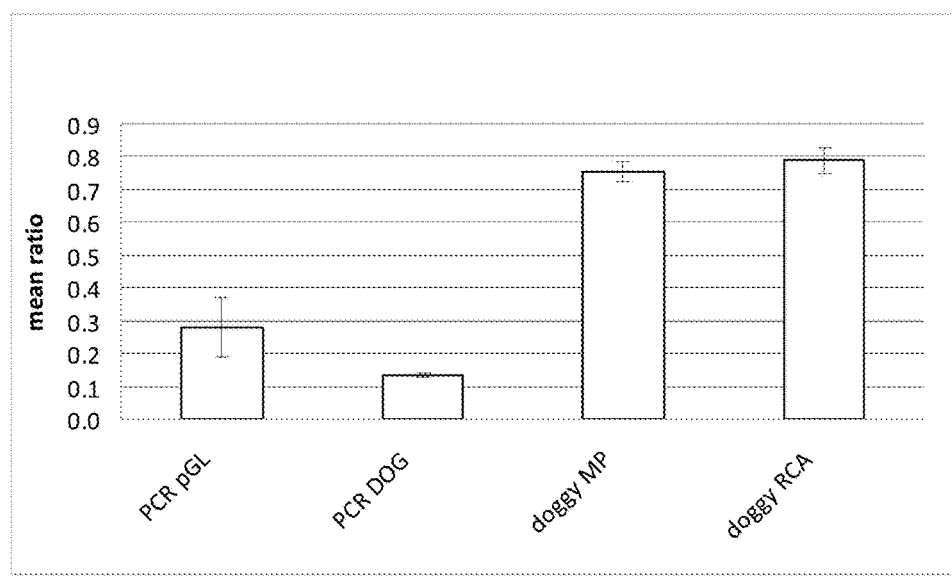

FIG. 6: Amplification of closed linear DNA and reporter gene expression for "doggybone" expression cassette.

A. Confirmation of TelN cleavage of RCA amplified concatamers to form closed linear DNA by agarose gel electrophoresis. Lanes 1 to 3 show RCA amplified pUC18. Lane 1: 3 microlitres undigested RCA amplified pUC18. Lane 2: 2 microlitres RCA amplified pUC18 digested with Pvu1. Lane 3: 2 microlitres RCA amplified pUC18 treated with TelN (negative control). Lanes 4 to 6 show RCA amplified pUC18 telRL. Lane 4: 3 microlitres undigested RCA amplified pUC18 telRL. Lane 5: 1 microlitre RCA amplified pUC18 telRL digested with Pvu1. Lane 6: 4 microlitres RCA amplified pUC18 telRL treated with TelN. The 2.7 kb closed linear DNA generated on treatment with TelN is indicated. Flanking lanes are DNA size markers.

B. Lab-On-A-Chip (LOC) analysis showing resistance of closed linear DNA to thermal denaturation. Lane 1: DNA size marker. Lanes 2 and 3: 100 ng PCR DOG. Lanes 4 and 5: 100 ng denatured PCR DOG. Lanes 6 and 7: "doggybone" DNA—100 ng pGL DOG treated with TelN. Lanes 6 and 7: "doggybone DNA"—100 ng pGL DOG treated with TelN and denatured.

C. Validation of expression of closed linear DNA in cells by transfection. y axis: mean Firefly/*Renilla* ratio; x-axis: linear DNA constructs used in transfection. PCR pGL: open linear PCR fragment from pGL4.13 across luc gene. PCR DOG: open linear PCR fragment amplified from pGL DOG using primers flanking the telRL sites. "doggy MP": closed linear DNA from pGL DOG isolated from mini-prep DNA digested with PvuI (to remove contaminating vector DNA) and cleaved with TelN. "doggy RCA": closed linear DNA from pGL DOG amplified by RCA digested with PvuI and cleaved with TelN.

Description of Sequences

SEQ ID NO:1 is the nucleic acid sequence of a *Bacillus* bacteriophage phi29 DNA polymerase.

SEQ ID NO: 2 is the amino acid sequence of a *Bacillus* bacteriophage phi29 DNA polymerase encoded by SEQ ID NO: 1.

SEQ ID NO: 3 is the amino acid sequence of a *Pyrococcus* sp Deep Vent DNA polymerase.

SEQ ID NO: 4 is the nucleic acid sequence of *Bacillus stearothermophilus* DNA polymerase I.

SEQ ID NO: 5 is the amino acid sequence of *Bacillus stearothermophilus* DNA polymerase I encoded by SEQ ID NO: 4.

SEQ ID NO: 6 is the nucleic acid sequence of a *Halomonas* phage phiHAP-1 protelomerase nucleic acid sequence.

SEQ ID NO: 7 is the amino acid sequence of a *Halomonas* phage phiHAP-1 protelomerase encoded by SEQ ID NO: 6.

SEQ ID NO: 8 is the nucleic acid sequence of a *Yersinia* phage PY54 protelomerase.

SEQ ID NO: 9 is the amino acid sequence of a *Yersinia* phage PY54 protelomerase encoded by SEQ ID NO: 8.

SEQ ID NO: 10 is the nucleic acid sequence of a *Klebsiella* phage phiKO2 protelomerase.

SEQ ID NO: 11 is the amino acid sequence of a *Klebsiella* phage phiKO2 protelomerase encoded by SEQ ID NO: 10.

SEQ ID NO: 12 is the nucleic acid sequence of a *Vibrio* phage VP882 protelomerase.

SEQ ID NO: 13 is the amino acid sequence of a *Vibrio* phage VP882 protelomerase encoded by SEQ ID NO: 12.

SEQ ID NO: 14 is the nucleic acid sequence of an *Escherichia coli* bacteriophage N15 protelomerase (telN) and secondary immunity repressor (cA) nucleic acid sequence.

SEQ ID NO: 15 is the amino acid sequence of an *Escherichia coli* bacteriophage N15 protelomerase (telN) encoded by SEQ ID NO: 14

SEQ ID NO: 16 is a consensus nucleic acid sequence for a perfect inverted repeat present in bacteriophage protelomerase target sequences.

SEQ ID NO: 17 is a 22 base perfect inverted repeat nucleic acid sequence from *E. coli* phage N15 and *Klebsiella* phage phiKO2.

SEQ ID NO: 18 is a 22 base perfect inverted repeat nucleic acid sequence from *Yersinia* phage PY54.

SEQ ID NO: 19 is a 22 base perfect inverted repeat nucleic acid sequence from *Halomonas* phage phiHAP-1.

SEQ ID NO: 20 is a 22 base perfect inverted repeat nucleic acid sequence from *Vibrio* phage VP882.

SEQ ID NO: 21 is a 14 base perfect inverted repeat nucleic acid sequence from *Borrelia burgdorferi* plasmid lpB31.16.

SEQ ID NO: 22 is a 24 base perfect inverted repeat nucleic acid sequence from *Vibrio* phage VP882.

SEQ ID NO: 23 is a 42 base perfect inverted repeat nucleic acid sequence from *Yersinia* phage PY54.

SEQ ID NO: 24 is a 90 base perfect inverted repeat nucleic acid sequence from *Halomonas* phage phiHAP-1.

SEQ ID NO: 25 is a nucleic acid sequence from *E. coli* phage N15 comprising a protelomerase target sequence.

SEQ ID NO: 26 is a nucleic acid sequence from *Klebsiella* phage phiKO2 comprising a protelomerase target sequence.

SEQ ID NO: 27 is a nucleic acid sequence from *Yersinia* phage PY54 comprising a protelomerase target sequence.

SEQ ID NO: 28 is a nucleic acid sequence from *Vibrio* phage VP882 comprising a protelomerase target sequence.

SEQ ID NO: 29 is a nucleic acid sequence from *Borrelia burgdorferi* plasmid lpB31.16 comprising a protelomerase target sequence.

SEQ ID NO: 30 is a modified oligonucleotide primer used in amplification of TelN.

SEQ ID NO: 31 is a modified oligonucleotide primer used in amplification of TelN. SEQ ID NO: 32 is a synthetic oligonucleotide containing the TelN recognition site telRL.

SEQ ID NO: 33 is a synthetic oligonucleotide containing the TelN recognition site telRL.

SEQ ID NO: 34 is a primer sequence used in amplification of PCR DOG.

SEQ ID NO: 35 is a primer sequence used in amplification of PCR DOG.

DETAILED DESCRIPTION OF THE INVENTION

Figure 1:
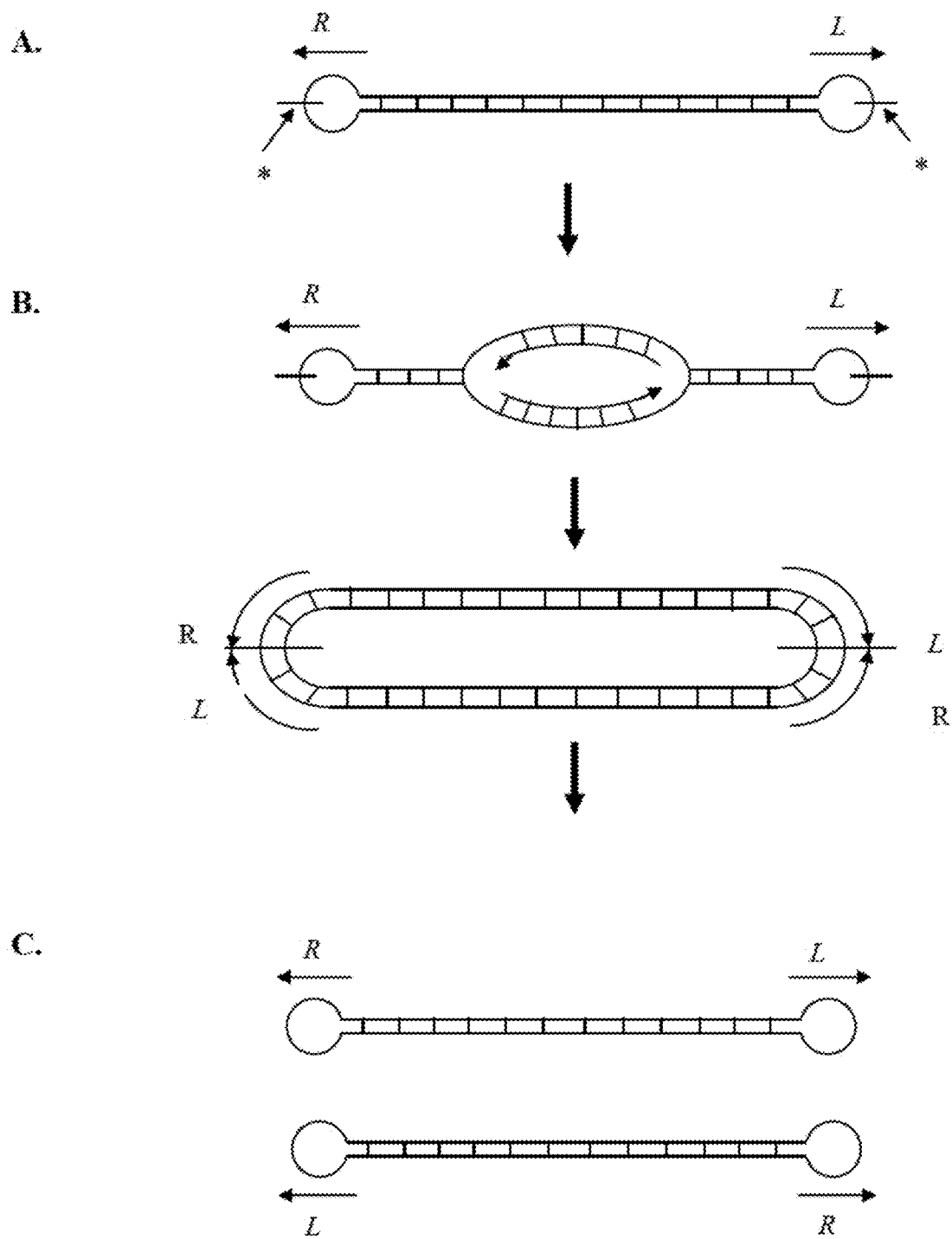
FIG. 1: Replication of linear covalently closed DNA in bacteriophages and the role of protelomerase. A. Depiction of extrachromosomal bacteriophage linear covalently closed DNA. *=Centre of palindromic sequence of telomere. The R sequence is an inverted palindromic repeat of the L sequence. B. Replication of bacteriophage DNA in host: Bubble indicates DNA strand replication. Synthesis of the complementary strand to R and L leads to identical double stranded RL sequences. C. Products formed by action of protelomerase. Protelomerase binds to the RL sequence and cuts and ligates the opposite strands at the centre point of the palindromic sequence to reform the telomeres and complete the replication of the original linear covalently closed DNA.

The present invention relates to processes for the production of linear double stranded covalently closed DNA i.e closed linear DNA molecules. Closed linear DNA molecules typically comprise covalently closed ends also described as hairpin loops, where base-pairing between complementary DNA strands is not present. The hairpin loops join the ends of complementary DNA strands. Structures of this type typically form at the telomeric ends of chromosomes in order to protect against loss or damage of chromosomal DNA by sequestering the terminal nucleotides in a closed structure. In examples of closed linear DNA molecules described herein, hairpin loops flank complementary base-paired DNA strands, forming a "doggy-bone" shaped structure (as shown in FIG. 1).

The processes of the present invention provide for high throughput production of closed linear DNA molecules by incorporating a single processing step converting amplified DNA into closed linear DNA. In addition, the processes of the present invention are carried out in an in vitro cell-free environment, and as such are not limited to use of DNA templates having extraneous sequences necessary for bacterial propagation. As outlined below, the process of the invention can therefore be used to produce closed linear DNA molecules which lack problematic vector sequences and are particularly suitable for therapeutic uses.

Closed DNA molecules have particular utility as therapeutic agents i.e. DNA medicines which can be used to express a gene product in vivo. This is because their covalently closed structure prevents attack by enzymes such as exonucleases, leading to enhanced stability and longevity of gene expression as compared to "open" DNA molecules with exposed DNA ends. Linear double stranded open-ended cassettes have been demonstrated to be inefficient with respect to gene expression when introduced into host tissue. This has been attributed to cassette instability due to the action of exonucleases in the extracellular space.

Sequestering DNA ends inside covalently closed structures also has other advantages. The DNA ends are prevented from integrating with genomic DNA and so closed linear DNA molecules are of improved safety. Also, the closed linear structure prevents concatamerisation of DNA molecules inside host cells and thus expression levels of the gene product can be regulated in a more sensitive manner. The present invention provides an in vitro cell-free process for production of closed linear DNA molecules that comprises template-directed DNA amplification, and specific processing of amplified DNA by protelomerase.

Typically, the process of the invention may be used for production of DNA for in vitro expression in a host cell, particularly in DNA vaccines. DNA vaccines typically encode a modified form of an infectious organism's DNA. DNA vaccines are administered to a subject where they then express the selected protein of the infectious organism, initiating an immune response against that protein which is typically protective. DNA vaccines may also encode a tumour antigen in a cancer immunotherapy approach.

A DNA vaccine may comprise a nucleic acid sequence encoding an antigen for the treatment or prevention of a number of conditions including but not limited to cancer, allergies, toxicity and infection by a pathogen such as, but not limited to, fungi, viruses including Human Papilloma Viruses (HPV), HIV, HSV2/HSV1, Influenza virus (types A, B and C), Polio virus, RSV virus, Rhinoviruses, Rotaviruses, Hepatitis A virus, Norwalk Virus Group, Enteroviruses, Astroviruses, Measles virus, Parainfluenza virus, Mumps virus, Varicella-Zoster virus, Cytomegalovirus, Epstein-Barr virus, Adenoviruses, Rubella virus, Human T-cell Lymphoma type I virus (HTLV-I), Hepatitis B virus (HBV), Hepatitis C virus (HCV), Hepatitis D virus, Pox virus, Marburg and Ebola; bacteria including *Mycobacterium tuberculosis, Chlamydia, Neisseria gonorrhoeae, Shigella, Salmonella, Vibrio cholerae, Treponema pallidum, Pseudomonas, Bordetella pertussis, Brucella, Franciscella tularensis, Helicobacter pylori, Leptospira interrogans, Legionella pneumophila, Yersinia pestis, Streptococcus* (types A and B), *Pneumococcus, Meningococcus, Haemophilus influenza* (type b), *Toxoplasma gondii, Campylobacteriosis, Moraxella catarrhalis, Donovanosis,* and *Actinomycosis*; fungal pathogens including Candidiasis and Aspergillosis; parasitic pathogens including *Taenia*, Flukes, Roundworms, Amoebiasis, Giardiasis, *Cryptosporidium, Schistosoma, Pneumocystis carinii, Trichomoniasis* and *Trichinosis*.

DNA vaccines may comprise a nucleic acid sequence encoding an antigen from a member of the adenoviridae (including for instance a human adenovirus), herpesviridae (including for instance HSV-1, HSV-2, EBV, CMV and VZV), papovaviridae (including for instance HPV), poxviridae (including for instance smallpox and vaccinia), parvoviridae (including for instance parvovirus B19), reoviridae (including for instance a rotavirus), coronaviridae (including for instance SARS), flaviviridae (including for instance yellow fever, West Nile virus, dengue, hepatitis C and tick-borne encephalitis), picornaviridae (including polio, rhinovirus, and hepatitis A), togaviridae (including for instance rubella virus), filoviridae (including for instance Marburg and Ebola), paramyxoviridae (including for instance a parainfluenza virus, respiratory syncitial virus, mumps and measles), rhabdoviridae (including for instance rabies virus), bunyaviridae (including for instance Hantaan virus), orthomyxoviridae (including for instance influenza A, B and C viruses), retroviridae (including for instance HIV and HTLV) and hepadnaviridae (including for instance hepatitis B).

The antigen may be from a pathogen responsible for a veterinary disease and in particular may be from a viral pathogen, including, for instance, a Reovirus (such as African Horse sickness or Bluetongue virus) and Herpes viruses (including equine herpes). The antigen may be one from Foot and Mouth Disease virus, Tick borne encephalitis virus, dengue virus, SARS, West Nile virus and Hantaan virus. The antigen may be from an immunodeficiency virus, and may, for example, be from SIV or a feline immunodeficiency virus.

DNA vaccines produced by the process of the invention may also comprise a nucleic acid sequence encoding tumour antigens. Examples of tumour associated antigens include, but are not limited to, cancer-testes antigens such as members of the MAGE family (MAGE 1, 2, 3 etc), NY-ESO-1 and SSX-2, differentiation antigens such as tyrosinase, gp100, PSA, Her-2 and CEA, mutated self antigens and viral tumour antigens such as E6 and/or E7 from oncogenic HPV types. Further examples of particular tumour antigens include MART-1, Melan-A, p97, beta-HCG, GalNAc, MAGE-1, MAGE-2, MAGE-4, MAGE-12, MUC1, MUC2, MUC3, MUC4, MUC18, CEA, DDC, P1A, EpCam, melanoma antigen gp75, Hker 8, high molecular weight melanoma antigen, K19, Tyrl, Tyr2, members of the pMel 17 gene family, c-Met, PSM (prostate mucin antigen), PSMA (prostate specific membrane antigen), prostate secretary protein, alpha-fetoprotein, CA125, CA19.9, TAG-72, BRCA-1 and BRCA-2 antigen.

Also, the process of the invention may produce other types of therapeutic DNA molecules e.g. those used in gene therapy. For example, such DNA molecules can be used to express a functional gene where a subject has a genetic disorder caused by a dysfunctional version of that gene. Examples of such diseases include Duchenne muscular dystrophy, cystic fibrosis, Gaucher's Disease, and adenosine deaminase (ADA) deficiency. Other diseases where gene therapy may be useful include inflammatory diseases, autoimmune, chronic and infectious diseases, including such disorders as AIDS, cancer, neurological diseases, cardivascular disease, hypercholestemia, various blood disorders including various anaemias, thalassemia and haemophilia, and emphysema. For the treatment of solid tumors, genes encoding toxic peptides (i.e., chemotherapeutic agents such as ricin, diptheria toxin and cobra venom factor), tumor suppressor genes such as p53, genes coding for mRNA sequences which are antisense to transforming oncogenes, antineoplastic peptides such as tumor necrosis factor (TNF) and other cytokines, or transdominant negative mutants of transforming oncogenes, may be expressed.

Other types of therapeutic DNA molecules are also contemplated for production by the process of the invention. For example, DNA molecules which are transcribed into an active RNA form, for example a small interfering RNA (siRNA) may be produced according to the process of the invention.

In embodiments directed to production of DNA molecules having therapeutic utility, the DNA template will typically comprise an expression cassette comprising one or more promoter or enhancer elements and a gene or other coding sequence which encodes an mRNA or protein of interest. In particular embodiments directed to generation of DNA vaccine molecules or DNA molecules for gene therapy, the DNA template comprises an expression cassette consisting of a eukaryotic promoter operably linked to a sequence encoding a protein of interest, and optionally an enhancer and/or a eukaryotic transcription termination sequence. Typically, the DNA template may be in the form of a vector commonly used to house a gene e.g. an extrachromosomal genetic element such as a plasmid.

A "promoter" is a nucleotide sequence which initiates and regulates transcription of a polynucleotide. Promoters can include inducible promoters (where expression of a polynucleotide sequence operably linked to the promoter is induced by an analyte, cofactor, regulatory protein, etc.), repressible promoters (where expression of a polynucleotide sequence operably linked to the promoter is repressed by an analyte, cofactor, regulatory protein, etc.), and constitutive promoters. It is intended that the term "promoter" or "control element" includes full-length promoter regions and functional (e.g., controls transcription or translation) segments of these regions.

"Operably linked" refers to an arrangement of elements wherein the components so described are configured so as to perform their usual function. Thus, a given promoter operably linked to a nucleic acid sequence is capable of effecting the expression of that sequence when the proper enzymes are present. The promoter need not be contiguous with the sequence, so long as it functions to direct the expression thereof. Thus, for example, intervening untranslated yet transcribed sequences can be present between the promoter sequence and the nucleic acid sequence and the promoter sequence can still be considered "operably linked" to the coding sequence. Thus, the term "operably linked" is intended to encompass any spacing or orientation of the promoter element and the DNA sequence of interest which allows for initiation of transcription of the DNA sequence of interest upon recognition of the promoter element by a transcription complex.

According to the present invention, closed linear DNA molecules are generated by the action of protelomerase on DNA amplified from a DNA template comprising at least one protelomerase target sequence. A protelomerase target sequence is any DNA sequence whose presence in a DNA template allows for its conversion into a closed linear DNA by the enzymatic activity of protelomerase. In other words, the protelomerase target sequence is required for the cleavage and religation of double stranded DNA by protelomerase to form covalently closed linear DNA.

Figure 2:
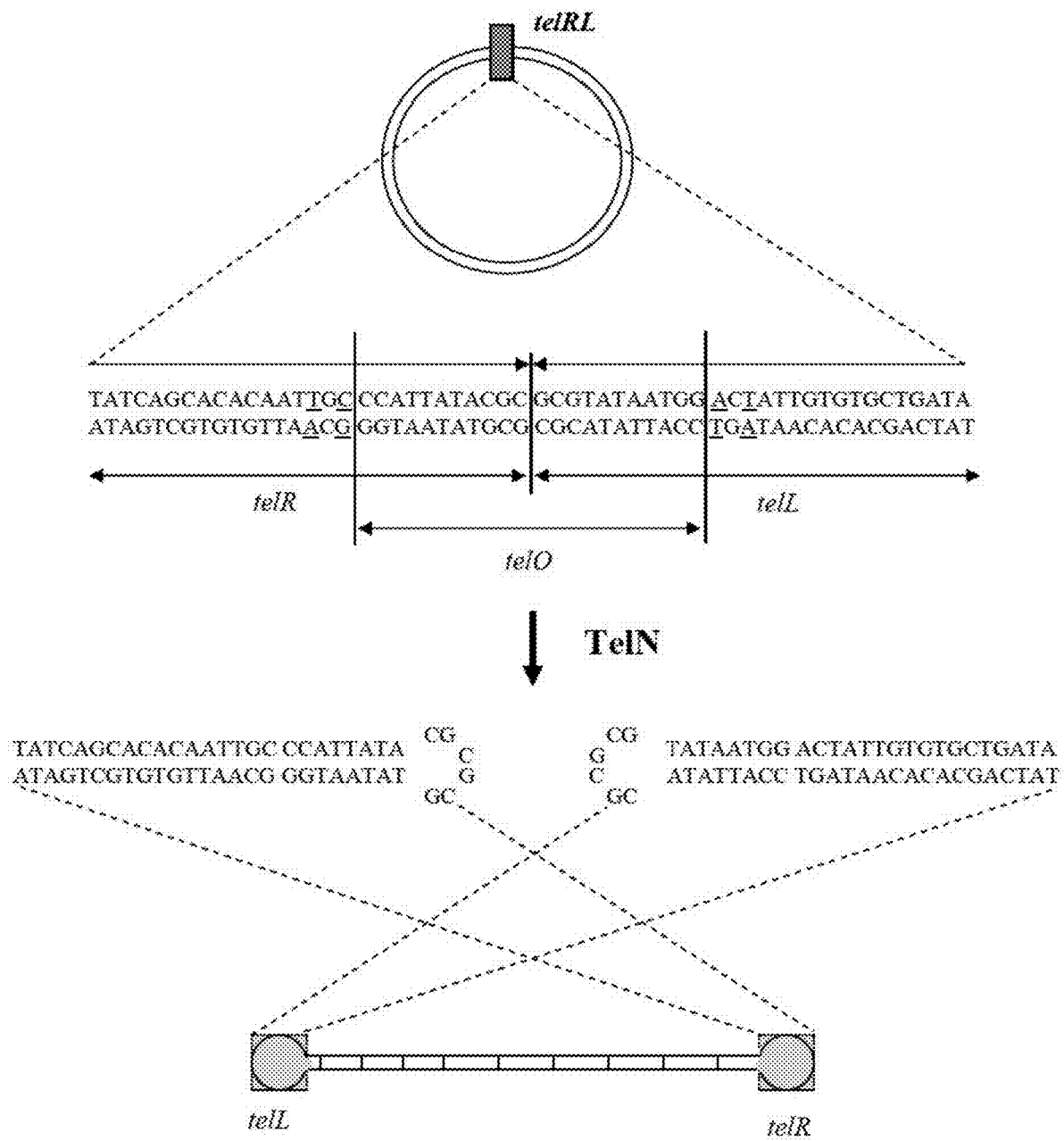
FIG. 2: The action of *Escherichia coli* phage N15 protelomerase (TelN) on circular double stranded DNA containing its target site, telRL. TelRL is an inverted palindrome with 28 bp right (telR) (SEQ ID NO:37) and left (telL) (SEQ ID NO:38) arms indicated by the arrows. The sequences underlined indicate imperfections in the telRL palindrome. A central 22 bp perfect inverted palindrome TelO (SEQ ID NO:17) is required for the binding of the enzyme, TelN. TelN cleaves this 22 bp sequence at its mid-point and joins the ends of the complementary strands to form covalently closed ends.
Figure 3:
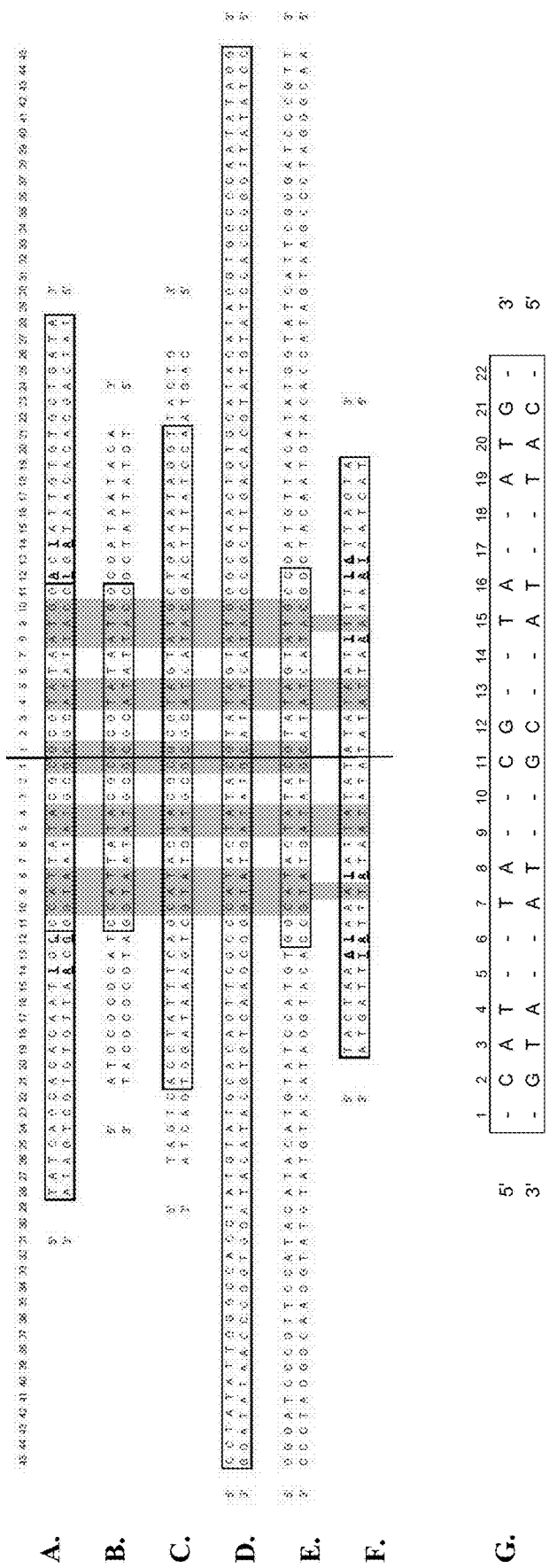
FIG. 3: Comparison of protelomerase target sequences in found in various organisms. The boxed sequences show the extent of perfect or imperfect palindromic sequence. Underlining shows imperfections in the palindrome. The base pair sequences highlighted are common to all protelomerase target sequences indicating their importance to protelomerase binding and action. A. *Escherichia coli* phage N15 (SEQ ID NO:25). B. *klebsiella* phage Phi KO2 (SEQ ID NO:26). C. *yersinia* phage Py54 (SEQ ID NO:27). D. *halomonas* phage Phi HAP (SEQ ID NO:24). E. *vibrio* phage VP882 (SEQ ID NO:28). F. *Borrelia burgdorferi* plasmid lpB31.16 (SEQ ID NO:29). The boxed sequences show the extent of perfect or imperfect palindromic sequence for each bacteriophage. G. The consensus inverse palindromic sequence for bacteriophage protelomerase binding and action is shown in SEQ ID NO:16. This is a 22 base pair perfect inverted repeat sequence (11 base pairs either side of the cut site). The consensus sequence is derived from the conserved highlighted residues shown for A-E. Conserved base pairs and their positions in the palindrome are indicated. Dashes indicate flexibility in sequence composition i.e. where bases may be N (A, T, C or G).

Typically, a protelomerase target sequence comprises any perfect palindromic sequence i.e any double-stranded DNA sequence having two-fold rotational symmetry, also described herein as a perfect inverted repeat. As shown in FIG. 3, the protelomerase target sequences from various mesophilic bacteriophages, and a bacterial plasmid all share the common feature of comprising a perfect inverted repeat. The length of the perfect inverted repeat differs depending on the specific organism. In *Borrelia burgdorferi*, the perfect inverted repeat is 14 base pairs in length. In various mesophilic bacteriophages, the perfect inverted repeat is 22 base pairs or greater in length. Also, in some cases, e.g *E. coli* N15, the central perfect inverted palindrome is flanked by inverted repeat sequences, i.e forming part of a larger imperfect inverted palindrome (see FIGS. 2 and 3; the underlined bases indicate where the symmetry of the inverted repeats is interrupted).

A protelomerase target sequence as used in the invention preferably comprises a double stranded palindromic (perfect inverted repeat) sequence of at least 14 base pairs in length. Preferred perfect inverted repeat sequences include the sequences of SEQ ID NOs: 16 to 21 and variants thereof. SEQ ID NO: 16 (NCATNNTANNCGNNTANNATGN) is a 22 base consensus sequence for a mesophilic bacteriophage perfect inverted repeat. As shown in FIG. 3, base pairs of the perfect inverted repeat are conserved at certain positions between different bacteriophages, while flexibility in sequence is possible at other positions. Thus, SEQ ID NO: 16 is a minimum consensus sequence for a perfect inverted repeat sequence for use with a bacteriophage protelomerase in the process of the present invention.

Within the consensus defined by SEQ ID NO: 16, SEQ ID NO: 17 (CCATTATACGCGCGTATAATGG) is a particularly preferred perfect inverted repeat sequence for use with *E. coli* phage N15 (SEQ ID NO: 15), and *Klebsiella* phage Phi KO2 (SEQ ID NO: 11) protelomerases. Also within the consensus defined by SEQ ID NO: 16, SEQ ID NOs: 18 to 20:

SEQ ID NO: 18
(GCATACTACGCGCGTAGTATGC),

SEQ ID NO: 19
(CCATACTATACGTATAGTATGG),

SEQ ID NO: 20
(GCATACTATACGTATAGTATGC), are particularly preferred perfect inverted repeat sequences for use respectively with protelomerases from *Yersinia* phage PY54 (SEQ ID NO: 9), *Halomonas* phage phiHAP-1 (SEQ ID NO: 7), and *Vibrio* phage VP882 (SEQ ID NO: 13). SEQ ID NO: 21 (ATTATATATATAAT) is a particularly preferred perfect inverted repeat sequence for use with a *Borrelia burgdorferi* protelomerase. This perfect inverted repeat sequence is from a linear covalently closed plasmid, lpB31.16 comprised in *Borrelia burgdorferi*. This 14 base sequence is shorter than the 22 bp consensus perfect inverted repeat for bacteriophages (SEQ ID NO: 16), indicating that bacterial protelomerases may differ in specific target sequence requirements to bacteriophage protelomerases. However, all protelomerase target sequences share the common structural motif of a perfect inverted repeat.

The perfect inverted repeat sequence may be greater than 22 bp in length depending on the requirements of the specific protelomerase used in the process of the invention. Thus, in some embodiments, the perfect inverted repeat may be at least 30, at least 40, at least 60, at least 80 or at least 100 base pairs in length. Examples of such perfect inverted repeat sequences include SEQ ID NOs: 22 to 24 and variants thereof.

SEQ ID NO: 22
(GGCATACTATACGTATAGTATGCC)

SEQ ID NO: 23
(ACCTATTTCAGCATACTACGCGCGTAGTATGCTGAAATAGGT)

SEQ ID NO: 24
(CCTATATTGGGCCACCTATGTATGCACAGTTCGCCCATACTATACGTAT

AGTATGGGCGAACTGTGCATACATAGGTGGCCCAATATAGG)

SEQ ID NOs: 22 to 24 and variants thereof are particularly preferred for use respectively with protelomerases from *Vibrio* phage VP882 (SEQ ID NO: 13), *Yersinia* phage PY54 (SEQ ID NO: 9) and *Halomonas* phage phi HAP-1 (SEQ ID NO: 7).

The perfect inverted repeat may be flanked by additional inverted repeat sequences. The flanking inverted repeats may be perfect or imperfect repeats i.e may be completely symmetrical or partially symmetrical. The flanking inverted repeats may be contiguous with or non-contiguous with the central palindrome. The protelomerase target sequence may comprise an imperfect inverted repeat sequence which comprises a perfect inverted repeat sequence of at least 14 base pairs in length. An example is SEQ ID NO: 29. The imperfect inverted repeat sequence may comprise a perfect inverted repeat sequence of at least 22 base pairs in length. An example is SEQ ID NO: 25.

Particularly preferred protelomerase target sequences comprise the sequences of SEQ ID NOs: 25 to 29 or variants thereof.

SEQ ID NO: 25:
(TATCAGCACACAATTGCCCATTATACGCGCGTATAATGGACTATTGTGT

GCTGATA)

SEQ ID NO: 26
(ATGCGCGCATCCATTATACGCGCGTATAATGGCGATAATACA)

SEQ ID NO: 27
(TAGTCACCTATTTCAGCATACTACGCGCGTAGTATGCTGAAATAGGTTA

CTG)

SEQ ID NO: 28:
(GGGATCCCGTTCCATACATACATGTATCCATGTGGCATACTATACGTAT

AGTATGCCGATGTTACATATGGTATCATTCGGGATCCCGTT)

SEQ ID NO: 29
(TACTAAATAAATATTATATATATAATTTTTTATTAGTA)

The sequences of SEQ ID NOs: 25 to 29 comprise perfect inverted repeat sequences as described above, and additionally comprise flanking sequences from the relevant organisms. A protelomerase target sequence comprising the sequence of SEQ ID NO: 25 or a variant thereof is preferred for use in combination with *E. coli* N15 TelN protelomerase of SEQ ID NO: 15 and variants thereof. A protelomerase target sequence comprising the sequence of SEQ ID NO: 26 or a variant thereof is preferred for use in combination with *Klebsiella* phage Phi K02 protelomerase of SEQ ID NO: 11 and variants thereof. A protelomerase target sequence comprising the sequence of SEQ ID NO: 27 or a variant thereof is preferred for use in combination with *Yersinia* phage PY54 protelomerase of SEQ ID NO: 9 and variants thereof. A protelomerase target sequence comprising the sequence of SEQ ID NO: 28 or a variant thereof is preferred for use in combination with *Vibrio* phage VP882 protelomerase of SEQ ID NO: 13 and variants thereof. A protelomerase target sequence comprising the sequence of SEQ ID NO: 29 or a variant thereof is preferred for use in combination with a *Borrelia burgdorferi* protelomerase.

Variants of any of the palindrome or protelomerase target sequences described above include homologues or mutants thereof. Mutants include truncations, substitutions or deletions with respect to the native sequence. A variant sequence is any sequence whose presence in the DNA template allows for its conversion into a closed linear DNA by the enzymatic activity of protelomerase. This can readily be determined by use of an appropriate assay for the formation of closed linear DNA. Any suitable assay described in the art may be used. An example of a suitable assay is described in Deneke et al, PNAS (2000) 97, 7721-7726. Preferably, the variant allows for protelomerase binding and activity that is comparable to that observed with the native sequence. Examples of preferred variants of palindrome sequences described herein include truncated palindrome sequences that preserve the perfect repeat structure, and remain capable of allowing for formation of closed linear DNA. However, variant protelomerase target sequences may be modified such that they no longer preserve a perfect palindrome, provided that they are able to act as substrates for protelomerase activity.

It should be understood that the skilled person would readily be able to identify suitable protelomerase target sequences for use in the invention on the basis of the structural principles outlined above. Candidate protelomerase target sequences can be screened for their ability to promote formation of closed linear DNA using the assays described above.

The DNA template may comprise more than one protelomerase target sequence, for example, two, three, four, five, ten or more protelomerase target sequences. Use of multiple protelomerase target sequences can allow for excision of short closed linear DNAs comprising sequences of interest from a larger DNA molecule. In particular, one or more sequences of interest in the DNA template may be flanked on either side (i.e 5' and 3') by a protelomerase target sequence. The two flanking protelomerase sequences can then mediate excision of each short sequence of interest from the amplified DNA as a closed linear DNA, subject to the action of protelomerase (as shown in FIG. 5). The DNA template may comprise one or more sequences of interest (preferably expression cassettes) flanked on either side by protelomerase target sequences. The DNA template may comprise two, three, four, five or more sequences of interest flanked by protelomerase target sequences as described above.

In a preferred embodiment, the process of the invention uses a DNA template comprising an expression cassette flanked on either side by a protelomerase target sequence. The expression cassette preferably comprises a eukaryotic promoter operably linked to a coding sequence of interest, and optionally a eukaryotic transcription termination sequence. In this embodiment, following amplification of the template DNA, and contacting with protelomerase according to the invention, the expression cassette is released from the amplified template as a closed linear DNA. Unnecessary sequences in the template DNA are concomitantly deleted as a result from the product.

Such unnecessary or extraneous sequences (also described as bacterial or vector sequences) may include bacterial origins of replication, bacterial selection markers (e.g antibiotic resistance genes), and unmethylated CpG dinucleotides. Deletion of such sequences creates a "minimal" expression cassette which does not contain extraneous genetic material. Also, bacterial sequences of the type described above can be problematic in some therapeutic approaches. For example, within a mammalian cell, bacterial/plasmid DNA can cause the cloned gene to switch off such that sustained expression of the protein of interest cannot be achieved. Also, antibiotic resistance genes used in bacterial propagation can cause a risk to human health. Furthermore, bacterial plasmid/vector DNA may trigger an unwanted non-specific immune response. A specific characteristic of bacterial DNA sequences, the presence of unmethylated cytosine-guanine dinucleotides, typically known as CpG motifs, may also lead to undesired immune responses.

In some embodiments, particularly where the closed linear DNA product is a DNA vaccine, CpG motifs may be retained in the sequence of the product. This is because they can have a beneficial adjuvant effect on the immune response to the encoded protein.

Thus, the invention provides an in vitro process for the production of a closed linear expression cassette DNA. This process comprises a) contacting a DNA template comprising at least one expression cassette flanked on either side by a protelomerase target sequence with at least one DNA polymerase in the presence of one or more primers under conditions promoting amplification of said template; and b) contacting amplified DNA produced in a) with at least one protelomerase under conditions promoting formation of a closed linear expression cassette DNA. The closed linear expression cassette DNA product may comprise, consist or consist essentially of a eukaryotic promoter operably linked to a coding sequence of interest, and optionally a eukaryotic transcription termination sequence. The closed linear expression cassette DNA product may additionally lack one or more bacterial or vector sequences, typically selected from the group consisting of: (i) bacterial origins of replication; (ii) bacterial selection markers (typically antibiotic resistance genes) and (iii) unmethylated CpG motifs.

As outlined above, any DNA template comprising at least one protelomerase target sequence may be amplified according to the process of the invention. Thus, although production of DNA vaccines and other therapeutic DNA molecules is preferred, the process of the invention may be used to produce any type of closed linear DNA. The DNA template may be a double stranded (ds) or a single stranded (ss) DNA. A double stranded DNA template may be an open circular double stranded DNA, a closed circular double stranded DNA, an open linear double stranded DNA or a closed linear double stranded DNA. Preferably, the template is a closed circular double stranded DNA. Closed circular dsDNA templates are particularly preferred for use with RCA DNA polymerases. A circular dsDNA template may be in the form of a plasmid or other vector typically used to house a gene for bacterial propagation. Thus, the process of the invention may be used to amplify any commercially available plasmid or other vector, such as a commercially available DNA medicine, and then convert the amplified vector DNA into closed linear DNA.

An open circular dsDNA may be used as a template where the DNA polymerase is a strand displacement polymerase which can initiate amplification from at a nicked DNA strand. In this embodiment, the template may be previously incubated with one or more enzymes which nick a DNA strand in the template at one or more sites. A closed linear dsDNA may also be used as a template. The closed linear dsDNA template (starting material) may be identical to the closed linear DNA product. Where a closed linear DNA is used as a template, it may be incubated under denaturing conditions to form a single stranded circular DNA before or during conditions promoting amplification of the template DNA.

As outlined above, the DNA template typically comprises an expression cassette as described above, i.e comprising, consisting or consisting essentially of a eukaryotic promoter operably linked to a sequence encoding a protein of interest, and optionally a eukaryotic transcription termination sequence. Optionally the expression cassette may be a minimal expression cassette as defined above, i.e lacking one or more bacterial or vector sequences, typically selected from the group consisting of: (i) bacterial origins of replication; (ii) bacterial selection markers (typically antibiotic resistance genes) and (iii) unmethylated CpG motifs.

The DNA template may be provided in an amount sufficient for use in the process by any method known in the art. For example, the DNA template may be produced by the polymerase chain reaction (PCR). Where the DNA template is a dsDNA, it may be provided for the amplification step as denatured single strands by prior incubation at a temperature of at least 94 degrees centigrade. Thus, the process of the invention preferably comprises a step of denaturing a dsDNA template to provide single stranded DNA. Alternatively, the dsDNA template may be provided in double-stranded form. The whole or a selected portion of the DNA template may be amplified in the reaction.

The DNA template is contacted with at least one DNA polymerase under conditions promoting amplification of said template. Any DNA polymerase may be used. Any commercially available DNA polymerase is suitable for use in the process of the invention. Two, three, four, five or more different DNA polymerases may be used, for example one which provides a proof reading function and one or more others which do not. DNA polymerases having different mechanisms may be used e.g strand displacement type polymerases and DNA polymerases replicating DNA by other methods. A suitable example of a DNA polymerase that does not have strand displacement activity is T4 DNA polymerase.

It is preferred that a DNA polymerase is highly stable, such that its activity is not substantially reduced by prolonged incubation under process conditions. Therefore, the enzyme preferably has a long half-life under a range of process conditions including but not limited to temperature and pH. It is also preferred that a DNA polymerase has one or more characteristics suitable for a manufacturing process. The DNA polymerase preferably has high fidelity, for example through having proof-reading activity. Furthermore, it is preferred that a DNA polymerase displays high processivity, high strand-displacement activity and a low Km for dNTPs and DNA. A DNA polymerase may be capable of using circular and/or linear DNA as template. The DNA polymerase may be capable of using dsDNA or ssDNA as a template. It is preferred that a DNA polymerase does not display non-specific exonuclease activity.

The skilled person can determine whether or not a given DNA polymerase displays characteristics as defined above by comparison with the properties displayed by commercially available DNA polymerases, e.g phi29, DeepVent® and *Bacillus stearothermophilus* (Bst) DNA polymerase I, SEQ ID NOs: 2, 3 and 5 respectively. Bst DNA polymerase I is commercially available from New England Biolabs, Inc. Where a high processivity is referred to, this typically denotes the average number of nucleotides added by a DNA polymerase enzyme per association/dissociation with the template, i.e the length of primer extension obtained from a single association event.

Strand displacement-type polymerases are preferred. Preferred strand displacement-type polymerases are Phi 29 (SEQ ID NO: 2), Deep Vent® (SEQ ID NO: 3) and Bst DNA polymerase I (SEQ ID NO: 5) or variants of any thereof. Variants of SEQ ID NOs: 2, 3 and 5 may be as defined below in relation to protelomerase enzymes. The term "strand displacement" is used herein to describe the ability of a DNA polymerase to displace complementary strands on encountering a region of double stranded DNA during DNA synthesis. It should be understood that strand displacement amplication methods differ from PCR-based methods in that cycles of denaturation are not essential for efficient DNA amplification, as double-stranded DNA is not an obstacle to continued synthesis of new DNA strands. In contrast, PCR methods require cycles of denaturation (i.e elevating temperature to 94 degrees centigrade or above) during the amplification process to melt double-stranded DNA and provide new single stranded templates.

A strand displacement DNA polymerase used in the method of the invention preferably has a processivity (primer extension length) of at least 20 kb, more preferably, at least 30 kb, at least 50 kb, or at least 70 kb or greater. In particularly preferred embodiments, the strand displacement DNA polymerase has a processivity that is comparable to, or greater than phi29 DNA polymerase.

A preferred strand displacement replication process is rolling circle amplification (RCA). The term RCA describes the ability of RCA-type DNA polymerases (also referred to herein as RCA polymerases) to continuously progress around a circular DNA template strand whilst extending a hybridised primer. This leads to formation of linear single stranded products with multiple repeats of amplified DNA. These linear single stranded products serve as the basis for multiple hybridisation, primer extension and strand displacement events, resulting in formation of concatameric double stranded DNA products, again comprising multiple repeats of amplified DNA. There are thus multiple copies of each amplified "single unit" DNA in the concatameric double stranded DNA products.

RCA polymerases are particularly preferred for use in the process of the present invention. The products of RCA-type strand displacement replication processes conventionally require complex processing to release single unit DNAs. Beneficially, according to the present invention, use of protelomerase catalytic functions allows this processing to be carried out in a single step. The use of protelomerase also directly generates the desired closed linear DNA structure without need for additional processing step(s) to form molecules having this structure.

In order to allow for amplification according to the invention, it is preferred that the DNA template is also contacted with one or more primers. The primers may be non-specific (i.e random in sequence) or may be specific for one or more sequences comprised within the DNA template. It is preferred that the primers are of random sequence so as to allow for non-specific initiation at any site on the DNA template. This allows for high efficiency of amplification through multiple initiation reactions from each template strand. Examples of random primers are hexamers, heptamers, octamers, nonamers, decamers or sequences greater in length, for example of 12, 15, 18, 20 or 30 nucleotides in length. A random primer may be of 6 to 30, 8 to 30 or 12 to 30 nucleotides in length. Random primers are typically provided as a mix of oligonucleotides which are representative of all potential combinations of e.g. hexamers, heptamers, octamers or nonamers in the DNA template.

In other embodiments, the primers are specific. This means they have a sequence which is complementary to a sequence in the DNA template from which initiation of amplification is desired. In this embodiment, a pair of primers may be used to specifically amplify a portion of the DNA template which is internal to the two primer binding sites. Primers may be unlabelled, or may comprise one or more labels, for example radionuclides or fluorescent dyes. Primers may also comprise chemically modified nucleotides. Primer lengths/sequences may typically be selected based on temperature considerations i.e as being able to bind to the template at the temperature used in the amplification step.

The contacting of the DNA template with the DNA polymerase and one or more primers takes place under conditions promoting annealing of primers to the DNA template. The conditions include the presence of single-stranded DNA allowing for hybridisation of the primers. The conditions also include a temperature and buffer allowing for annealing of the primer to the template. Appropriate annealing/hybridisation conditions may be selected depending on the nature of the primer. An example of preferred annealing conditions used in the present invention include a buffer 30 mM Tris-HCl pH 7.5, 20 mM KCl, 8 mM MgCl$_2$. The annealing may be carried out following denaturation by gradual cooling to the desired reaction temperature.

Once the DNA template is contacted with the DNA polymerase and one or more primers, there is then a step of incubation under conditions promoting amplification of said template. Preferably, the conditions promote amplification of said template by displacement of replicated strands through strand displacement replication of another strand. The conditions comprise use of any temperature allowing for amplification of DNA, commonly in the range of 20 to 90 degrees centigrade. A preferred temperature range may be about 20 to about 40 or about 25 to about 35 degrees centigrade.

Typically, an appropriate temperature is selected based on the temperature at which a specific DNA polymerase has optimal activity. This information is commonly available and forms part of the general knowledge of the skilled person. For example, where phi29 DNA polymerase is used, a suitable temperature range would be about 25 to about 35 degrees centigrade, preferably about 30 degrees centigrade. The skilled person would routinely be able to identify a suitable temperature for efficient amplification according to the process of the invention. For example, the process could be carried out at a range of temperatures, and yields of amplified DNA could be monitored to identify an optimal temperature range for a given DNA polymerase.

Other conditions promoting amplification of the DNA template comprise the presence of a DNA polymerase and one or more primers. The conditions also include the presence of all four dNTPs, ATP, TTP, CTP and GTP, suitable buffering agents/pH and other factors which are required for enzyme performance or stability. Suitable conditions include any conditions used to provide for activity of DNA polymerase enzymes known in the art.

For example, the pH may be within the range of 3 to 10, preferably 5 to 8 or about 7, such as about 7.5. pH may be maintained in this range by use of one or more buffering agents. Such buffers include, but are not restricted to MES, Bis-Tris, ADA, ACES, PIPES, MOBS, MOPS, MOPSO, Bis-Tris Propane, BES, TES, HEPES, DIPSO, TAPSO, Trizma, HEPPSO, POPSO, TEA, EPPS, Tricine, Gly-Gly, Bicine, HEPBS, TAPS, AMPD, TABS, AMPSO, CHES, CAPSO, AMP, CAPS, CABS, phosphate, citric acid-sodium hydrogen phosphate, citric acid-sodium citrate, sodium acetate-acetic acid, imidazole and sodium carbonate-sodium bicarbonate. The reaction may also comprise salts of divalent metals such as but not limited to salts of magnesium ($Mg^{2+}$) and manganese ($Mn^{2+}$), including chlorides, acetates and sulphates. Salts of monovalent metals may also be included, such as sodium salts and potassium salts, for example potassium chloride. Other salts that may be included are ammonium salts, in particular ammonium sulphate.

Detergents may also be included. Examples of suitable detergents include Triton X-100, Tween 20 and derivatives of either thereof. Stabilising agents may also be included in the reaction. Any suitable stabilising agent may be used, in particular, bovine serum albumin (BSA) and other stabilising proteins. Reaction conditions may also be improved by adding agents that relax DNA and make template denaturation easier. Such agents include, for example, dimethyl sulphoxide (DMSO), formamide, glycerol and betaine.

It should be understood that the skilled person is able to modify and optimise amplification and incubation conditions for the process of the invention on the basis of their general knowledge. Likewise the specific concentrations of particular agents may be selected on the basis of previous examples in the art and further optimised on the basis of general knowledge. As an example, a suitable reaction buffer used in RCA-based methods in the art is 50 mM Tris HCl, pH 7.5, 10 mM $MgCl_2$, 20 mM $(NH_4)_2SO_4$, 5% glycerol, 0.2 mM BSA, 1 mM dNTPs. A preferred reaction buffer used in the RCA amplification of the invention is 35 mM Tris-HCl, 50 mM KCl, 14 mM $MgCl_2$, 10 mM $(NH_4)_2$ SO4, 4 mM DTT, 1 mM dNTP. This buffer is particularly suitable for use with phi29 RCA polymerase.

The reaction conditions may also comprise use of one or more additional proteins. The DNA template may be amplified in the presence of at least one pyrophosphatase, such as Yeast Inorganic pyrophosphatase. Two, three, four, five or more different pyrophosphatases may be used. These enzymes are able to degrade pyrophosphate generated by the DNA polymerase from dNTPs during strand replication. Build up of pyrophosphate in the reaction can cause inhibition of DNA polymerases and reduce speed and efficiency of DNA amplification. Pyrophosphatases can break down pyrophosphate into non-inhibitory phosphate. An example of a suitable pyrophosphatase for use in the process of the present invention is *Saccharomyces cerevisiae* pyrophosphatase, available commercially from New England Biolabs, Inc Any single-stranded binding protein (SSBP) may be used in the process of the invention, to stabilise single-stranded DNA. SSBPs are essential components of living cells and participate in all processes that involve ssDNA, such as DNA replication, repair and recombination. In these processes, SSBPs bind to transiently formed ssDNA and may help stabilise ssDNA structure. An example of a suitable SSBP for use in the process of the present invention is T4 gene 32 protein, available commercially from New England Biolabs, Inc.

In addition to the amplification step, the process of the invention also comprises a processing step for production of closed linear DNA. Amplified DNA is contacted with at least one protelomerase under conditions promoting production of closed linear DNA. This simple processing step based on protelomerase is advantageous over other methods used for production of closed linear DNA molecules. The amplification and processing steps can be carried out simultaneously or concurrently. However, preferably, the amplification and processing steps are carried out sequentially with the processing step being carried out subsequent to the amplification step (i.e on amplified DNA).

A protelomerase used in the invention is any polypeptide capable of cleaving and rejoining a template comprising a protelomerase target site in order to produce a covalently closed linear DNA molecule. Thus, the protelomerase has DNA cleavage and ligation functions. Enzymes having protelomerase-type activity have also been described as telomere resolvases (for example in *Borrelia burgdorferi*). A typical substrate for protelomerase is circular double stranded DNA. If this DNA contains a protelomerase target site, the enzyme can cut the DNA at this site and ligate the ends to create a linear double stranded covalently closed DNA molecule. The requirements for protelomerase target sites are discussed above. As also outlined above, the ability of a given polypeptide to catalyse the production of closed linear DNA from a template comprising a protelomerase target site can be determined using any suitable assay described in the art.

Protelomerase enzymes have been described in bacteriophages. In some lysogenic bacteria, bacteriophages exist as extrachromosomal DNA comprising linear double strands with covalently closed ends. The replication of this DNA and the maintenance of the covalently closed ends (or telomeric ends) are dependent on the activity of the enzyme, protelomerase. The role of protelomerase in the replication of the viral DNA is illustrated in FIG. 1. An example of this catalytic activity is provided by the enzyme, TelN from the bacteriophage, N15 that infects *Escherichia coli*. TelN recognises a specific nucleotide sequence in the circular double stranded DNA. This sequence is a slightly imperfect inverted palindromic structure termed telRL comprising two halves, telR and telL, flanking a 22 base pair inverted perfect repeat (telO) (see FIG. 2). Two telRL sites are formed in the circular double stranded DNA by the initial activity of specific DNA polymerase acting on the linear prophage DNA. TelN converts this circular DNA into two identical linear prophage DNA molecules completing the replication cycle. telR and telL comprise the closed ends of the linear prophage DNA enabling the DNA to be replicated further in the same way.

The process of the invention requires use of at least one protelomerase. The process of the invention may comprise use of more than one protelomerase, such as two, three, four, five or more different protelomerases. Examples of suitable protelomerases include those from bacteriophages such as phiHAP-1 from *Halomonas aquamarina* (SEQ ID NO: 7), PY54 from *Yersinia enterolytica* (SEQ ID NO: 9), phiKO2 from *Klebsiella oxytoca* (SEQ ID NO: 11) and VP882 from *Vibrio* sp. (SEQ ID NO: 13), and N15 from *Escherichia coli* (SEQ ID NO: 15), or variants of any thereof. Use of bacteriophage N15 protelomerase (SEQ ID NO: 15) or a variant thereof is particularly preferred.

Variants of SEQ ID NOs: 7, 9, 11, 13 and 15 include homologues or mutants thereof. Mutants include truncations, substitutions or deletions with respect to the native sequence. A variant must produce closed linear DNA from a template comprising a protelomerase target site as described above.

Any homologues mentioned herein are typically a functional homologue and are typically at least 40% homologous to the relevant region of the native protein. Homology can be measured using known methods. For example the UWGCG Package provides the BESTFIT program which can be used to calculate homology (for example used on its default settings) (Devereux et al (1984) Nucleic Acids Research 12, 387-395). The PILEUP and BLAST algorithms can be used to calculate homology or line up sequences (typically on their default settings), for example as described in Altschul S. F. (1993) J Mol Evol 36:290-300; Altschul, S, F et al (1990) J Mol Biol 215:403-10. Software for performing BLAST analyses is publicly available through the National Center for Biotechnology Information.

The BLAST algorithm performs a statistical analysis of the similarity between two sequences; see e.g., Karlin and Altschul (1993) Proc. Natl. Acad. Sci. USA 90: 5873-5787. One measure of similarity provided by the BLAST algorithm is the smallest sum probability (P(N)), which provides an indication of the probability by which a match between two nucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

A variant polypeptide comprises (or consists of) sequence which has at least 40% identity to the native protein. In preferred embodiments, a variant sequence may be at least 55%, 65%, 70%, 75%, 80%, 85%, 90% and more preferably at least 95%, 97% or 99% homologous to a particular region of the native protein over at least 20, preferably at least 30, for instance at least 40, 60, 100, 200, 300, 400 or more contiguous amino acids, or even over the entire sequence of the variant. Alternatively, the variant sequence may be at least 55%, 65%, 70%, 75%, 80%, 85%, 90% and more preferably at least 95%, 97% or 99% homologous to full-length native protein. Typically the variant sequence differs from the relevant region of the native protein by at least, or less than, 2, 5, 10, 20, 40, 50 or 60 mutations (each of which can be substitutions, insertions or deletions). A variant sequence of the invention may have a percentage identity with a particular region of the full-length native protein which is the same as any of the specific percentage homology values (i.e. it may have at least 40%, 55%, 80% or 90% and more preferably at least 95%, 97% or 99% identity) across any of the lengths of sequence mentioned above.

Variants of the native protein also include truncations. Any truncation may be used so long as the variant is still able to produce closed linear DNA as described above. Truncations will typically be made to remove sequences that are non-essential for catalytic activity and/or do not affect conformation of the folded protein, in particular folding of the active site. Truncations may also be selected to improve solubility of the protelomerase polypeptide. Appropriate truncations can routinely be identified by systematic truncation of sequences of varying length from the N- or C-terminus.

Variants of the native protein further include mutants which have one or more, for example, 2, 3, 4, 5 to 10, 10 to 20, 20 to 40 or more, amino acid insertions, substitutions or deletions with respect to a particular region of the native protein. Deletions and insertions are made preferably outside of the catalytic domain. Insertions are typically made at the N- or C-terminal ends of a sequence derived from the native protein, for example for the purposes of recombinant expression. Substitutions are also typically made in regions that are non-essential for catalytic activity and/or do not affect conformation of the folded protein. Such substitutions may be made to improve solubility or other characteristics of the enzyme. Although not generally preferred, substitutions may also be made in the active site or in the second sphere, i.e. residues which affect or contact the position or orientation of one or more of the amino acids in the active site. These substitutions may be made to improve catalytic properties.

Substitutions preferably introduce one or more conservative changes, which replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative change may introduce another amino acid that is aromatic or aliphatic in the place of a pre-existing aromatic or aliphatic amino acid. Conservative amino acid changes are well known in the art and may be selected in accordance with the properties of the 20 main amino acids as defined in Table A.

TABLE A

| Chemical properties of amino acids | |
|---|---|
| Ala | aliphatic, hydrophobic, neutral |
| Cys | polar, hydrophobic, neutral |
| Asp | polar, hydrophilic, charged (−) |
| Glu | polar, hydrophilic, charged (−) |
| Phe | aromatic, hydrophobic, neutral |
| Gly | aliphatic, neutral |
| His | aromatic, polar, hydrophilic, charged (+) |
| Ile | aliphatic, hydrophobic, neutral |
| Lys | polar, hydrophilic, charged(+) |
| Leu | aliphatic, hydrophobic, neutral |
| Met | hydrophobic, neutral |
| Asn | polar, hydrophilic, neutral |
| Pro | hydrophobic, neutral |
| Gln | polar, hydrophilic, neutral |
| Arg | polar, hydrophilic, charged (+) |

TABLE A-continued

| Chemical properties of amino acids | |
|---|---|
| Ser | polar, hydrophilic, neutral |
| Thr | polar, hydrophilic, neutral |
| Val | aliphatic, hydrophobic, neutral |
| Trp | aromatic, hydrophobic, neutral |
| Tyr | aromatic, polar, hydrophobic |

It is particularly preferred that the variant is able to produce closed linear DNA as described above with an efficiency that is comparable to, or the same as the native protein.

As outlined above, it is preferred that the amplification of DNA according to the process of the invention is carried out by a strand displacement DNA polymerase, more preferably an RCA DNA polymerase. The combination of an RCA DNA polymerase and a protelomerase in an in vitro cell free process allows for surprising efficiency and simplicity in the production of closed linear DNA.

As discussed above, long linear single stranded DNA molecules are initially formed in strand displacement reactions which then serve as new templates, such that double stranded molecules are formed (FIG. 4). The double stranded molecules comprise a continuous series of tandem units of the amplified DNA formed by the processive action of strand displacement polymerases (a concatamer). These concatameric DNA products comprise multiple repeats of the amplified template DNA. A concatamer generated in the process of the invention therefore comprises multiple units of sequence amplified from the DNA template. The concatamer may comprise 10, 20, 50, 100, 200, 500 or 1000 or more units of amplified sequence, depending on the length of the single unit which is to be amplified. The concatamer may be at least 5 kb, at least 10 kb, at least 20 kb, more preferably at least 30 kb, at least 50 kb, or at least 70 kb or greater in size.

In many embodiments, for example in the production of DNA medicines, the amplified DNA will be required for use as a single unit. Therefore, such concatamers require processing to release single units of the amplified DNA. In order to convert this concatemeric DNA into single units of amplified DNA, it needs to be precisely cut and the ends of the paired strands require religation. Conventionally, this could be done by incorporation of restriction endonuclease sites into the DNA template. Thus, restriction endonucleases could be incubated with concatamers to cleave at their recognition sites and release single units. The open linear double stranded DNA formed by the action of restriction endonucleases could then be incubated with a DNA ligase enzyme to covalently close the single unit DNAs.

According to the present invention, the processing of concatameric DNA into closed linear single unit DNAs is achieved by use of a single enzyme, protelomerase. This represents an advantageous simplicity and economy in a process for generation of closed linear DNA molecules. Firstly, cleavage and religation of single units is achieved by incubation with a single enzyme. Secondly, the single units are also released having the desired closed linear structure, and so additional processing steps to generate this structure (i.e from a covalently closed circular single unit DNA) are not required.

The DNA amplified from the DNA template is incubated with at least one protelomerase under conditions promoting production of closed linear DNA. In other words, the conditions promote the cleavage and religation of a double stranded DNA comprising a protelomerase target sequence to form a covalently closed linear DNA with hairpin ends. Conditions promoting production of closed linear DNA comprise use of any temperature allowing for production of closed linear DNA, commonly in the range of 20 to 90 degrees centigrade. The temperature may preferably be in a range of 25 to 40 degrees centigrade, such as about 25 to about 35 degrees centigrade, or about 30 degrees centigrade. Appropriate temperatures for a specific protelomerase may be selected according to the principles outlined above in relation to temperature conditions for DNA polymerases. A suitable temperature for use with E. coli bacteriophage TelN protelomerase of SEQ ID NO: 15 is about 25 to about 35 degrees centigrade, such as about 30 degrees centigrade.

Conditions promoting production of closed linear DNA also comprise the presence of a protelomerase and suitable buffering agents/pH and other factors which are required for enzyme performance or stability. Suitable conditions include any conditions used to provide for activity of protelomerase enzymes known in the art. For example, where E. coli bacteriophage TelN protelomerase is used, a suitable buffer may be 20 mM TrisHCl, pH 7.6; 5 mM $CaCl_2$; 50 mM potassium glutamate; 0.1 mM EDTA; 1 mM Dithiothreitol (DTT). Agents and conditions to maintain optimal activity and stability may also be selected from those listed for DNA polymerases.

In some embodiments, it may be possible to use the same conditions for activity of protelomerase as are used for DNA amplification. In particular, use of the same conditions is described where DNA amplification and processing by protelomerase are carried out simultaneously or concurrently. In other embodiments, it may be necessary to change reaction conditions where conditions used to provide optimal DNA polymerase activity lead to sub-optimal protelomerase activity. Removal of specific agents and change in reaction conditions may be achievable by filtration, dialysis and other methods known in the art. The skilled person would readily be able to identify conditions allowing for optimal DNA polymerase activity and/or protelomerase activity.

In a particularly preferred embodiment, for use in amplification of DNA by an RCA DNA polymerase, preferably phi29, the DNA amplification is carried out under buffer conditions substantially identical to or consisting essentially of 35 mM Tris-HCl, 50 mM KCl, 14 mM $MgCl_2$, 10 mM $(NH_4)_2$ SO4, 4 mM DTT, 1 mM dNTP at a temperature of 25 to 35 degrees centigrade, such as about 30 degrees centigrade. The processing step with protelomerase may then preferably be carried out with TelN, and/or preferably under buffer conditions substantially identical to or consisting essentially of 20 mM TrisHCl, pH 7.6; 5 mM $CaCl_2$; 50 mM potassium glutamate; 0.1 mM EDTA; 1 mM Dithiothreitol (DTT) at a temperature of 25 to 35 degrees centigrade, such as about 30 degrees centigrade. All enzymes and proteins for use in the process of the invention may be produced recombinantly, for example in bacteria. Any means known to the skilled person allowing for recombinant expression may be used. A plasmid or other form of expression vector comprising a nucleic acid sequence encoding the protein of interest may be introduced into bacteria, such that they express the encoded protein. For example, for expression of SEQ ID NOs: 2, 5, 7, 9, 11, 13 or 15, the vector may comprise the sequence of SEQ ID NOs: 1, 4, 6, 8, 10, 12 or 14 respectively. The expressed protein will then typically be purified, for example by use of an affinity tag, in a sufficient quantity and provided in a form suitable for use in the process of the invention. Such methodology for recombinant protein production is routinely available to the skilled person on the basis of their general knowledge. The above discussion applies to the provision of any protein discussed herein.

Amplified DNA obtained by contacting of the DNA template with a DNA polymerase may be purified prior to contacting with a protelomerase. Thus, the process of the invention may further comprise a step of purifying DNA amplified from the DNA template. However, in a preferred embodiment, the process is carried out without purification of amplified DNA prior to contacting with protelomerase. This means the amplification and processing steps can be carried out consecutively, typically in the same container or solution. In some such embodiments, the process involves the addition of a buffer providing for protelomerase activity i.e. to provide conditions promoting formation of closed linear DNA.

Following production of closed linear DNA by the action of protelomerase, the process of the invention may further comprise a step of purifying the linear covalently closed DNA product. The purification referred to above will typically be performed to remove any undesired products. Purification may be carried out by any suitable means known in the art. For example, processing of amplified DNA or linear covalently closed DNA may comprise phenol/chloroform nucleic acid purification or the use of a column which selectively binds nucleic acid, such as those commercially available from Qiagen. The skilled person can routinely identify suitable purification techniques for use in isolation of amplified DNA.

Once linear covalently closed DNA has been generated and purified in a sufficient quantity, the process may further comprise its formulation as a DNA composition, for example a therapeutic DNA composition. A therapeutic DNA composition will comprise a therapeutic DNA molecule of the type referred to above. Such a composition will comprise a therapeutically effective amount of the DNA in a form suitable for administration by a desired route e.g. an aerosol, an injectable composition or a formulation suitable for oral, mucosal or topical administration.

Formulation of DNA as a conventional pharmaceutical preparation may be done using standard pharmaceutical formulation chemistries and methodologies, which are available to those skilled in the art. Any pharmaceutically acceptable carrier or excipient may be used. Auxiliary substances, such as wetting or emulsifying agents, pH buffering substances and the like, may be present in the excipient or vehicle. These excipients, vehicles and auxiliary substances are generally pharmaceutical agents which may be administered without undue toxicity and which, in the case of vaccine compositions will not induce an immune response in the individual receiving the composition. A suitable carrier may be a liposome.

Pharmaceutically acceptable excipients include, but are not limited to, liquids such as water, saline, polyethyleneglycol, hyaluronic acid, glycerol and ethanol. Pharmaceutically acceptable salts can also be included therein, for example, mineral acid salts such as hydrochlorides, hydrobromides, phosphates, sulfates, and the like; and the salts of organic acids such as acetates, propionates, malonates, benzoates, and the like. It is also preferred, although not required, that the preparation will contain a pharmaceutically acceptable excipient that serves as a stabilizer, particularly for peptide, protein or other like molecules if they are to be included in the composition. Examples of suitable carriers that also act as stabilizers for peptides include, without limitation, pharmaceutical grades of dextrose, sucrose, lactose, trehalose, mannitol, sorbitol, inositol, dextran, and the like. Other suitable carriers include, again without limitation, starch, cellulose, sodium or calcium phosphates, citric acid, tartaric acid, glycine, high molecular weight polyethylene glycols (PEGs), and combination thereof. A thorough discussion of pharmaceutically acceptable excipients, vehicles and auxiliary substances is available in REMINGTON'S PHARMACEUTICAL SCIENCES (Mack Pub. Co., N.J. 1991), incorporated herein by reference.

The process of the invention is carried out in an in vitro cell-free environment. Thus, the process is carried out in the absence of a host cell and typically comprises use of purified enzymatic components. Accordingly, the amplification of a template DNA and processing by protelomerase is typically carried out by contacting the reaction components in solution in a suitable container. Optionally, particular components may be provided in immobilised form, such as attached to a solid support.

It should be understood that the process of the invention may be carried out at any scale. However, it is preferred that the process is carried out to amplify DNA at a commercial or industrial scale i.e generating amplified DNA in milligramme or greater quantities. It is preferred that the process generates at least one milligramme, at least 10 milligrammes, at least 20 milligrammes, at least 50 milligrammes or at least 100 milligrammes of amplified DNA. The final closed linear DNA product derived from the amplified DNA may also preferably be generated in milligramme or greater quantities. It is preferred that the process generates al least one milligramme, at least 2 milligrammes, at least 5 milligrammes, at least 10 milligrammes, at least 20 milligrammes, at least 50 milligrammes, or at least 100 milligrammes of closed linear DNA.

The invention further provides a kit comprising components required to carry out the process of the invention. This kit comprises at least one DNA polymerase and at least one protelomerase and optionally instructions for use in a process as described herein. The kit may comprise two, three, four, five or more different DNA polymerases. Preferably, the kit comprises at least one strand displacement-type DNA polymerase, still more preferably an RCA DNA polymerase. It is particularly preferred that the kit comprises phi29 DNA polymerase (SEQ ID NO: 2), Deep Vent® DNA polymerase (SEQ ID NO: 3) or Bst 1 DNA polymerase (SEQ ID NO: 5) or a variant of any thereof. In some embodiments, DNA polymerases that replicate DNA by other methods may also be included. The kit comprises at least one protelomerase. The kit may comprise two, three, four or more different protelomerases. The protelomerases may be selected from any of SEQ ID NOs: 5, 7, 9, 11, 13 or 15 or variants of any thereof. It is particularly preferred that the kit comprises *E. coli* N15 TelN (SEQ ID NO: 15) or a variant thereof.

The kit may also comprise at least one single stranded binding protein (SSBP). A preferred SSBP is T4 gene 32 protein available commercially from New England Biolabs, Inc. Two, three, four or more different SSBPs may be included in the kit. The kit may further comprise a pyrophosphatase. A preferred pyrophosphatase is *S. cerevisiae* pyrophosphatase, available commercially from New England Biolabs, Inc. In some embodiments, two, three, four, five or more different pyrophosphatases may be included. The kit may comprise any DNA polymerase, protelomerase, SSBP or pyrophosphatase described herein. The kit may also comprise dNTPs, suitable buffers and other factors which are required for DNA polymerase and/or protelomerase enzyme performance or stability as described above.

EXAMPLES

Example 1—Expression of TelN and Generation of Vector Constructs Comprising Protelomerase Target Sequences TelN was PCR amplified from the commercially available cloning vector pJAZZ (Lucigen) using modified oligonucleotide primers:

```
                                      (SEQ ID NO: 30)
PT1F 5' ATGAGCAAGGTAAAAATCGGTG 3'

(SEQ ID NO: 31)
PT1R 5' TTAGCTGTAGTACGTTTCCCAT 3'
``` for directional in frame cloning into the commercially available pQE-30 vector (Qiagen). This system allows inducible expression of 6× N-terminal His tagged proteins from a lac promoter whilst providing strong repression in trans from the lad-expressing plasmid pREP4. A number of putative recombinant clones were identified in *E. coli* M15, and validated by sequencing to show in frame insertion of TelN. Six clones were further characterised in small scale induction experiments. All clones expressed a protein of 74.5 kDa corresponding in molecular weight to recombinant TelN protelomerase.

TelN was expressed from *E. coli* M15 pREP4 by inducing protein expression from pQE-30 with IPTG, and induced cells were sonicated (6 bursts of 30 seconds at 100%) and centrifuged (30 min at 25000 g) to yield insoluble and insoluble fractions from the cell lysate. Gel analysis showed presence of TelN in the soluble fraction. Purfication of TelN was carried out on a HisTrap column using an Akta Prime system (GE Healthcare) with elution using a 0-100% (0.5M) imidazole gradient. Purified TelN was dialysed to remove imidazole and stored in a buffer of 10 mM Tris HCl pH 7.4, 75 mM NaCl, 1 mM DTT, 0.1 mM EDTA and 50% glycerol.

Vector constructs allowing for validation of TelN activity were created by directional cloning of synthetic oligonucleotides containing the TelN recognition site telRL:

```
RL1
                                           (SEQ ID NO: 32)
5' AGCTTTATCAGCACACAATTGCCCATTATACGCGCGTATAATGGACT

ATTGTGTGCTGATAG 3'

RL2
                                           (SEQ ID NO: 33)
5'GATCCTATCAGCACACAATAGTCCATTATACGCGCGTATAATGGGCAA

TTGTGTGCTGATAA 3'
``` into the BamHI and HindIII sites of plasmids pUC18 and pBR329. pUC18 has Genbank accession number L09136, and may be obtained commercially from Fermentas Cat no. SD0051; pBR329 has Genbank Accession number J01753 and may be obtained commercially from DSMZ Cat no. 5590].

Additionally, for transfection studies, two copies of the telRL recognition site were cloned into the luciferase expression plasmid pGL4.13 (Promega) at the unique SacI and BamHI restriction sites flanking the expression cassette for the firefly luciferase gene. The first telRL site was cloned into the unique SacI site upstream from the SV40 promoter following reannealing of telRL synthetic oligonucleotides with SacI overhangs. The second telRL site was cloned downstream of the SV40 polyadenylation signal in the unique BamH1 site using telRL synthetic oligonucleotides with BamHI overhangs. The resulting construct was denoted pGL DOG since it allows for the formation of a covalently closed linear (doggybone) DNA encoding luciferase to be expressed in mammalian cells.

Example 2—Validation of TelN Cleavage

Cleavage of supercoiled, circular pUC18 telRL and pGL DOG vector constructs by TelN was validated. 100 ng of each substrate was incubated with 4.5 pmol TelN for 1 hour 40 minutes at 30 degrees centigrade. The reaction was performed in TelN buffer [10 mM Tris HCl pH 7.6, 5 mM $CaCl_2$, 50 mM potassium glutamate, 0.1 mM EDTA, 1 mM DTT].

Cleavage products were visualised by native agarose gel electrophoresis. Incubation of supercoiled, circular pUC18 telRL with TelN released a 2.7 kb linear fragment indicating cleavage. Incubation of supercoiled, circular pGL DOG with TelN released two fragments of 2.4 kb indicating cleavage at the two telRL sites.

Additionally, pUC18 telRL and pGL DOG were linearised by restriction digestion and then incubated with TelN to further validate specific cleavage at telRL. 100 ng pUC18 telRL was linearised with Xmn1 and then incubated with TelN. This released expected fragments of 1.9 kb and 0.8 kb. 100 ng pGL DOG was linearised with Pvu1 and then incubated with TelN. This released expected fragments of 2.4 kb, 1.6 kb and 0.7 kb. Similarly, pGL DOG linearised with Pst1 and then incubated with TelN released expected fragments of 2.4 kb, 1.1 kb and another 1.1 kb. This demonstrated the endonuclease activity of TelN on circular and linear DNA substrates comprising a protelomerase target sequence.

In a preliminary assessment of cleavage activity, it was found that an excess of TelN at 3.4 pmol cut at least 200 ng pUC18 telRL in 1 hour. In a time course experiment, the same amount of DNA was cut within around 10 minutes.

Example 3—Validation of Rejoining Activity of TelN and Formation of Closed Linear DNA Validation of the closed linear DNA structure of the products of TelN cleavage was carried out using denaturing gel electrophoresis. pGL DOG was incubated with TelN as in Example 3. A synthetic PCR product (PCR DOG) corresponding to the region contained within the doggybone, but having open DNA ends was used as a control. The PCR DOG linear fragment was amplified from pGL DOG using primers flanking the telRL sites:

```
                                      (SEQ ID NO: 34)
Sac pGL 5' GTGCAAGTGCAGGTGCCAGAAC 3';

(SEQ ID NO: 35)
Bam pGL 5' GATAAAGAAGACAGTCATAAGTGCGGC 3'.
```

On a native agarose gel [0.8% agarose in TAE buffer (40 mM Tris-acetate, 1 mM EDTA)], the 2.4 kb cleavage product obtained by incubation of 100 ng pGL DOG with TelN migrated to a similar size as PCR DOG (2.7 kb), since both products remain double-stranded.

However, when run on a denaturing agarose gel [1% agarose in H2O run in 50 mM NaOH, 0.1 mM EDTA and neutralised post-run in 1M Tris HCl pH 7.6, 1.5M NaCl] allowing denaturation and separation of double-stranded DNA into single-stranded DNA, the TelN "doggybone"

fragment migrated at a higher molecular weight [ca. 5 kb] than the open-ended PCR control or pUC18 telRL linearised with XmnI (both 2.7 kb).

This difference in migration indicated the formation of a closed linear "doggybone" structure by TelN. Denaturation of a "doggybone" structure would produce single-stranded open circles which migrate more slowly through the gel than the linear single strands released on denaturation of an open-ended linear PCR product.

Validation of the closed linear structure of products formed by TelN was also shown on analysis of thermal denaturation by Lab-On-a-Chip (LOC) capillary electrophoresis. LOC analysis represents a capillary electrophoresis platform for the rapid separation of biological molecules. The Agilent Bioanalyzer with DNA 7500 chips, (Agilent, UK) can be used for the separation and approximate sizing of DNA fragments up to 7000 bp.

This chip system does not detect single stranded DNA. Heat denaturation (95° C. for 5 mins) and rapid (<1° C./s) cooling 1° C./s of conventional double stranded DNA under low salt conditions e.g. in H2O, results in single stranded DNA that cannot be visualised on the LOC system. However, DNA ends that are covalently joined in "doggybone" DNA (resulting from cleavage by TelN) cannot be separated following denaturation and therefore reanneal to reform double stranded DNA that remains visible. Comparison of heat denatured DNA that has been rapidly cooled therefore allows discrimination between covalently closed linear (ccl) doggybone DNA and conventional open linear (ol) double stranded DNA.

DNA samples (100 ng) in H2O were denatured (95° C. for 5 mins), rapidly cooled (<1° C./s) to 4° C. in thin walled PCR tubes in a thermal cycler (Biorad I-cycler, Biorad, UK). For comparison with TelN cleavage, samples were first incubated in 1×Tel N buffer with 1 microlitre purified protelomerase enzyme at 30° C. for 10 min. Control samples were treated identically but without enzyme. Samples (1 microlitre) were analysed using an Agilent Bioanalyser with DNA 7500 chips in accordance with manufacturer's instructions.

Results are shown in FIG. 6B. These show that closed linear "doggybone" DNA obtained by incubation of pGL DOG with TelN is resistant to thermal denaturation as compared with equivalent conventional open linear DNA (PCR DOG). Equivalent resistance against heat denaturation was also obtained using RCA amplified doggybone DNA resulting from RCA amplification and TelN cleavage.

In other experiments, TelN cleavage was carried out on the open-ended PCR DOG. This resulted in the formation of the thermostable cleavage product "doggybone" DNA of 2.8 kb, and thermostable "doggybone" ends of 0.09 and 0.14 kb.

The estimated sizes of "doggybone" and PCR DOG in LOC analysis ranged from 2.8 kb to 3.0 kb and 3.1-3.5 kb respectively compared with sequence data that predicted approximate sizes of 2.4 kb and 2.7 kb. This reflects conformational based differences in migration that occur in non-denaturing LOC analysis.

Example 4—Formation of Closed Linear DNA from Concatameric DNA Formed by RCA (Rolling Circle Amplification)

An in vitro cell free process for amplifying a DNA template and converting the amplified DNA into closed linear "doggybone" DNAs was carried out. RCA using phi29 enzyme from Bacillus subtilis phage phi29 and random hexamers as primers was used under various conditions to amplify covalently closed plasmid templates with and without the telRL site. This led to the amplification of concatameric DNA via the processive strand displacement activity of phi29. Initial work was performed using a TempliPhi kit (GE Healthcare) in accordance with manufacturer's instructions. However this was later substituted by an in house process (using phi29 supplied from NEB) resulting in higher product yields with increased purity.

Denaturation of 40 pg-200 ng closed circular template and annealing of primers was carried out in 10 microlitres of Annealing/denaturation buffer, 30 mM Tris-HCl pH 7.5, 20 mM KCl, 8 mM $MgCl_2$, 20 micromolar random hexamers. Denaturation and annealing was carried out by heating to 95° C. for 1 min, followed by cooling to room temp over 30 min.

10 microlitres reaction buffer [35 mM Tris-HCl, 50 mM KCl, 14 mM $MgCl_2$, 10 mM $(NH_4)_2$ $SO_4$, 4 mM DTT, 10 U phi29, 0.002 U PPi (Yeast Inorganic pyrophosphatase), 1 mM dNTP] was then added to 10 microlitres of annealed DNA/primer reaction.

The 20 microlitre reactions were incubated at 30° C. for 18 hrs. A sample was run on gel to check for formation of concatamers and then the reaction mixture was digested with restriction enzyme or TelN to check products.

Concatameric DNA amplified by RCA was then incubated with TelN. Typically, the RCA amplified DNA substrate was diluted in water and 10×TelN buffer to a final volume of 20 microlitres. Results for pUC18 telRL are shown in FIG. 6A.

As can be seen from the gel in lane 1, the undigested concatameric amplified DNA forms a mesh which does not enter the gel. However, TelN was able to cleave the RCA material resulting in release of a 2.7 kb doggybone fragment (lane 6). Confirmation that the DNA amplified by RCA was the starting template used in the reaction was achieved by restriction digestion with Pvu1 (lanes 2 and 5). pUC18 (no telRL) served as a negative control for TelN activity (lane 3).

Similarly, in other experiments, RCA generated concatamers of pGL DOG were also cleaved by TelN. Accordingly, the process of the invention was shown to be effective in amplifying closed linear DNA from a starting template. Further, it was possible to amplify closed linear DNA in a simple manner using RCA polymerase and protelomerase in sequential steps, without need for intervening purification of amplified DNA.

Example 5—Expression of Amplified Closed Linear DNA

Transfection experiments using HeLa cells were performed to investigate expression of a luciferase reporter gene from closed linear "doggybone" DNA produced in accordance with the invention. Covalently closed circular DNA and the linear PCR DOG control were used as controls.

Transfection was carried out at 60% confluence in 20 mm diameter wells in RPMI and used Transfectam® (Promega) in accordance with manufacturer's instructions. Each transfection used 400 ng of construct DNA. Transfection frequency was normalised within and between experiments by inclusion of an internal control using 40 ng of the Renilla luciferase-expressing plasmid pGL4.73 (containing the hRluc gene from Renilla reniformis) in each transfection. Firefly luciferase (luminescence from Photinus pyralis) and Renilla luciferase activity was measured sequentially using the Dual-Luciferase® Reporter (DLR™) Assay System (Promega). Relative light units were measured using a GloMax Multi Luminometer (Promega) and results were expressed as the ratio of Firefly luciferase/*Renilla* luciferase. All experiments were carried out in triplicate.

Constructs tested in transfection were as follows:
pGL4.13 luc control DNA
pGL4.73 hRluc
PCR DOG
PCR control (fragment from pGL4.13 across luc gene)
pGL DOG (pGL4.13 containing 2 telRL sites)
"doggybone" MP (pGL DOG isolated from mini-prep DNA digested with PvuI (to remove contaminating vector DNA) followed by TelN cleavage)
"doggybone" RCA (pGL DOG amplified by RCA digested with PvuI then cleaved with TelN)
RCA pGL DOG—concatameric DNA produced in the initial RCA amplification of pGL DOG.

Results are shown in FIG. 6C. Closed linear DNA, including that amplified by RCA was shown to express luciferase at higher levels than the open linear PCR constructs. This demonstrates that closed linear DNA produced in accordance with the invention may be used to successfully express luciferase when introduced into mammalian cells.

Sequences of the Invention

TABLE A

*Bacillus bacteriophage* phi29 DNA polymerase nucleic acid sequence (SEQ ID NO: 1)

| | | | | |
|---|---|---|---|---|
| atgaagcata | tgccgagaaa | gatgtatagt | tgtgactttg | agacaactac taaagtggaa 60 |
| gactgtaggg | tatgggcgta | tggttatatg | aatatagaag | atcacagtga gtacaaaata 120 |
| ggtaatagcc | tggatgagtt | tatggcgtgg | gtgttgaagg | tacaagctga tctatatttc 180 |
| cataacctca | aatttgacgg | agcttttatc | attaactggt | tggaacgtaa tggttttaag 240 |
| tggtcggctg | acggattgcc | aaacacatat | aatacgatca | tatctcgcat gggacaatgg 300 |
| tacatgattg | atatatgttt | aggctacaaa | gggaaacgta | agatacatac agtgatatat 360 |
| gacagcttaa | agaaactacc | gtttcctgtt | aagaagatag | ctaaagactt taaactaact 420 |
| gttcttaaag | gtgatattga | ttaccacaaa | gaaagaccag | tcggctataa gataacaccc 480 |
| gaagaatacg | cctatattaa | aaacgatatt | cagattattg | cggaacgtct gttaattcag 540 |
| tttaagcaag | gtttagaccg | gatgacagca | ggcagtgaca | gtctaaaagg tttcaaggat 600 |
| attataacca | ctaagaaatt | caaaaaggtg | tttcctacat | tgagtcttgg actcgataag 660 |
| gaagtgagat | acgcctatag | aggtggtttt | acatggttaa | atgataggtt caaagaaaaa 720 |
| gaaatcggag | aaggcatggt | cttcgatgtt | aatagtctat | atcctgcaca gatgtatagc 780 |
| cgtctccttc | catatggtga | acctatagta | ttcgagggta | aatacgtttg ggacgaagat 840 |
| tacccactac | acatacagca | tatcagatgt | gagttcgaat | tgaaagaggg ctatataccc 900 |
| actatacaga | taaaaagaag | taggttttat | aaaggtaatg | agtacctaaa aagtagcggc 960 |
| ggggagatag | ccgacctctg | gttgtcaaat | gtagacctag | aattaatgaa agaacactac 1020 |
| gatttatata | acgttgaata | tatcagcggc | ttaaaattta | aagcaactac aggtttgttt 1080 |
| aaagatttta | tagataaatg | gacgtacatc | aagacgacat | cagaaggagc gatcaagcaa 1140 |
| ctagcaaaac | tgatgttaaa | cagtctatc | ggtaaattcg | ctagtaaccc tgatgttaca 1200 |
| gggaaagtcc | cttatttaaa | agagaatggg | gcgctaggtt | tcagacttgg agaagaggaa 1260 |
| acaaaagacc | ctgtttatac | acctatgggc | gtttcatca | ctgcatgggc tagatacacg 1320 |
| acaattacag | cggcacaggc | ttgttatgat | cggataatat | actgtgatac tgacagcata 1380 |
| catttaacgg | gtacagagat | acctgatgta | ataaaagata | tagttgaccc taagaaattg 1440 |
| ggatactggg | cacatgaaag | tacattcaaa | agagttaaat | atctgagaca gaagacctat 1500 |
| atacaagaca | tctatatgaa | agaagtagat | ggtaagttag | tagaaggtag tccagatgat 1560 |
| tacactgata | taaaatttag | tgttaaatgt | gcgggaatga | ctgacaagat taagaaagag 1620 |
| gttacgtttg | agaatttcaa | agtcggattc | agtcggaaaa | tgaagcctaa gcctgtgcaa 1680 |
| gtgccgggcg | gggtggttct | ggttgatgac | acattcacaa | tcaaataa 1728 |

*Bacillus bacteriophage* phi29 DNA polymerase amino acid sequence (SEQ ID NO: 2)

| | | | | |
|---|---|---|---|---|
| MKHMPRKMYS | CDFETTTKVE | DCRVWAYGYM | NIEDHSEYKI | GNSLDEFMAW VLKVQADLYF 60 |
| HNLKFDGAFI | INWLERNGFK | WSADGLPNTY | NTIISRMGQW | YMIDICLGYK GKRKIHTVIY 120 |
| DSLKKLPFPV | KKIAKDFKLT | VLKGDIDYHK | ERPVGYKITP | EEYAYIKNDI QIIAERLLIQ 180 |
| FKQGLDRMTA | GSDSLKGFKD | IITTKKFKKV | FPTLSLGLDK | EVRYAYRGGF TWLNDRFKEK 240 |
| EIGEGMVFDV | NSLYPAQMYS | RLLPYGEPIV | FEGKYVWDED | YPLHIQHIRC EFELKEGYIP 300 |
| TIQIKRSRFY | KGNEYLKSSG | GEIADLWLSN | VDLELMKEHY | DLYNVEYISG LKFKATTGLF 360 |
| KDFIDKWTYI | KITSEGAIKQ | LAKLMLNSLY | GKFASNPDVT | GKVPYLKENG ALGFRLGEEE 420 |
| TKDPVYTPMG | VFITAWARYT | TITAAQACYD | RIIYCDTDSI | HLTGTEIPDV IKDIVDPKKL 480 |
| GYWAHESTFK | RVKYLRQKTY | IQDIYMKEVD | GKLVEGSPDD | YTDIKFSVKC AGMTDKIKKE 540 |
| VTFENFKVGF | SRKMKPKPVQ | VPGGVVLVDD | TFTIK | 575 |

TABLE B

*Pyrococcus* sp Deep Vent DNA polymerase amino acid sequence (SEQ ID NO: 3)

| | | | | |
|---|---|---|---|---|
| MILDADYITE | DGKPIIRIFK | KENGEFKVEY | DRNFRPYIYA | LLKDDSQIDE VRKITAERHG 60 |
| KIVRIIDAEK | VRKKFLGRPI | EVWRLYFEHP | QDVPAIRDKI | REHSAVIDIF EYDIPFAKRY 120 |
| LIDKGLIPME | GDEELKLLAF | DIETLYHEGE | EFAKGPIIMI | SYADEEEAKV ITWKKIDLPY 180 |
| VEVVSSEREM | IKRFLKVIRE | KDPDVIITYN | GDSFDLPYLV | KRAEKLGIKL PLGRDGSEPK 240 |
| MQRLGDMTAV | EIKGRIHFDL | YHVIRRTINL | PTYTLEAVYE | AIFGKPKEKV YAHEIAEAWE 300 |

TABLE B-continued

*Pyrococcus* sp Deep Vent DNA polymerase amino acid sequence (SEQ ID NO: 3)

| | | | | | |
|---|---|---|---|---|---|
| TGKGLERVAK | YSMEDAKVTY | ELGREFFPME | AQLSRLVGQP | LWDVSRSSTG | NLVEWYLLRK  360 |
| AYERNELAPN | KPDEREYERR | LRESYAGGYV | KEPEKGLWEG | LVSLDFRSLY | PSIIITHNVS  420 |
| PDTLNREGCR | EYDVAPEVGH | KFCKDFPGFI | PSLLKRLLDE | RQEIKRKMKA | SKDPIEKKML  480 |
| DYRQRAIKIL | ANSYYGYYGY | AKARWYCKEC | AESVTAWGRE | YIEFVRKELE | EKFGFKVLYI  540 |
| DTDGLYATIP | GAKPEEIKKK | ALEFVDYINA | KLPGLLELEY | EGFYVRGFFV | TKKKYALIDE  600 |
| EGKIITRGLE | IVRRDWSEIA | KETQAKVLEA | ILKHGNVEEA | VKIVKEVTEK | LSKYEIPPEK  660 |
| LVIYEQITRP | LHEYKAIGPH | VAVAKRLAAR | GVKVRPGMVI | GYIVLRGDGP | ISKRAILAEE  720 |
| FDLRKHKYDA | EYYIENQVLP | AVLRILEAFG | YRKEDLRWQK | TKQTGLTAWL | NIKKK       775 |

TABLE C

*Bacillus stearothermophilus* DNA polymerase I (polA) nucleic acid sequence (SEQ ID NO: 4)

| | | | | | |
|---|---|---|---|---|---|
| atgaagaaga | agctagtact | aattgatggc | aacagtgtgg | cataccgcgc | cttttttgcc   60 |
| ttgccacttt | tgcataacga | caaaggcatt | catacgaatg | cggttacgg  | gtttacgatg  120 |
| atgttgaaca | aaattttggc | ggaagaacaa | ccgacccatt | tacttgtagc | gtttgacgcc  180 |
| ggaaaaacga | cgttccggca | tgaaacgttt | caagagtata | aaggcggacg | gcaacaaact  240 |
| ccccccggaac | tgtccgagca | gtttccgctt | ttgcgcgagc | tattaaaagc | gtaccgcatt  300 |
| cccgcttatg | aacttgatca | ttacgaagcg | gacgatatta | tcgggacgct | cgctgcccgc  360 |
| gctgagcaag | aagggtttga | agtgaaaatc | atttccggcg | accgcgattt | aacccagctc  420 |
| gcctcccgtc | atgtgacggt | cgatattacg | aaaaaaggga | ttaccgacat | tgagccgtat  480 |
| acgccagaga | ccgttcgcga | aaaatacggc | ctgactccgg | agcaaatagt | ggatttaaaa  540 |
| ggattgatgg | gcgataaatc | cgacaacatc | ccgggcgtgc | ccggcatcgg | ggaaaaaacg  600 |
| gcggtcaagc | tgctgaaatg | atttggtatc | gtggaaaatg | tgctccgcatc | gattgatgag  660 |
| gtgaaagggg | aaaaactgaa | agaaaacttg | cgccaacacc | gggatttagc | tctcttgagc  720 |
| aaacagctgg | cgtccatttg | ccgcgacgcc | ccggttgagc | tgtcgttaga | tgacattgtc  780 |
| tacgaaggac | aagaccgcga | aaaagtcatc | gcgttattta | agaactcgg  | gtttcagtcg  840 |
| ttcttggaaa | aaatggccgc | gccggcagcc | gaagggggaa | aaccgcttga | ggagatggaa  900 |
| tttgccatcg | ttgacgtcat | taccgaagag | atgcttgccg | acaaggcagc | gcttgtcgtt  960 |
| gaggtgatgg | aagaaaacta | ccacgatgcc | ccgattgtcg | aatcgcact  | agtgaacgag 1020 |
| catgggcgat | ttttttatgcg | cccggagacc | gcgctggctg | attcgcaatt | tttagcatgg 1080 |
| cttgccgatg | aaacgaagaa | aaaaagcatg | tttgacgcca | agcgggcgct | cgttgcctta 1140 |
| aagtggaaag | gaattgagct | tcgcgcgtc  | gcctttgatt | tattgctcgc | tgcctatttg 1200 |
| ctcaatccgg | ctcaagatgc | cggcgatatc | gctgcggtgg | cgaaaatgaa | acaatatgaa 1260 |
| gcggtgcggt | cggatgaagc | ggtctatgcc | aaaagcgtca | gcggtcgct  | gccggacgaa 1320 |
| cagacgcttg | ctgagcatct | cgttcgcaaa | gcggcagcca | tttgggcgct | tgagcagccg 1380 |
| tttatgacg  | atttgcggaa | caacgaacaa | gatcaattat | taacgaagct | tgagcagccg 1440 |
| ctggcggcga | ttttgctga  | aatgaattc  | actggggtga | acgtggatac | aaagcggctt 1500 |
| gaacagatgg | gttcggagct | cgccgaacaa | ctgcgtgcca | tcgagcagcg | catttacgag 1560 |
| ctagccggcc | aagagttcaa | cattaactca | ccaaaacagc | tcggagtcat | tttatttgaa 1620 |
| aagctgcagc | taccggtgct | gaagaagacg | aaaacaggct | attcgacttc | ggctgatgtg 1680 |
| cttgagaagc | ttgcgccgca | tcatgaaatc | gtcgaaaaca | ttttgcatta | ccgccagctt 1740 |
| ggcaaactgc | aatcaacgta | tattgaagga | ttgttgaaag | ttgtgcgccc | tgataccggc 1800 |
| aaagtgcata | cgatgttcaa | ccaagcgctg | acgcaaactg | gcggctcag  | ctcggccgag 1860 |
| ccgaacttgc | aaaacattcc | gattcgctc  | gaagagggc  | ggaaaatccg | ccaagcgttc 1920 |
| gtcccgtcag | agccggactg | gctcattttc | gccgccgatt | actcacaat  | tgaattcgc  1980 |
| gtcctcgccc | atatccgcga | tgacgacaat | ctaattgaag | cgttccaacg | cgatttggat 2040 |
| attcacacaa | aaacggcgat | ggacatttc  | catgtgagcg | aagaggaagt | cacggccaac 2100 |
| atgcgccgcc | aggcaaaggc | cgttaacttc | ggtatcgttt | acggaattag | cgattacgga 2160 |
| ttggcgcaaa | acttgaacat | tacgcgcaaa | gaagctgccg | aatttatcga | acgttactc  2220 |
| gccagctttc | cgggcgtaaa | gcagtatatg | aaaacattg  | tgcaagaagc | gaaacagaaa 2280 |
| ggatatgtga | caacgctgtt | gcatcggcgc | cgctatttgc | ctgatattac | aagccgcaat 2340 |
| ttcaacgtcc | gcagttttgc | agagcggacg | gccatgaaca | cgccaattca | aggaagcgcc 2400 |
| gctgacatta | ttaaaaaagc | gatgattgat | ttagcggcac | ggctgaaaga | agagcagttt 2460 |
| caggctcgtc | ttttgctgca | agtgcatgac | gagctcattt | tggaagcgcc | aaaagaggaa 2520 |
| attgagcgat | tatgtgagct | tgttccggaa | gtgatggagc | aggccgttac | gctccgcgtg 2580 |
| ccgctgaaag | tcgactacca | ttacggccca | acatggtatg | atgccaaata | a          2631 |

*Bacillus stearothermophilus* DNA polymerase I (polA) amino acid sequence (SEQ ID NO: 5)

| | | | | | |
|---|---|---|---|---|---|
| MKKKLVLIDG | NSVAYRAFFA | LPLLHNDKGI | HTNAVYGFTM | MLNKILAEEQ | PTHLLVAFDA   60 |
| GKTTFRHETF | QEYKGGRQQT | PPELSEQFPL | LRELLKAYRI | PAYELDHYEA | DDIIGTLAAR  120 |
| AEQEGFEVKI | ISGDRDLTQL | ASRHVTVDIT | KKGITDIEPY | TPETVREKYG | LTPEQIVDLK  180 |
| GLMGDKSDNI | PGVPGIGEKT | AVKLLKQFGT | VENVLASIDE | VKGEKLKENL | RQHRDLALLS  240 |
| KQLASICRDA | PVELSLDDIV | YEGQDREKVI | ALFKELGFQS | FLEKMAAPAA | EGEKPLEEME  300 |

TABLE C-continued

```
FAIVDVITEE MLADKAALVV EVMEENYHDA PIVGIALVNE HGRFFMRPET ALADSQFLAW   360
LADETKKKSM FDAKRAVVAL KWKGIELRGV AFDLLLAAYL LNPAQDAGDI AAVAKMKQYE   420
AVRSDEAVYG KGVKRSLPDE QTLAEHLVRK AAAIWALEQP FMDDLRNNEQ DQLLTKLEQP   480
LAAILAEMEF TGVNVDTKRL EQMGSELAEQ LRAIEQRIYE LAGQEFNINS PKQLGVILFE   540
KLQLPVLKKT KTGYSTSADV LEKLAPHHEI VENILHYRQL GKLQSTYIEG LLKVVRPDTG   600
KVHTMFNQAL TQTGRLSSAE PNLQNIPIRL EEGRKIRQAF VPSEPDWLIF AADYSQIELR   660
VLAHIADDDN LIEAFQRDLD IHTKTAMDIF HVSEEEVTAN MRRQAKAVNF GIVYGISDYG   720
LAQNLNITRK EAAEFIERYF ASFPGVKQYM ENIVQEAKQK GYVTTLLHRR RYLPDITSRN   780
FNVRSFAERT AMNTPIQGSA ADIIKKAMID LAARLKEEQL QARLLLQVHD ELILEAPKEE   840
IERLCELVPE VMEQAVTLRV PLKVDYHYGP TWYDAK                            876
```

TABLE D

*Halomonas* phage phiHAP-1 protelomerase nucleic acid sequence (SEQ ID NO: 6)

```
atgagcggtg agtcacgtag aaaggtcgat ttagcggaat tgatagagtg gttgctcagc     60
gagatcaaag agatcgacgc cgatgatgag atgccacgta aagagaaaac caagcgcatg   120
gcgcgactgg cacgtagctt caaaacgcgc ctgcatgatg acaagcgccg caaggattct   180
gagcggatcg cggtcacgac ctttcgccgc tacatgacag aagcgcgcaa ggcggtgact   240
gcgcagaact ggcgccatca cagcttcgac cagcagatcg agcggctggc cagccgctac   300
ccggcttatg ccagcaagct ggaagcgctc ggcaagctga ccgatatcag cgccattcgt   360
atggcccacc gcgagctgct cgaccagatc cgcaacgctt atgaggacatc                420
cgggcgatga agctggacca tgaaatcatg cgccacctga cgttgagctc tgcacagaaa   480
agcacgctgg ctgaagaggc cagcgagacg ctggaagagc gcgcggtgaa cacggtcgag   540
atcaactacc actggttgat ggagacggtt tacgagctgc tgagtaaccg ggagagaatg   600
gtcgatgggg agtatcgcgg cttttttcagt tacctagcctc ttgggctgga gctggccacc    660
gggcgtcgct cgatcgaggt gctgaagacc ggacggatca cgaaggtggg cgagtatgag   720
ctggagttca gcggccaggc gaaaaagcgc ggcggcgtcg actatagcga ggcttaccac   780
atttatacc tggtgaaagc tgacctggtg atcgaagcgt gggatgagct cgctcgctg    840
ccggaagctg ctgagctgca gggcatggac aacagcgatg tgaaccgccg cacggcgaag   900
acgctcaaca cgctcactaa gcggatcttt aacaacgatg agcgcgttt caaggacagc   960
cgggcgatct gggcgcggct ggtgtttgag ctgcactctt cgccgacaa gcgctggaag  1020
aaagtcaccg aggacgtgtt ctggcgtgag atgctgggc atgaggacat ggatacacag  1080
cgcagctacc gcgcctttaa aatcgactac gacgagcgga tcaagcgcca ccaggaagat  1140
tacgaacacg ctagccgcct cgccgcgctg caggcgctgg acggccatga gcagcttgag  1200
agcagcgacg cccaggcgcg tgtgcatgcc tgggtgaaag cgcagatcga gcaggagcct  1260
gacgcgaaaa ttacgcagtc tctgatcagc cgggagctgg gcgtttatcg ccctgccata  1320
aaagcgtacc tggagctggc gcgagaggcg ctcgacgcgc cgaacgtcga tctggacaag  1380
gtcgcggcgg cagtgccgaa ggaagtagcc gaggcgaagc cccggctgaa cgcccacccc  1440
caaggggatg gcaggtgggt cggggttgct tcaatcaacg gggtggaagt tgcacgggtg  1500
ggcaaccagg caggccggat cgaagcgatg aaagcggcct ataaagcggc gggtgggcgc  1560
tga                                                              1563
```

*Halomonas* phage phiHAP-1 protelomerase amino acid sequence (SEQ ID NO: 7)

```
MSGESRRKVD LAELIEWLLS EIKEIDADDE MPRKEKTKRM ARLARSFKTR LHDDKRRKDS    60
ERIAVITFRR YMTEARKAVT AQNWRHHSFD QQIERLASRY RAYASKLEAL GKLTDISAIR   120
MAHRELLDQI RNDDDAYEDI RAMKLDHEIM RHLTLSSAQK STLAEEASET LEERAVNTVE   180
INYHWLMETV YELLSNRERM VDGEYRGFFS YLALGLALAT GRRSIEVLKT GRITKVGEYE   240
LEFSGQAKKR GGVDYSEAYH IYTLVKADLV IEAWDELRSL PEAAELQGMD NSDVNRRTAK   300
TLNTLIKRIF NNDERVFKDS RAIWARLVFE LHFSRDKRWK KVTEDVFWRE MLGHEDMDTQ   360
RSYRAFKIDY DEPDQADQED YEHASRLAAL QALDGHEQLE SSDAQARVHA WVKAQIEQEP   420
DAKITQSLIS RELGVYRPAI KAYLELAREA LDAPNVDLDK VAAAVPKEVA EAKPRLNAHP   480
QGDGRWVGVA SINGVEVARV GNQAGRIEAM KAAYKAAGGR                          520
```

TABLE E

*Yersinia* phage PY54 protelomerase nucleic acid sequence (SEQ ID NO: 8)

```
atgaaaatcc atttttcgcga tttagttagt ggtttagtta aagagatcga tgaaatagaa     60
aaatcagacc gggcgcaggg tgacaaaact cggcgttatc agggcgcggc cagaaagttc   120
aaaaatgccg tgtttatgga taaacgaaaa tatcgcggta acgtatgaa gaatagaata   180
tcgttaacaa catttaataa atatttaagt cgagcacgtt ctcggtttga agaaaggctt   240
caccatagtt ttcctcaatc tatagcaact atctcaaata aatatcctgc attcagcgaa   300
ataataaaag atctggataa tagacccgct catgaagtta gaataaaact aaagaatta   360
ataactcatc ttgaatccgg tgttaattta ttagaaaaaa taggtagctt agggaaaata   420
aaaccatcta cagctaaaaa aatagttagc ttaaaaaaaa tgtacccatc atgggctaat   480
gatcagata ctttaattag tactgaagat gctacgaat tacaacaaaa gttagagcaa   540
gggaccgacc tacttaacgc attacattct ctaaaagtaa accatgaagt tatgtatgca   600
ttaacgatgc agccttctga cagagctgca ttaaaagcta gcatgacgc tgccttcac    660
tttaaaaagc gtaacatcgt acctatcgat tatcccggct atatgcaacg aatgacggac  720
```

TABLE E-continued

```
atactacatc ttccagatat agcttttgaa gattcgatgg catcacttgc cccttttagca    780
tttgctctag cagctgctag cggtcgcaga caaattgaaa tactaattac tggtgagttt    840
gacgccaaaa ataaaagcat cattaaattt tctggacaag caaaaaaaag aatggccgtt    900
tcaggtggac attatgaaat atacagtcta attgactcag agctattcat tcaacggtta    960
gagttttttac gttctcatag ctcaatactt cgattacaaa atttggaaat agcacacgat   1020
gaacatcgta ctgaactatc tgttattaac ggttttgtag ccaaacccttt aaatgatgca   1080
gcaaaacagt tctttgtcga tgacagaaga gtatttaaag atacccgtgc aatttacgct   1140
cgcatagcat atgaaaaatg gtttagaaca gatcctcgct gggcgaagtg cgacgaagat   1200
gttttcttct ctgaattatt aggccatgac gacccagata ctcagctggc atataaacaa   1260
ttcaagctgg taaatttcaa tccaaaatgg acacctaata tatcagatga aaaccctcgg   1320
ttagctgcac ttcaagagct tgacaatgat atgcccggcc tagcacgtgg cgatgcggca   1380
gttcgcatac atgagtgggt taaagagcaa ctggcgcaga accctgcggc aaaaataact   1440
gcataccaaa tcaagaaaaa tttaaattgt cgaaatgcat tggccagccg atacatgctg   1500
tggtgtgctg acgcgctagg ggttgttatt ggtgatgatg gacaggcaag gccagaagaa   1560
ctcccaccat cgctcgtgct tgatattaac gctgatgaca ctgacgctga agaagatgaa   1620
atagaggaag actttactga tgaggaaata gacgacaccg aattcgacgt atcagataac   1680
gccagtgatg aagataagcc cgaagataaa ccctcgcttg cagcaccaat tcgtagaagt   1740
gaggactctt ggctgattaa atttgaattt gctggcaagc aatatagctg ggagggtaat   1800
gccgaaagtg ttatcgatgc gatgaaacaa gcatggactg aaaatatgga gtaa           1854
```

*Yersinia* phage PY54 protelomerase amino acid sequence (SEQ ID NO: 9)

```
MKIHFRDLVS GLVKEIDEIE KSDRAQGDKT RRYQGAARKF KNAVFMDKRK YRGNGMKNRI    60
SLTTFNKYLS RARSRFEERL HHSFPQSIAT ISNKYPAFSE IIKDLDNRPA HEVRIKLKEL   120
ITHLESGVNL LEKIGSLGKI KPSTAKKIVS LKKMYPSWAN DLDTLISTED ATELQQKLEQ   180
GTDLLNALHS LKVNHEVMYA LTMQPSDRAA LKARHDAALH FKKRNIVPID YPGYMQRMTD   240
ILHLPDIAFE DSMASLAPLA FALAAASGRR QIEILITGEF DAKNKSIIKF SGQAKKRMAV   300
SGGHYEIYSL IDSELFIQRL EFLRSHSSIL RLQNLEIAHD EHRTELSVIN GFVAKPLNDA   360
AKQFFVDDRR VFKDTRAIYA RIAYEKWFRT DPRWAKCDED VFFSELLGHD DPDTQLAYKQ   420
FKLVNFNPKW TPNISDENPR LAALQELDND MPGLARGDAA VRIHEWVKEQ LAQNPAAKIT   480
AYQIKKNLNC RNDLASRYMA WCADALGVVI GDDGQARPEE LPPSLVLDIN ADDTDAEEDE   540
IEEDFTDEEI DDTEFDVSDN ASDEDKPEDK PRFAAPIRRS EDSWLIKFEF AGKQYSWEGN   600
AESVIDAMKQ AWTENME                                                   617
```

TABLE F

*Klebsiella* phage phiKO2 protelomerase nucleic acid sequence (SEQ ID NO: 10)

```
atgcgtaagg tgaaaattgg tgagctaatc aattcgcttg tgagcgaggt cgaggcaatc     60
gatgcctctg atcgtccgca aggcgataaa acgaagaaaa ttaaagccgc agcattaaaa    120
tataagaatg cattatttaa tgacaaaaga aagtttcgcg gtaaaggttt agaaaaaaga    180
atttctgcca acacgttcaa ctcgtatatg agtcgggcaa ggaaaagatt tgatgataga    240
ttgcatcata actttgaaaa gaatgtaatt aaactatcag aaaaatatcc tttatatagt    300
gaagaattat cttcgtggct ttctatgcct gcggcatcaa ttagacagca tatgtcaaga    360
ttgcaagcca agctaaaaga gataatgcca ttggcagaag acttatccaa tataaagatt    420
ggtacaaaaa atagcgaagc aaaaataaat aaactcgcta taaatatcc tgaatggcaa    480
ttcgctatta gtgatttaaa tagcgaagat tggaaggata aaagagatta tcttttataaa    540
ctattccaac aaggttcttc gctcctgaga gacttgaata acctgaaagt aaaccatgag    600
gttctctatc atctgcagct tagttctgcc gagcgaacct ctatccagca gcgctgggcc    660
aacgtcctca gcgagaaaaa gcgcaacgtt gtcgtgattg actatccgcg ctatatgcag    720
gccatctacg atataatcaa caagcctata gtttcgttcg atttgactac tcgtcgtggt    780
atgggccccg tggcgttcgc ccttgccgcg ctatctggtc gccgaatgat tgaaatcatg    840
ctccaggggtg aattttccgt cgcaggtaaa tatacagtaa cattcctggg gcaagctaaa    900
aaacgctcgg aagataaagg tatatcaagg aaaatatata cgttatgcga cgctacttta    960
tttgttagtt tggtaaaatga acttcgctca tgccccgctg ctgccggattt tgatgaagta   1020
ataaaaggat atggcgaaaa tgacactcgc tcagaaaatg ggcgtattaa tgcaattctc    1080
gctacagctt ttaatccgtg ggtaaaaaact ttcttaggcg atgaccgccg cgtttataaa    1140
gatagccgcg ctatttacgc ccgtattgcc tatgaaatgt tcttccgcgt tgaccctcgg    1200
tggaagaatg ttgatgagga tgtattcttc atggagattc tcggccatga cgatgaaaac    1260
acccaactgc actataagca gtttaaattg gctaacttct ccagaacatg gcgaccaaat    1320
gtcggcgcag agaatgcccg cctagcgcgc ctgcaaaagc tggatagcat gatgccagat    1380
tttgcaggcg gcgacgccgg ggttcgtatt catgagacgg tgaagcagct ggttggagcag    1440
gacccatcga taaaaatcac aaacagcacc ctgcgaccgt ttaacttcag taccaggctg    1500
attcctcgct acctggagtt tgccgccgat gcattgggcc agttcgtcgg tgaaaatggg    1560
caatggcaac tgaaggatga ggcgcctgca atagtcctgc ctgatgagga aattcttgag    1620
cctatgacg acgtcgatct cgatgacgaa aaccatgatg atgaaacgct ggatgacgat    1680
gagatcgaag tggacgaaag cgaaggagag gaactggagg aagcgggcga cgctgaagag    1740
gccgaggtgc tgaacaggga agagaagcac cctggcaagc caaactttaa agcgccgagg    1800
gataatggcg atggtaccta catggtgaaa tttgaattcg gtggccgtca ttacgcctgg    1860
tccggtgccg ccggtaatcg ggtagaggca atgcaatctg cctggagtgc ctacttcaag    1920
tga                                                                  1923
```

TABLE F-continued

Klebsiella phage phiKO2 protelomerase amino acid sequence (SEQ ID NO: 11)

```
MRKVKIGELI NSLVSEVEAI DASDRPQGDK TKKIKAAALK YKNALFNDKR KFRGKGLEKR    60
ISANTFNSYM SRARKRFDDR LHHNFEKNVI KLSEKYPLYS EELSSWLSMP AASIRQHMSR   120
LQAKLKEIMP LAEDLSNIKI GTKNSEAKIN KLANKYPEWQ FAISDLNSED WKDKRDYLYK   180
LFQQGSSLLE DLNNLKVNHE VLYHLQLSSA ERTSIQQRWA NVLSEKKRNV VVIDYPRYMQ   240
AIYDIINKPI VSFDLTTRRG MAPLAFALAA LSGRRMIEIM LQGEFSVAGK YTVTFLGQAK   300
KRSEDKGISR KIYILCDATL FVSLVNELRS CPAAADFDEV IKGYGENDTR SENGRINAIL   360
ATAFNPWVKT FLGDDRRVYK DSRAIYARIA YEMFFRVDPR WKNVDEDVFF MEILGHDDEN   420
TQLHYKQFKL ANFSRTWRPN VGEENARLAA LQKLDSMMPD FARGDAGVRI HETVKQLVEQ   480
DPSIKITNST LRPFNFSTRL IPRYLEFAAD ALGQFVGENG QWQLKDEAPA IVLPDEEILE   540
PMDDVDLDDE NHDDETLDDD EIEVDESEGE ELEEAGDAEE AEVAEQEEKH PGKPNFKAPR   600
DNGDGTYMVE FEFGGRHYAW SGAAGNRVEA MQSAWSAYFK                         640
```

TABLE G

Vibrio phage VP882 protelomerase nucleic acid sequence (SEQ ID NO: 12)

```
atgagcggcg aaagtagaca aaaggtaaac ctcgaggagt taataaatga gctcgtcgag    60
gaggtgaaaa ccatcgatga caatgaggcg attactcggt ctgaaaaaac caagttgatc   120
accaggcgg cgactaaatt caagaccaag ctgcacgacg ataagcgccg gaaggatgca   180
accagaatcg ctctgagcac ctatcgtaag tacatgacaa tggccagggc agcagttact   240
gagcagaact ggaaacacca cagtctcgag cagcagatag agcggctggc caaaaagcac   300
ccgcaatacg ctgagcagct ggtggccatc ggggccatgg ataacatcac cgagttgcgc   360
ctggcgcatc gcgacctcct gaagagcatc aaggacaacg atgaagcctt cgaggatatc   420
cgcagcatga agttagacca cgaggtaatg cgccatctga cgctacccag tgcgcaaaag   480
gcgagactgg cagaggaagc cgccgaggcg ttgaccgaga gaaaaccgc cacggtcgac   540
atcaactatc acgagctgat ggccggcgtg gtggagctgt tgaccaagaa gaccaagacg   600
gtcggcagcg acagcaccta cagcttcagc cggctgggcc ttggtattgg cctggctacc   660
ggtcgtcgtt ctatcgagat actgaagcag ggcgagttca aaaaggtgga tgagcagcga   720
ctcgagttct ctggccaagc gaaaaagcgc ggcggtgccg actattcaga gacctatacc   780
atttacaccc tggtcgactc cgacctggta ctgatggcgc tgaagaacct gcgagagttg   840
ccagaagttc gcgcactgga tgagtacgac caactgggcg agattaagcg gaacgacgcc   900
atcaataaac gctgtgcaaa aacgctcaac caaaccgcca agcagttctt tggcagcgac   960
gagcgcgtgt tcaaagatag tcgtgccatc tgggcgcgtc tggcttatga gttgtttttt  1020
caacgtgatc cgcgctggaa aaagaaagac gaggacgttt tctggcagga gatgctgggc  1080
cacgaggaca tcgagactca gaaagccgat aagcaattca aggtcgacta cagcgaacct  1140
gagcagccgg tgcacaagcc tggcaaattt aagagcagag ctgaagccct cgcggcgctc  1200
gactcaaatg aggacattac cacccgctca tccatggcca agatccacga ctgggtgaaa  1260
gagcgtattg cggaagaccc cgaggcgaac atcacacagt cactcatcac ccgggaactg  1320
ggctcaggcc gtaaggtgat caaggactac ctcgacctgg ctgacgatgc ccttgctgtg  1380
gtgaatactc ctgtcgatga cgcagtcgtc gaggttccag ctgatgtgcc ggcagcagaa  1440
aaacagccga gaaagcgca gaagcccaga ctcgtggctc accaggttga tgatgagcac  1500
tgggaagcct gggcgctggt ggaaggcgag gaggtggcca gggtgaaaat caagggcacc  1560
cgcgttgagg caatgacagc cgcatgggag gccagccaaa aggcactcga tgactaa     1617
```

Vibrio phage VP882 protelomerase amino acid sequence (SEQ ID NO: 13)

```
MSGESRQKVN LEELINELVE EVKTIDDNEA ITRSEKTKLI TRAATKFKTK LHDDKRRKDA    60
TRIALSTYRK YMTMARAAVT EQNWKHHSLE QQIERLAKKH PQYAEQLVAI GAMDNITELR   120
LAHRDLLKSI KDNDEAFEDI RSMKLDHEVM RHLTLPSAQK ARLAEEAAEA LTEKKTATVD   180
INYHELMAGV VELLTKKTKT VGSDSTYSFS RLALGIGLAT GRRSIEILKQ GEFKKVDEQR   240
LEFSGQAKKR GGADYSETYT IYTLVDSDLV LMALKNLREL PEVRALDEYD QLGEIKRNDA   300
INKRCAKTLN QTAKQFFGSD ERVFKDSRAI WARLAYELFF QRDPRWKKKD EDVFWQEMLG   360
HEDIETQKAY KQFKVDYSEP EQPVHKPGKF KSRAEALAAL DSNEDITTRS SMAKIHDWVK   420
ERIAEDPEAN ITQSLITREL GSGRKVIKDY LDLADDALAV VNTPVDDAVV EVPADVPAAE   480
KQPKKAQKPR LVAHQVDDEH WEAWALVEGE EVARVKIKGT RVEAMTAAWE ASQKALDD     538
```

TABLE H

Escherichia coli bacteriophage N15 telomerase (telN) and secondary immunity repressor (cA) nucleic acid sequence (SEQ ID NO: 14)

```
catatgcact atatcatatc tcaattacgg aacatatcag cacacaattg cccattatac    60
gcgcgtataa tggactattg tgtgctgata aggagaacat aagcgcagaa caatatgtat   120
ctattccggt gttgtgttcc tttgttattc tgctattatg ttctcttata gtgtgacgaa   180
agcagcataa ttaatcgtca cttgttcttt gattgtgtta cgatatccag agacttagaa   240
acgggggaac cggatgagc aaggtaaaaa tcggtgagtt gatcaacacg cttgtgaatg   300
aggtagaggc aattgatgcc tcagaccgcc cacaaggcga caaacgaag agaattaaag   360
ccgcagccgc acggtataag aacgcgttat ttaatgataa aagaaagttc cgtgggaaag   420
gattgcagaa aagaataacc gcgaatactt ttaacgccta tgagcagg caagaaagc   480
ggtttgatga taaattacat catagctttg ataaaaatat taataaatta tcggaaaagt   540
atcctctttta cagcgaagaa ttatcttcat ggctttctat gcctacggct aatattcgcc   600
agcacatgtc atcgttacaa tctaaattga aagaaataat gccgcttgcc gaagagttat   660
```

TABLE H-continued

```
caaatgtaag aataggctct aaaggcagtg atgcaaaaat agcaagacta ataaaaaaat    720
atccagattg gagttttgct cttagtgatt taaacagtga tgattggaag gagcgccgtg    780
actatcttta taagttattc caacaaggct ctgcgttgtt agaagaacta caccagctca    840
aggtcaacca tgaggttctg taccatctgc agctaagccc tgcggagcgt acatctatac    900
agcaacgatg ggccgatgtt ctgcgcgaga agaagcgtaa tgttgtggtt attgactacc    960
caacatacat gcagtctatc tatgatattt tgaataatcc tgcgacttta tttagtttaa   1020
acactcgttc tggaatggca cctttggcct ttgctctggc tgcggtatca gggcgaagaa   1080
tgattgagat aatgtttcag ggtgaatttg ccgtttcagg aaagtatacg gttaatttct   1140
cagggcaagc taaaaaacgc tctgaagata aagcgtaac cagaacgatt tatactttat    1200
gcgaagcaaa attattcgtt gaattattaa cagaattgcg ttcttgctct gctgcatctg   1260
atttcgatga ggttgttaaa ggatatgaaa aggatgaac aaggtctgag aacggcagga    1320
taaatgctat tttagcaaaa gcatttaacc cttgggttaa atcattttc ggcgatgacc     1380
gtcgtgttta taagatagc cgcgctattt acgctcgcat cgcttatgag atgttcttcc     1440
gcgtcgatcc acggtggaaa aacgtcgacg aggatgtgtt cttcatggag attctcggac   1500
acgacgatga aacacccag ctgcactata agcagttcaa gctggccaac ttctccagaa     1560
cctggcgacc tgaagttggg gatgaaaaca ccaggctggt ggctctgcag aaactggacg   1620
atgaaatgcc aggctttgcc agaggtgacg ctgcgctccg tctccatgaa accgttaagc   1680
agctggtgga gcaggaccca tcagcaaaaa taaccaacag cactctccgg gcctttaaat   1740
ttagcccgac gatgattagc cggtacctgg agtttgccgc tgatgcattg gggcagttcg   1800
ttggcgagaa cgggcagtgg cagctgaaga tagagacacc tgcaatcgtc ctgcctgatg   1860
aagaatccgt tgagaccatc gacgaaccgg atgatgagtc ccaagacgac gagctggatg   1920
aagatgaaat tgagctcgac gagggtggcg gcgatgaacc aaccgaagag gaagggccag   1980
aagaacatca gccaactgct ctaaaacccg tcttcaagcc tgcaaaaaat aacggggacg   2040
gaacgtacaa gatagagttt gaatacgatg gaaagcatta tgcctggtcc ggccccgccg   2100
atagccctat ggccgcaatg cgatccgcat gggaaacgta ctacagctaa agaaaagcc    2160
accggtgtta atcggtggct ttttttattga ggcctgtccc tacccatccc ctgcaaggga   2220
cggaaggatt aggcggaaac tgcagctgca actacggaca tcgccgtccc gactgcaggg   2280
acttccccgc gtaaagcggg gcttaaattc gggctggcca accctatttt tctgcaatcg   2340
ctggcgatgt tagtttcgtg gatagcgttt ccagctttc aatggccagc tcaaaatgtg    2400
ctggcagcac cttctccagt tccgtatcaa tatcggtgat cggcagctct ccacaagaca   2460
tactccggca accgccacga actacatcgc gcagcagctc ccgttcgtag acacgcatgt   2520
tgcccagage cgtttctgca gccgttaata tccggccgac tcggcgatg attgccggga    2580
gatcatccac ggttattggg ttcggtgatg ggttcctgca ggcgcggcgg agagccatcc   2640
agacgccgct aacccatgcg ttacggtact gaaaactttg tgctatgtcg tttatcaggc   2700
ccgaagttct tctttctgcc gccagtccag tggttcaccg gcgttcttag gctcaggctc   2760
gacaaaagca tactcgccgt ttttccggat agctggcaga acctcgttcg tcacccactt   2820
gcggaaccgc caggctgtcg tccccctgttt caccgcgtcg cggcagcgga ggattatggt   2880
gtagagacca gattccgata ccacatttac ttccctgcca atccgatcaa gttttttgtc    2940
ctcggttaaa ccgagggtca atttttcatc atgatccagc ttacgcaatg catcagaagg   3000
gttggctata ttcaatgcag cacagatatc cagcgccaca aaccacgggt caccaccgac    3060
aagaaccacc cgtataggt ggcttccctg aaatgaaaag acggagagag ccttcattgc    3120
gcctccccgg atttcagctg ctcagaaagg gacagggagc agccgcgagc ttcctgcgtg   3180
agttcgcgcg cgacctgcag aagttccgca gcttcctgca aatacagcgt ggcctcataa   3240
ctggagatag tgcggtgagc agagcccaca agcgcttcaa cctgcagcag gcgttcctca   3300
atcgtctcca gcaggccctg ggcgtttaac tgaatctggt tcatgcgatc acctcgctga   3360
ccgggatacg ggctgacaga acgaggacaa aacggctggc gaactggcga cgagcttctc   3420
gctcggatga tgcaatggtg gaaggcggt ggatatggga ttttttgtcc gtgcggacga     3480
cagctgcaaa tttgaatttg aacatggtat gcattcctat cttgtatagg gtgctaccac   3540
cagagttgag aatctctata ggggtggtag cccagacagg gttctcaaca ccggtacaag   3600
aagaaaccgg cccaaccgaa gttggcccca tctgagccac cataattcag gtatgcgcag   3660
atttaacaca caaaaaaaca cgctggcgcg tgttgtgcgc ttcttgtcat tcggggttga   3720
gaggccggc tgcagatttt gctgcagccgg ggtaactcta cgccaaagc agaacgacg     3780
tcaataattt aggtggatat tttaccccgt gaccagtcac gtgcacaggt gttttttatag   3840
tttgctttac tgactgatca gaacctgatc agttattgga gtccggtaat cttattgatg   3900
accgcagcca ccttagatgt tgtctcaaac cccatacggc cacgaatgag ccactggaac   3960
ggaatagtca gcaggtacag cggaacgaac cacaaacggt tcagacgctg ccagaacgtc   4020
gcatcacgac gttccatcca ttcggtattg tcgac                              4055
```

Escherichia coli bacteriophage N15 telomerase amino acid sequence (SEQ ID NO: 15)

```
MSKVKIGELI NTLVNEVEAI DASDRPQGDK TKRIKAAAAR YKNALFNDKR KFRGKGLQKR    60
ITANTFNAYM SRARKRFDDK LHHSFDKNIN KLSEKYPLYS EELSSWLSMP TANIRQHMSS   120
LQSKLKEIMP LAEELSNVRI GSKGSDAKIA RLIKKYPDWS FALSDLNSDD WKERRDYLYK   180
LFQQGSALLE ELHQLKVNHE VLYHLQLSPA ERTSIQQRWA DVLREKKRNV VVIDYPTYMQ   240
SIYDILNNPA TLFSLNTRSG MAPLAFALAA VSGRRMIEIM FQGEFAVSGK YTVNFSGQAK   300
KRSEDKSVTR TIYTLCEAKL FVELLTELRS CSAASDFDEV VKGYGKDDTR SENGRINAIL   360
AKAFNPWVKS FFGDDRRVYK DSRAIYARIA YEMFFRVDPR WKNVDEDVFF MEILGHDDEN   420
TQLHYKQFKL ANFSRTWRPE VGDENTRLVA LQKLDDEMPG FARGDAGVRL HETVKQLVEQ   480
DPSAKITNST LRAFKFSPTM ISRYLEFAAD ALGQFVGENG QWQLKIETPA IVLPDEESVE   540
TIDEPDDESQ DDELDEDEIE LDEGGGDEPT EEEGPEEHQP TALKPVFKPA KNNGDGTYKI   600
EFEYDGKHYA WSGPADSPMA AMRSAWETYY S                                  631
```

The invention claimed is:

1. A method of inducing an immune response against an antigen in a host, said method comprising:
    carrying out a process for production of linear double stranded deoxyribonucleic (DNA) covalently closed at both ends by hairpin loops, comprising:
    (a) amplifying a DNA template comprising at least one protelomerase target sequence to produce a product comprising multiple protelomerase target sequences; and
    (b) producing linear double stranded DNA covalently closed at both ends by hairpin loops by contacting the product comprising multiple protelomerase target sequences produced in (a) with at least one protelomerase under suitable conditions,
    wherein steps (a) and (b) occur in an in vitro cell-free environment, wherein said DNA template encodes said antigen, and
    administering the resulting closed linear DNA encoding said antigen to said host in such a way that said antigen is expressed in said host and induces an immune response against said antigen.

2. A method as claimed in claim 1 wherein said antigen is for the treatment or prevention of conditions selected from any one of cancer, allergies, toxicity or infection by a pathogen.

3. A method as claimed in claim 1 wherein said antigen is a tumour antigen.

4. A method as claimed in claim 3 wherein said tumour antigen is selected from any one of: members of the MAGE family, NY-ESO-I and SSX-2, differentiation antigens, mutated self-antigens, viral tumour antigens, MART-I, Melan-A, p97, beta-HCG, GalNAc, MAGE-1, MAGE-2, MAGE-4, MAGE-12, MUC1, MUC2, MUC3, MUC4, MUC18, CEA, DDC, HA, EpCam, melanoma antigen gp75, Hker 8, high molecular weight melanoma antigen, K19, Tyr1, Tyr2, members of the pMel 17 gene family, c-Met, PSM, PSMA, prostate secretary protein, alpha-fetoprotein, CA 125, CA 19.9, TAG-72, E6 and/or E7 from oncogenic HPV types, tyrosinase, gpl00, PSA, Her-2, CEA, BRCA-I and BRCA-2 antigen.

5. A method as claimed in claim 2 wherein the antigen is for treatment or prevention of conditions related to infection by a pathogen, wherein said pathogen is selected from one of the following:

viruses including Human Papilloma Viruses (HPV), HIV, HSV2/HSV1, Influenza virus (types A, B and C), Polio virus, RSV virus, Rhinoviruses, Rotaviruses, Hepatitis A virus, Norwalk Virus Group, Enteroviruses, Astroviruses, Measles virus, Parainfluenza virus, Mumps virus, Varicella-Zoster virus, Cytomegalovirus, Epstein-Barr virus, Adenoviruses, Rubella virus, Human T-cell Lymphoma type I virus (HTLV-I), Hepatitis B virus (HBV), Hepatitis C virus (HCV), Hepatitis D virus, Pox virus, Marburg and Ebola;

bacteria including *Mycobacterium tuberculosis, Chlamydia, Neisseria gonorrhoeae, Shigella, Salmonella, Vibrio cholerae, Treponema pallidum, Pseudomonas, Bordetella pertussis, Brucella, Frandscella tularensis, Helicobacter pylori, Leptospira interrogans, Legionella pneumophila, Yersinia pestis, Streptococcus* (types A and B), *Pneumococcus, Meningococcus, Haemophilus influenza* (type b), *Toxoplasma gondii, Campylobacteriosis, Moraxella catarrhalis, Donovanosis*, and *Actinomycosis;* fungal pathogens including Candidiasis and Aspergillosis; and parasitic pathogens including *Taenia*, Flukes, Roundworms, Amoebiasis, Giardiasis, *Cryptosporidium, Schistosoma, Pneumocystis carinii, Trichomoniasis* and *Trichinosis.*

6. The method of claim 1 wherein said antigen is from a member of the adenoviridae, herpesviridae, papovaviridae, poxviridae, parvoviridae, reoviridae, coronaviridae, flaviviridae, picornaviridae, togaviridae, filoviridae, paramyxoviridae, rhabdoviridae, bunyaviridae, orthomyxoviridae, retroviridae and hepadnaviridae.

\* \* \* \* \*